(12) United States Patent
Stevens et al.

(10) Patent No.: US 7,794,717 B2
(45) Date of Patent: Sep. 14, 2010

(54) HIGH AFFINITY HUMAN ANTIBODIES TO HUMAN IL-4 RECEPTOR

(75) Inventors: Sean Stevens, Mohegan Lake, NY (US); Tammy T. Huang, Golden Bridge, NY (US); Joel H. Martin, Putnam Valley, NY (US); Jeanette L. Fairhurst, White Plains, NY (US); Ashique Rafique, Yonkers, NY (US); Marcela Torres, New Milford, NJ (US); Kevin J. Pobursky, Beacon, NY (US); Raymond W. Leidich, Middletown, NY (US); Joan A. Windsor, Brooklyn, NY (US); Warren R. Mikulka, Brewster, NY (US); Diana M. Ahrens, Mahopac, NY (US); Ergang Shi, Ossining, NY (US); Nicholas J. Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 12/554,029

(22) Filed: Sep. 4, 2009

(65) Prior Publication Data
US 2010/0021476 A1   Jan. 28, 2010

Related U.S. Application Data

(62) Division of application No. 11/906,517, filed on Oct. 2, 2007, now Pat. No. 7,605,237.

(60) Provisional application No. 60/957,738, filed on Aug. 24, 2007, provisional application No. 60/848,694, filed on Oct. 2, 2006.

(51) Int. Cl.
*A61K 39/00* (2006.01)

(52) U.S. Cl. .............. 424/133.1; 424/143.1; 530/387.3; 530/388.22

(58) Field of Classification Search .............. 424/133.1, 424/143.1; 530/387.3, 388.22
See application file for complete search history.

(56) References Cited

U.S. PATENT DOCUMENTS

| | | | |
|---|---|---|---|
| 5,599,905 | A | 2/1997 | Mosley et al. |
| 5,714,146 | A | 2/1998 | Lewis |
| 5,717,072 | A | 2/1998 | Mosley |
| 5,856,296 | A | 1/1999 | Mosley et al. |
| 5,985,280 | A | 11/1999 | Ritter |
| 6,156,877 | A | 12/2000 | Ritter et al. |
| 6,391,581 | B1 | 5/2002 | Mosley et al. |
| 6,716,587 | B2 | 4/2004 | Mosley |
| 7,186,809 | B2 | 3/2007 | Pluenneke |
| 7,317,090 | B2 | 1/2008 | Mosley et al. |
| 2005/0255532 | A1 | 11/2005 | Ruben |
| 2005/0282181 | A1 | 12/2005 | Yan |
| 2007/0041976 | A1 | 2/2007 | Pluenneke |
| 2007/0274996 | A1 | 11/2007 | Carter et al. |
| 2009/0074793 | A1 | 3/2009 | Martin |
| 2009/0098142 | A1 | 4/2009 | Kasaian et al. |

FOREIGN PATENT DOCUMENTS

| | | |
|---|---|---|
| EP | 0 604 693 | 7/1994 |
| EP | 0 367 566 A1 | 5/1997 |
| WO | WO 01/92340 | 12/2001 |
| WO | WO 2005/047331 | 5/2005 |
| WO | WO 2005/085284 | 9/2005 |
| WO | WO 2006/072564 | 7/2006 |

OTHER PUBLICATIONS

Gavett et al. (Am J Physiol. Feb. 1997; 272 (2 Pt 1): L253-61).*
Tomkinson et al. (J Immunol. May 1, 2001; 166 (9): 5792-800).*
Maliszewski et al. (Proc Soc Exp Biol Med. Jul. 1994; 206 (3): 233-7).*
Sato et al. (J Immuno. Apr. 1, 1993; 150 &): 2717-23).*
Zurawski et al., 1995, "The primary binding subunit of the human interleukin-4 receptor is also . . . " J. Biol. Chem. 270:13869-13878 (Am. Society Biochem Mol. Biol, USA).
Holt et al., 2003, "Domain antibodies: Proteins for Therapy," Trends Biotechnol. 21:484-490 (Cell Press, Cambridge, GB).
Davies et al., 1996, "Affinity improvement of single antibody VH domains: residues in all three hypervariable regions . . . " Immunotechnol. 2:169-179 (Elsevier, Netherlands).

* cited by examiner

*Primary Examiner*—Stephen L Rawlings
(74) *Attorney, Agent, or Firm*—Frank R. Cottingham

(57) ABSTRACT

The present invention provides methods for treating one or more diseases or disorders which are improved, inhibited or ameliorated by reducing interleukin-4 (IL-4) activity. The methods of the invention comprise administering to a patient an antibody, or antigen-binding fragment thereof, which specifically binds to a human IL-4 receptor.

4 Claims, 3 Drawing Sheets

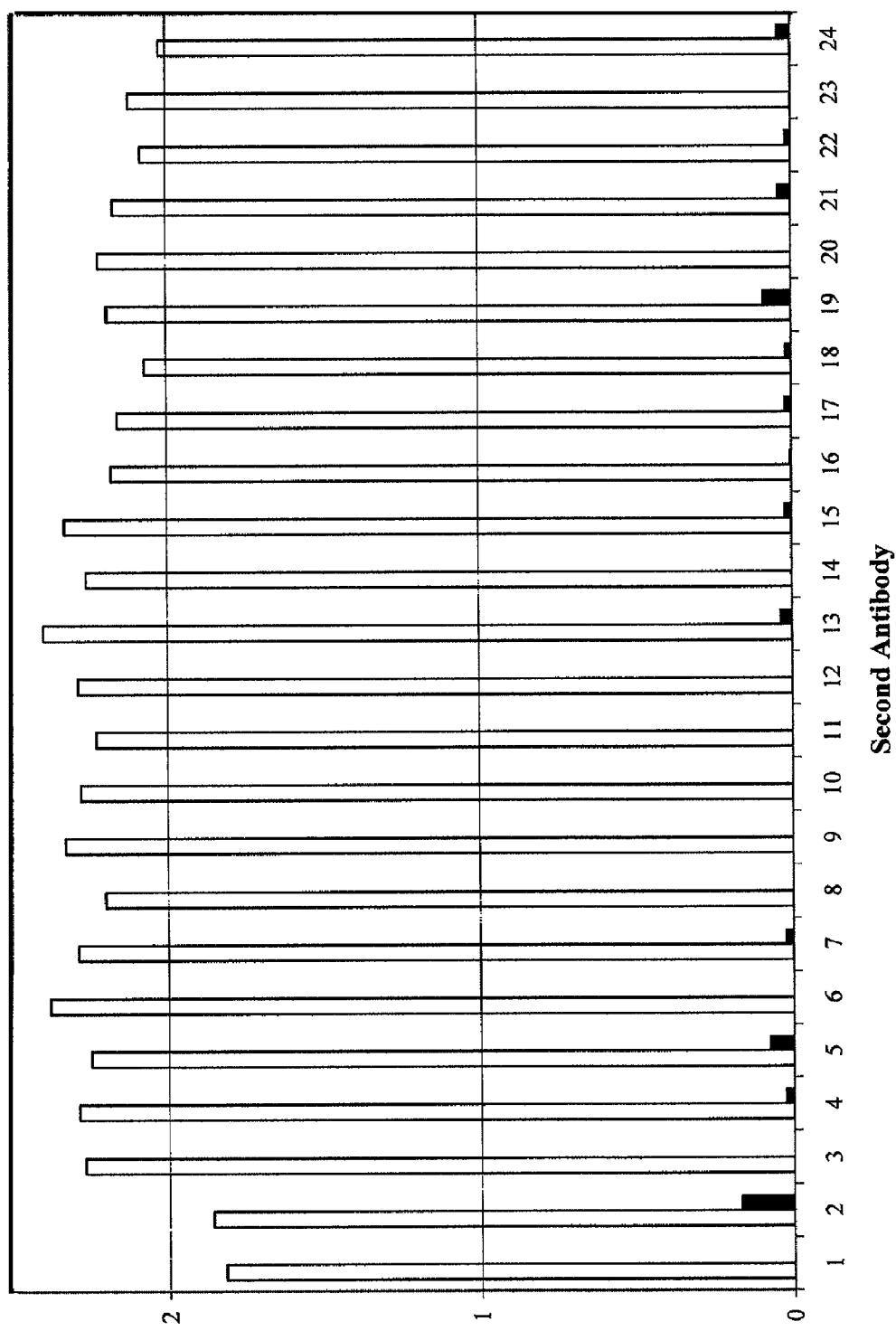

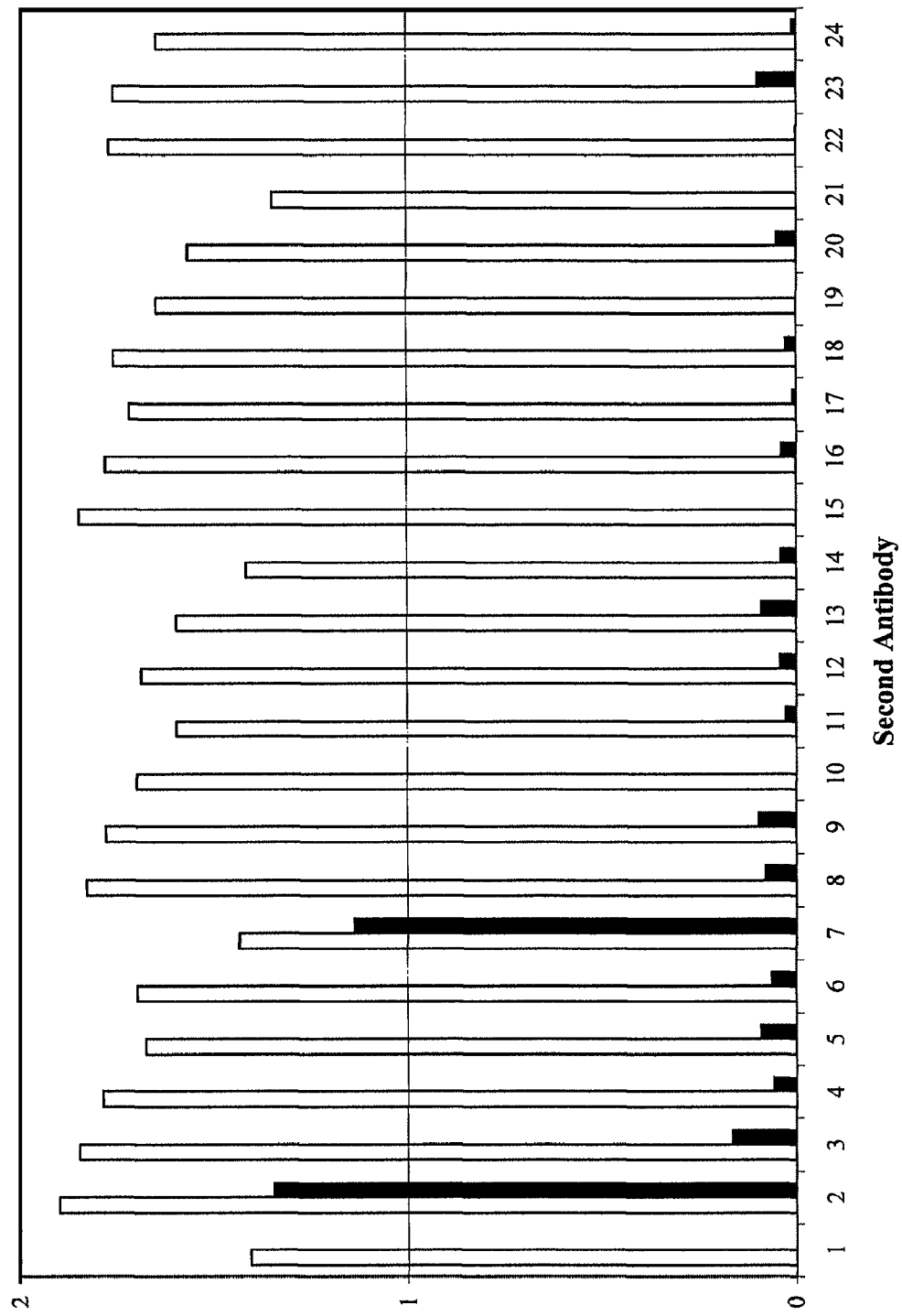

HIGH AFFINITY HUMAN ANTIBODIES TO HUMAN IL-4 RECEPTOR

CROSS-REFERENCE TO RELATED APPLICATIONS

Figure 1B:
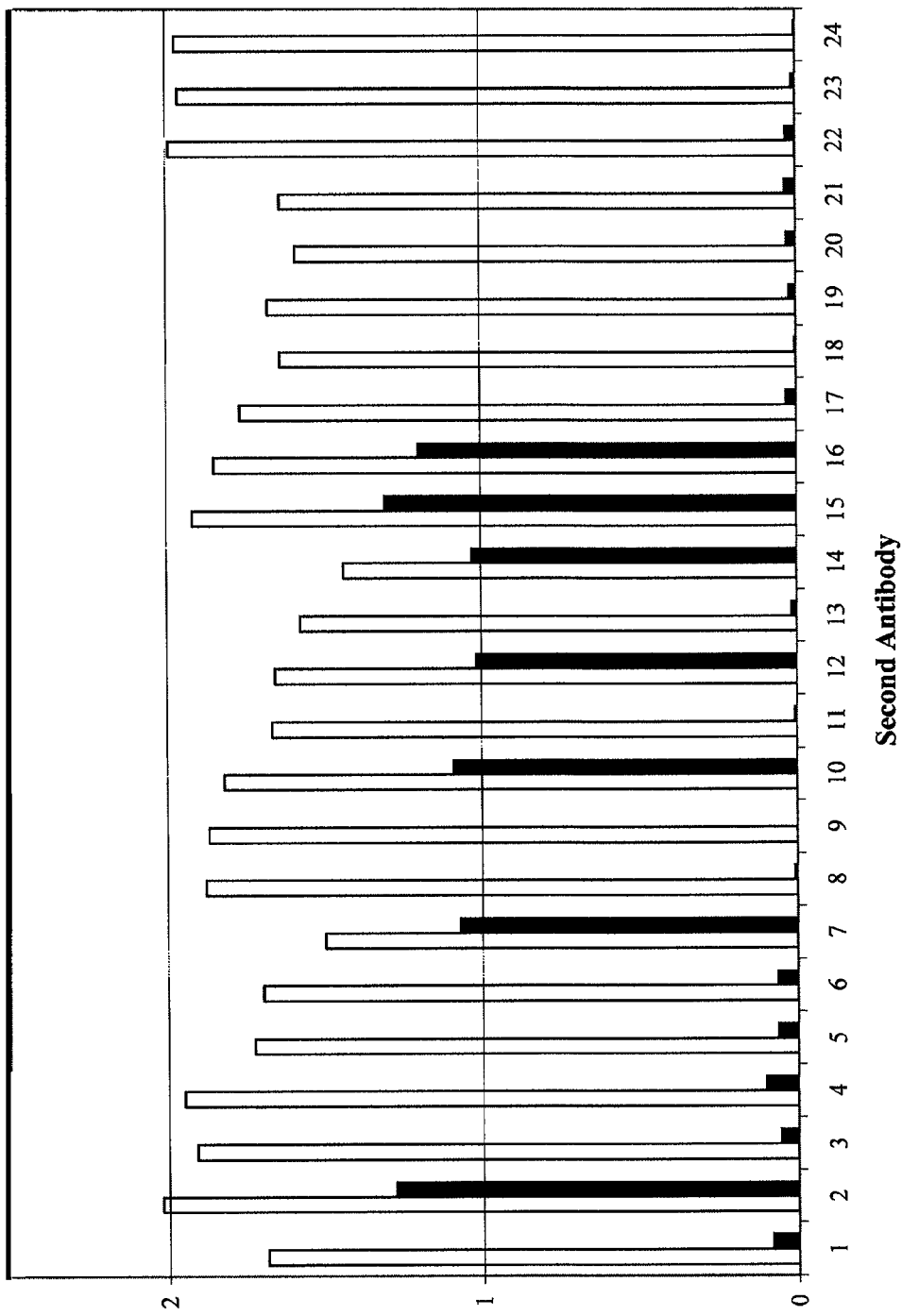

This application is a divisional of U.S. application Ser. No. 11/906,517, filed on Oct. 2, 2007, now issued as U.S. Pat. No. 7,605,237, which claims the benefit under 35 USC §119(e) of U.S. Provisional Appl. No. 60/848,694 filed on Oct. 2, 2006, and U.S. Provisional Appl. No. 60/957,738 filed on Aug. 24, 2007, which applications are herein specifically incorporated by reference in their entireties.

BACKGROUND

Interleukin-4 (IL-4, also known as B cell stimulating factor or BSF-1) was originally characterized by its ability to stimulate the proliferation of B cells in response to low concentrations of antibodies directed to surface immunoglobulin. IL-4 has been shown to possess a broad spectrum of biological activities, including growth stimulation of T cells, mast cells, granulocytes, megakaryocytes and erythrocytes. IL-4 induces the expression of class II major histocompatibility complex molecules in resting B cells, and enhances the secretion of IgE and IgG1 isotypes by stimulated B cells.

The biological activities of IL-4 are mediated by specific cell surface receptors for IL-4. Human IL-4 receptor alpha (hIL-4R) (SEQ ID NO:1) is described in, for example, U.S. Pat. Nos. 5,599,905, 5,767,065, and 5,840,869. Antibodies to hIL-4R are described in U.S. Pat. Nos. 5,717,072 and 7,186,809.

Methods to produce antibodies useful as human therapeutics include generating chimeric antibodies and humanized antibodies (see, for example, U.S. Pat. No. 6,949,245). See, for example, WO 94/02602 (Abgenix) and U.S. Pat. No. 6,596,541 (Regeneron Pharmaceuticals) (both of which publications are herein specifically incorporated by reference) describing methods of generating nonhuman transgenic mice capable of producing human antibodies.

Methods for using antibodies to hIL-4R are described in U.S. Pat. Nos. 5,714,146; 5,985,280; and 6,716,587.

BRIEF SUMMARY OF THE INVENTION

In a first aspect, the invention provides human antibodies, preferably recombinant human antibodies, that specifically bind human interleukin-4 receptor (hIL-4R). The human antibodies are characterized by binding to hIL-4R with high affinity and by the ability to neutralize hIL-4 activity. In specific embodiments, the human antibodies are capable of blocking hIL-13/hIL-13R1 complex binding to hIL-4R, and thus inhibit signaling by hIL-13. The antibodies can be full-length (for example, an IgG1 or IgG4 antibody) or may comprise only an antigen-binding portion (for example, a Fab, F(ab')$_2$ or scFv fragment), and may be modified to effect functionality, e.g., to eliminate residual effector functions (Reddy et al. (2000) J. Immunol. 164:1925-1933).

In one embodiment, the invention provides an antibody or antigen-binding fragment thereof, that specifically binds hIL-4R (SEQ ID NO:1) with a $K_D$ of about 200 pM or less, as measured by surface plasmon resonance. In a more specific embodiment, the antibody or antigen-binding portion thereof exhibits a $K_D$ of less than about 150 pM, or less than about 50 pM, or less than about 20 pM. In various embodiments, the antibody or antigen-binding fragment blocks hIL-4 activity with an $IC_{50}$ of about 200 pM or less, as measured by luciferase bioassay. In more specific embodiments, the antibody or antigen-binding fragment exhibits an $IC_{50}$ of about 150 pM or less, or about 100 pM or less, or even about 50 pM or less as measured by STAT6 luciferase bioassay. In various embodiments, the antibody or antigen-binding fragment blocks hIL-13 activity with an $IC_{50}$ of about 100 pM or less, as measured by STAT6 luciferase bioassay. In more specific embodiments, the antibody or antigen-binding fragment exhibits an $IC_{50}$ of about 75 pM or less, or about 50 pM or less, or even about 20 pM or less.

In a second aspect, the antibody of the invention comprises a heavy chain variable region (HCVR) selected from the group consisting of SEQ ID NO:3, 19, 35, 51, 67, 83, 99, 115, 131, 147, 163, 179, 195, 211, 227, 243, 259, 275, 291, 307, 323, 339, 355, 371, 387, 391, 395, 399, 403, 407, 411, 415, 419, 423, 427, 431, 435, 439, 443, 447, 451, 455, 459, 463, 467, 471, 475, 479, 483, 487, 491, 495, 499, 503, 507, 511, 515, 519, 523, 527, 531, 535, 539, 543, 547, 551, 555, 559, 563, 567, 571, 575, 579 and 581, or a substantially similar sequence thereof.

In a third aspect, the antibody of the invention comprises a light chain variable region (LCVR) selected from the group consisting of SEQ ID NO:11, 27, 43, 59, 75, 91, 107, 123, 130, 155, 171, 187, 203, 219, 235, 251, 267, 283, 299, 315, 331, 347, 363, 379, 389, 393, 397, 401, 405, 409, 413, 417, 421, 425, 429, 433, 437, 441, 445, 449, 453, 457, 461, 465, 469, 473, 477, 481, 485, 489, 493, 497, 501, 505, 509, 513, 517, 521, 625, 529, 533, 537, 541, 545, 549, 553, 557, 561, 565, 569, 573, and 577, or a substantially similar sequence thereof.

In one embodiment, the antibody of the invention comprises a HCVR and a LCVR (HCVR/LCVR) selected from the group consisting of SEQ ID NO: 3/11, 19/27, 35/43, 51/59, 67/75, 83/91, 99/107, 115/123, 131/139, 147/155, 163/171, 179/187, 195/203, 211/219, 227/235, 243/251, 259/267, 275/283, 291/299, 307/315, 323/331, 339/347, 355/363, 371/379, 387/389, 391/393, 395/397, 399/401, 403/405, 407/409, 411/413, 415/417, 419/421, 423/425, 427/429, 431/433, 435/437, 439/441, 443/445, 447/449, 451/453, 455/457, 459/461, 463/465, 467/469, 471/473, 475/477, 479/481, 483/485, 487/489, 491/493, 495/497, 499/501, 503/505, 507/509, 511/513, 515/517, 519/521, 523/525, 527/529, 531/533, 535/537, 539/541, 543/545, 547/549, 551.553, 555/557, 559/561, 563/565, 567/569, 571/573, 575/577, 579/59 and 581/59. In a preferred embodiment, the antibody or antibody fragment comprise HCVR/LCVR selected from SEQ ID NO: 51/59, 259/267, 275/283, 291/299, 579/59 or 581/59.

In a fourth aspect, the invention provides nucleic acid molecules encoding an HCVR, wherein the nucleic acid molecule is a nucleotide sequence selected from the group consisting of SEQ ID NO:2, 18, 34, 50, 66, 82, 98, 114, 130, 146, 162, 178, 194, 210, 226, 242, 258, 274, 290, 306, 322, 338, 354, 370, 386, 390, 394, 398, 402, 406, 410, 414, 418, 422, 426, 430, 434, 438, 442, 446, 450, 454, 458, 462, 466, 470, 474, 478, 482, 486, 490, 494, 498, 502, 506, 510, 514, 518, 522, 526, 530, 534, 538, 542, 546, 550, 554, 558, 562, 566, 570, 574, 578 and 580, or a substantially identical sequence having at least 95% homology thereof.

In a fifth aspect, the invention provides nucleic acid molecules encoding a LCVR, wherein the nucleic acid molecule is a sequence selected from the group consisting of SEQ ID NO:10, 26, 42, 58, 74, 90, 106, 122, 129, 154, 170, 186, 202, 218, 234, 250, 266, 282, 298, 314, 330, 346, 362, 378, 388, 392, 396, 400, 404, 408, 412, 416, 420, 424, 428, 432, 436, 440, 444, 448, 452, 456, 460, 464, 468, 472, 476, 480, 484, 488, 492, 496, 500, 504, 508, 512, 516, 520, 524, 528, 532, 536, 540, 544, 548, 552, 556, 560, 564, 568, 572, and 576, or a substantially identical sequence having at least 95% homology thereof.

In one embodiment, the antibody of the invention comprises a HCVR and LCVR encoded by a nucleotide sequence pairs selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/388, 390/392, 394/396, 398/400, 402/404, 406/408, 410/412, 414/416, 418/420, 422/424, 426/428, 430/432, 434/436, 438/440, 442/444, 446/448, 450/452, 454/456, 458/460, 462/464, 466/468, 470/472, 474/476, 478/480, 482/484, 486/488, 490/492, 494/496, 498/500, 502/504, 506/508, 510/512, 514/516, 518/520, 522/524, 526/528, 530/532, 534/536, 538/540, 542/544, 546/548, 550/552, 554/556, 558/560, 562/564, 566/568, 570/572, 574/576, 578/59 and 580/59. In a preferred embodiment, the antibody or antibody fragment comprise HCVR/LCVR encoded by nucleotide sequences selected from SEQ ID NO: 50/58, 258/266, 274/282, 290/298, 578/58 or 580/58.

In a sixth aspect, the invention features an antibody or antigen-binding fragment of an antibody that specifically binds hIL-4R, comprising three heavy chain and three light chain complementary determining regions (CDR), wherein
the heavy chain CDR1 comprises an amino acid sequence of the formula $X^1—X^2—X^3—X^4—X^5—X^6—X^7—X^8$ (SEQ ID NO:582), wherein $X^1$=Gly; $X^2$=Tyr or Phe; $X^3$=Thr or I; $X^4$=Phe; $X^5$=Asn or Arg; $X^6$=Ser; $X^7$=Tyr; and $X^8$=Gly;
the heavy chain CDR2 comprises an amino acid sequence of the formula $X^1—X^2—X^3—X^4—X^5—X^6—X^7—X^8$ (SEQ ID NO:583), wherein $X^1$=Ile, $X^2$=Ser or Arg, $X^3$=Thr or Tyr, $X^4$=Tyr or Asp, $X^5$=Asn or Gly, $X^6$=Gly or Ser, $X^7$=Lys or Asn, and $X^8$=Thr;
the heavy chain CDR3 comprises an amino acid sequence of the formula $X^1—X^2—X^3—X^4—X^5—X^6—X^7—X^8—X^9—X^{10}—X^{11}—X^{12}—X^{13}—X^{14}—X^{15}—X^{16}—X^{17}—X^{18}—X^{19}—X^{20}—X^{21}$ (SEQ ID NO:584) wherein $X^1$=Ala or Val, $X^2$=Arg or Lys, $X^3$=Asp or Glu, $X^4$=Gly or Glu, $X^5$=Ala or Arg, $X^6$=Arg or Ser, $X^7$=Ile or Gly, $X^8$=Val or Ser, $X^9$=Val or Trp, $X^{10}$=Ala or Phe, $X^{11}$=Gly or Asp, $X^{12}$=Thr or Pro, $X^{13}$=Thr or absent, $X^{14}$=Pro or absent, $X^{15}$=Tyr or absent, $X^{16}$=Tyr or absent, $X^{17}$=Tyr or absent, $X^{18}$=Gly or absent, $X^{19}$=Met or absent, $X^{20}$=Asp or absent, and $X^{21}$=Val or absent;
the light chain CDR1 comprises an amino acid sequence of the formula $X^1—X^2—X^3—X^4—X^5—X^6$ (SEQ ID NO:585) wherein $X^1$=Gln, $X^2$=Asp or Ala, $X^3$=Ile, $X^4$=Ser or Asn, $X^5$=Asn or Ile, and $X^6$=Trp or Phe;
the light chain CDR2 comprises an amino acid sequence of the formula $X^1—X^2—X^3$ (SEQ ID NO:586) wherein $X^1$=Ala or Val, $X^2$=Ala or Thr, and $X^3$=Ser; and
the light chain CDR3 comprises an amino acid sequence of the formula $X^1—X^2—X^3—X^4—X^5—X^6—X^7—X^8—X^9$ (SEQ ID NO:587) wherein $X^1$=Gln, $X^2$=Gln, $X^3$=Ala or Tyr, $X^4$=Asn, $X^5$=Ser, $X^6$=Phe or His, $X^7$=Pro, $X^8$=Ile or Trp, and $X^9$=Thr.

In a seventh aspect, the invention provides an antibody or antigen-binding fragment comprising a heavy chain CDR3 and a light chain CDR3, wherein the heavy chain CDR3 domain selected from the group consisting of SEQ ID NO:9, 25, 41, 57, 73, 89, 105, 121, 137, 153, 169, 185, 201, 217, 233, 249, 265, 281, 297, 313, 329, 345, 361 and 377; and the light chain CDR3 domain selected from the group consisting of SEQ ID NO:17, 33, 49, 65, 81, 97, 113, 129, 145, 161, 177, 193, 209, 225, 241, 257, 273, 289, 305, 321, 337, 353, 369 and 385. In a preferred embodiment, the heavy chain and light chain CDR3s are selected from the sequence pairs SEQ ID NO:57 and 65; 265 and 273; 281 and 289; and 297 and 305.

In a further embodiment, the invention features a human antibody or antibody fragment comprising a heavy chain CDR1 domain selected from the group consisting of SEQ ID NO:5, 21, 37, 53, 69, 85, 101, 117, 133, 149, 165, 181, 197, 213, 229, 245, 261, 277, 293, 309, 325, 341, 357 and 373, or a substantially similar sequence thereof; a heavy chain CDR2 domain selected from the group consisting of SEQ ID NO: 7, 23, 39, 55, 71, 87, 103, 119, 135, 151, 167, 183, 199, 215, 231, 247, 263, 279, 295, 311, 327, 343, 359 and 375, or a substantially similar sequence thereof; a heavy chain CDR3 domain selected from the group consisting of SEQ ID NO:9, 25, 41, 57, 73, 89, 105, 121, 137, 153, 169, 185, 201, 217, 233, 249, 265, 281, 297, 313, 329, 345, 361 and 377, or a substantially similar sequence thereof; a light chain CDR1 domain selected from the group consisting of SEQ ID NO:13, 29, 45, 61, 77, 93, 109, 125, 141, 157, 173, 189, 205, 221, 237, 253, 269, 285, 301, 317, 333, 349, 365 and 381, or a substantially similar sequence thereof; a light chain CDR2 domain selected from the group consisting of SEQ ID NO:15, 31, 47, 63, 79, 95, 111, 127, 143, 159, 175, 191, 207, 223, 239, 255, 271, 287, 303, 319, 335, 351, 367 and 383, or a substantially similar sequence thereof; and a light chain CDR3 domain selected from the group consisting of SEQ ID NO:17, 33, 49, 65, 81, 97, 113, 129, 145, 161, 177, 193, 209, 225, 241, 257, 273, 289, 305, 321, 337, 353, 369 and 385, or a substantially similar sequences thereof. in a preferred embodiment, the antibody or antigen-binding fragment comprise heavy chain CDRs SEQ ID NO:53, 55, 57 and light chain CDRs SEQ ID NO:61, 63, 65; heavy chain CDRs SEQ ID NO: 261, 263, 265 and light chain CDRs SEQ ID NO:269, 271, 273; heavy chain CDRs SEQ ID NO: 277, 279, 281 and light chain CDRs SEQ ID NO:285, 287, 289; and heavy chain CDRs SEQ ID NO: 293, 295, 297 and light chain CDRs SEQ ID NO:301, 303, 305.

In a eighth aspect, the invention provides an antibody or antigen-binding fragment comprising three CDRs from a HCVR and three CDRs from a LCVR, wherein the HCVR/LCVR are selected from the group consisting of 51/59, 579/59, 581/59, 259/267, 275/283, and 291/299.

In one embodiment, the invention features a human antibody or antibody fragment comprising a heavy chain and a light chain CDR3, wherein the heavy chain CDR3 is encoded by a nucleotide sequence selected from the group consisting of SEQ ID NO: 8, 24, 40, 56, 72, 88, 104, 120, 136, 152, 168, 184, 200, 216, 232, 248, 264, 280, 296, 312, 328, 344, 360 and 376; and a light chain CDR3 is encoded by a nucleotide sequence selected from the group consisting of SEQ ID NO: 16, 32, 48, 64, 80, 96, 112, 128, 144, 160, 176, 192, 208, 224, 240, 256, 272, 288, 304, 320, 336, 352, 368 and 384.

In a further embodiment, the invention features a human antibody or antibody fragment comprising a heavy chain CDR1 domain encoded by a nucleotide sequence selected from the group consisting of SEQ ID NO: 4, 20, 36, 52, 68, 84, 100, 116, 132, 148, 164, 180, 196, 212, 228, 244, 260, 276, 292, 308, 324, 340, 356 and 372, or a substantially identical sequence having at least 95% homology thereof; a heavy chain CDR2 domain encoded by a nucleotide sequence selected from the group consisting of SEQ ID NO: 6, 22, 38, 54, 70, 86, 102, 118, 134, 150, 166, 182, 198, 214, 230, 246, 262, 278, 294, 310, 326, 342, 358 and 374, or a substantially identical sequence having at least 95% homology thereof; a heavy chain CDR3 domain encoded by a nucleotide sequence selected from the group consisting of SEQ ID NO: 8, 24, 40, 56, 72, 88, 104, 120, 136, 152, 168, 184, 200, 216, 232, 248, 264, 280, 296, 312, 328, 344, 360 and 376, or a substantially similar sequence having at least 95% homology thereof; a light chain CDR1 domain encoded by a nucleotide sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, and 380, or a substantially similar sequence having at least 95% homology thereof; a light chain CDR2 domain encoded by a nucleotide sequence selected from the group consisting of SEQ ID NO: 14, 30, 46, 62, 78, 94, 110, 126, 142, 158, 174, 190, 206, 222, 238, 254, 270, 286, 302, 318, 334, 350, 366 and 382, or a substantially similar sequence having at least 95% homology thereof; and a light chain CDR3 domain encoded by a nucleotide sequence selected from the group consisting of SEQ ID NO: 16, 32, 48, 64, 80, 96, 112, 128, 144, 160, 176, 192, 208, 224, 240, 256, 272, 288, 304, 320, 336, 352, 368 and 384, or a substantially similar sequence having at least 95% homology thereof. In a preferred embodiment, the antibody or antigen-binding fragment comprise heavy chain CDRs encoded by nucleotide sequences SEQ ID NO:52, 54, 56 and light chain CDRs encoded by nucleotide sequences SEQ ID NO:60, 62, 64; heavy chain CDRs encoded by nucleotide sequences SEQ ID NO: 260, 262, 264 and light chain CDRs encoded by nucleotide sequences SEQ ID NO:268, 270, 272; heavy chain CDRs encoded by nucleotide sequences SEQ ID NO: 276, 278, 280 and light chain CDRs encoded by nucleotide sequences SEQ ID NO:284, 286, 288; and heavy chain CDRs encoded by nucleotide sequences SEQ ID NO: 292, 294, 296 and light chain CDRs encoded by nucleotide sequences SEQ ID NO:300, 302, 304.

The invention encompasses anti-hIL-4R antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of a galactosylation can be made in order to modify complement dependent cytotoxicity (CDC).

In a ninth aspect, the invention provides recombinant expression vectors carrying the nucleic acid molecules of the invention, and host cells into which such vectors have been included, as are methods of making the antibodies or antigen-binding fragments of the invention obtained by culturing the host cells of the invention. The host cell may be a prokaryotic or eukaryotic cell, preferably the host cell is an *E. coli* cell or a mammalian cell, such as a CHO cell.

In a tenth aspect, the invention features a composition comprising a recombinant human antibody that specifically binds hIL-4R and an acceptable carrier.

In an eleventh aspect, the invention features methods for inhibiting hIL-4 activity using an antibody, or antigen-binding portion thereof, of the invention. In specific embodiments, the antibodies of the invention also block hIL-13/hIL-13R1 complex binding to hIL-4R. In one embodiment, the method comprises contacting hIL-4R with the antibody of the invention, or antigen-binding portion thereof, such that hIL-4 or hIL-4/hIL-13 activity is inhibited. In another embodiment, the method comprises administering an antibody of the invention, or antigen-binding portion thereof, to a human subject suffering from a disorder that is ameliorated by inhibition of hIL-4 or hIL-4/hIL-13 activity. The disorder treated is any disease or condition that is improved, ameliorated, inhibited or prevented by removal, inhibition or reduction of hIL-4 or hIL-4/hIL-13 activity.

IL-4 related disorders which are treated by the antibodies or antibody fragments of the invention include, for example, arthritis (including septic arthritis), herpetiformis, chronic idiopathic urticaria, scleroderma, hypertrophic scarring, Whipple's Disease, benign prostate hyperplasia, lung disorders, such as mild, moderate or severe asthma, inflammatory disorders such as inflammatory bowel disease, allergic reactions, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, and nephrosis.

Other objects and advantages will become apparent from a review of the ensuing detailed description.

BRIEF DESCRIPTION OF FIGS.

FIG. 1(A-C). Antibody binding profile assessment generated with OCTET™-based sequential binding assay. FIG. 1(A) is a bar graph showing results obtained when the first antibody exposed to bound antigen is the control antibody. FIG. 1(B) the first antibody exposed to bound antigen is VAB16F3-1. FIG. 1(C) the first antibody exposed to bound antigen is VAK5H4-4. Second antibody: 1=control; 2=VX4E7-9; 3=VX3F7-6; 4=VAB16G-1; 5=VAB16F3-1; 6=VAB15C8-17; 7=VAB11G8-1; 8=VAB10C1-5; 9=VAB10G8-19; 10=VAB8G10-1; 11=VAB7B9-3; 12=VAB6C10-14; 13=VAB5C5-11; 14=VAB3B4-10; 15=VAB4D5-3; 16=VAB1H1-2; 17=VAK5H4-4; 18=VAK7G8-5; 19=VAK8G11-13; 20=VAK9C6-11; 21=VAK10G6-7; 22=VAK11D4-1; 23=VAK12B11-9; and 24=VAK10G12-5. Open bars show binding level of the first antibody, filled bars show additional binding by a second antibody.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Definitions

The term "human IL4R" (hIL-4R), as used herein, is intended to refer to a human cytokine receptor that specifically binds interleukin-4 (IL-4), IL-4Rα (SEQ ID NO:1). The term "human interleukin-13" (hIL-13) refers to a cytokine that specifically binds IL-13 receptor, and "hIL-13/hIL-13R1 complex" refers to the complex formed by hIL-13 binding to hIL-13R1 complex, which complex binds hIL-4 receptor to initiate biological activity.

The term "antibody", as used herein, is intended to refer to immunoglobulin molecules comprising four polypeptide chains, two heavy (H) chains and two light (L) chains interconnected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion" or "antibody fragment"), as used herein, refers to one or more fragments of an antibody that retain the ability to specifically bind to an antigen (e.g., hIL-4R). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL1 and CH1 domains; (ii) a F(ab')$_2$ fragment, a bivalent fragment comprising two F(ab)' fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain; and (vi) an isolated complementary determining region (CDR). Furthermore, although the two domains of the Fv fragment, VL and VH, are coded for by separate genes, they can be joined, using recombinant methods, by a synthetic linker that enables them to be made as a single contiguous chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883. Such single chain antibodies are also intended to be encompassed within the term "antigen-binding portion" of an antibody. Other forms of single chain antibodies, such as diabodies, are also encompassed (see e.g., Holliger et al. (1993) Proc. Natl. Acad Sci. USA 90:6444-6448).

A "neutralizing" or "blocking" antibody, as used herein, is intended to refer to an antibody whose binding to hIL-4R results in inhibition of the biological activity of hIL-4 and/or hIL-13. This inhibition of the biological activity of hIL-4 and/or IL-13 can be assessed by measuring one or more indicators of hIL-4 and/or hIL-13 biological activity known to the art, such as hIL-4- and/or IL-13-induced cellular activation and hIL-4 binding to hIL-4R (see examples below).

A "CDR" or complementary determining region is a region of hypervariability interspersed within regions that are more conserved, termed "framework regions" (FR). In different embodiments of the anti-hIL-4R antibody or fragment of the invention, the FRs may be identical to the human germline sequences, or may be naturally or artificially modified.

The term "surface plasmon resonance", as used herein, refers to an optical phenomenon that allows for the analysis of real-time interactions by detection of alterations in protein concentrations within a biosensor matrix, for example using the BIAcore™ system (Pharmacia Biosensor AB).

The term "epitope" is an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sufonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each of which is herein incorporated by reference.

Preparation of Human Antibodies

Methods for generating human antibodies include, for example, VelocImmune™ (Regeneron Pharmaceuticals), XenoMouse™ technology (Green et al. (1994) Nature Genetics 7:13-21; Abgenix), the "minilocus" approach, and phage display (and see, for example, U.S. Pat. No. 5,545,807, U.S. Pat. No. 6,787,637). The VelocImmune™ technology (U.S. Pat. No. 6,596,541) encompasses a method of generating a high specificity fully human antibody to a select antigen.

Rodents can be immunized by any method known in the art (see, for example, Harlow and Lane (1988) supra; Malik and Lillehoj (1994) Antibody techniques, Academic Press, CA). In a preferred embodiment, hIL-4R antigen is administered directly to mice that comprise DNA loci encoding both a human Ig heavy chain variable region and a Kappa light chain variable region (VelocImmune™, Regeneron Pharmaceuticals, Inc.; U.S. Pat. No. 6,596,541), with an adjuvant to stimulate the immune response, for example, complete and incomplete Freund's adjuvant, MPL+TDM adjuvant system (Sigma), or RIBI (muramyl dipeptides) (see O'Hagan (2000) Vaccine Adjuvant, Human Press, NJ). An adjuvant can prevent rapid dispersal of polypeptide by sequestering the antigen in a local depot, and may contain factors that can stimulate host immune response. VelocImmune™ technology involves generating a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In a specific embodiment, the cell is a CHO cell.

Antibodies may be therapeutically useful in blocking a ligand-receptor interaction or inhibiting receptor component interaction, rather than by killing cells through fixation of complement (complement-dependent cytotoxicity) (CDC) and participation antibody-dependent cell-mediated cytotoxicity (ADCC). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

Human immunoglobulins can exist in two forms that are associated with hinge heterogeneity. In one form, an immunoglobulin molecule comprises a stable four-chain construct of approximately 150-160 kDa in which the dimers are held together by an interchain heavy chain disulfide bond. In a second form, the dimers are not linked via interchain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. In fact, a single amino acid substitution in the hinge region of the human IgG4 hinge can significantly reduce the appearance of the second form (Angal et al. (1993) Molecular Immunology 30: 105) to levels typically observed using a human IgG1 hinge. The instant invention encompasses antibodies having one or more mutations in the hinge, CH2 or CH3 region that may be desirable, for example, in production, to improve the yield of the desired antibody form.

Antibodies of the invention are preferably prepared with the use of VelocImmune™ technology. A transgenic mouse in which the endogenous immunoglobulin heavy and light chain variable regions are replaced with the corresponding human variable regions is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable regions of the light and heavy chains may be isolated directly from antigen-specific lymphocytes.

In one embodiment, the transgenic mouse comprises up to 18 functional human variable heavy chain genes and 12 functional human variable kappa light chain genes. In another embodiment, the transgenic mouse comprises up to 39 human variable heavy chain genes and 30 human variable kappa light chain genes. In yet another embodiment, the transgenic mouse comprises up to 80 human variable heavy chain genes and 40 human variable kappa light chain genes.

In general, the antibodies of the instant invention possess very high affinities, typically possessing $K_D$s of from about $10^{-9}$ through about $10^{-12}$ M, when measured by binding to antigen either immobilized on a solid phase or measured in solution.

Initially, high affinity chimeric antibodies are isolated having a human variable region and a mouse constant region. As described below, the antibodies are characterized and selected for desirable characteristics, including binding affinity to hIL-4R, ability to block hIL-4 binding to hIL-4R, and/or selectivity for the human protein. The mouse constant regions are replaced with desired human constant regions to generate the fully human antibodies of the invention, for example wild-type or modified IgG4 or IgG1 (for example, SEQ ID NO:588, 589, 590). While the constant region selected may vary according to specific use, high affinity antigen-binding and target specificity characteristics reside in the variable region.

Epitope Mapping and Related Technologies

To screen for antibodies that bind to a particular epitope, a routine cross-blocking assay such as that described in *Antibodies: A Laboratory Manual* 1988 Cold Spring Harbor Laboratory, Harlow and Lane, eds. (herein specifically incorporated by reference in its entirety) can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science: 9:487-496).

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US Patent Application Publication No. 2004/0101920, herein specifically incorporated by reference in its entirety). Each category may reflect a unique epitope either distinctly different from, or partially overlapping with, an epitope represented by another category. This technology allows rapid filtering of genetically identical antibodies, such that characterization can be focused on genetically distinct antibodies. When applied to hybridoma screening, MAP may facilitate identification of rare hybridoma clones with desired characteristics. MAP may be used to sort the hIL-4R antibodies of the invention into groups of antibodies binding different epitopes.

Agents useful for altering the structure of the immobilized antigen are enzymes, such as, for example, proteolytic enzymes and chemical agents. The antigen protein may be immobilized on either biosensor chip surfaces or polystyrene beads. The latter can be processed with, for example, an assay such as a multiplex Luminex™ detection assay (Luminex Corp., TX). Because of the capacity of Luminex™ to handle multiplex analysis with up to 100 different types of beads, Luminex™ provides almost unlimited antigen surfaces with various modifications, resulting in improved resolution in antibody epitope profiling over a biosensor assay.

Therapeutic Administration and Formulations

Administration of therapeutic entities in accordance with the invention can be achieved with suitable carriers, excipients, and other agents that are incorporated into formulations to provide improved transfer, delivery, tolerance, and the like. A multitude of appropriate formulations can be found in the formulary known to all pharmaceutical chemists: Remington: The Science and Practice of Pharmacy (2003, 20th ed, Lippincott Williams & Wilkins). These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Powell et al. "Compendium of excipients for parenteral formulations" PDA (1998) J Pharm Sci Technol. 52:238-311 and the citations therein for additional information related to excipients and carriers well known to pharmaceutical chemists.

The therapeutic molecules of the invention may be administered to a patient in a manner appropriate to the indication, for example, parenterally, topically, or by inhalation. If injected, the antagonist can be administered, for example, via intra-articular, intravenous, intramuscular, intralesional, intraperitoneal or subcutaneous routes, by bolus injection, or continuous infusion. Localized administration at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Specific dosages and the frequency of administration may vary according to such factors as the route of administration, the nature and severity of the disease to be treated, whether the condition is acute or chronic, and the size and general condition of the patient. Appropriate dosages can be determined by procedures known in the pertinent art, e.g. in clinical trials that may involve dose escalation studies. The therapeutic molecules of the invention may be once, or repeatedly. In particular embodiments, the antibody or antibody fragment is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the therapeutic is administered until the patient manifests a medically relevant degree of improvement over baseline for the chosen indicator or indicators. The level of IL-4 may be monitored during and/or after treatment with the therapeutic molecule of the invention. Methods for measuring IL-4 serum levels are known in the art, for example by ELISA, etc.

Therapeutic Use and Combination Therapies

The antibodies and antibody fragments of the invention are useful for treating diseases and disorders which are improved, inhibited or ameliorated by reducing IL-4 activity. These disorders include those characterized by abnormal or excess expression of IL-4, or by an abnormal host response to IL-4 production. IL-4 related disorders which are treated by the antibodies or antibody fragments of the include, for example, arthritis (including septic arthritis), herpetiformis, chronic idiopathic urticaria, scleroderma, hypertrophic scarring, Whipple's Disease, benign prostate hyperplasia, pulmonary disorders such as asthma (mild, moderate or severe), inflammatory disorders such as inflammatory bowel disease, allergic reactions, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, atopic dermatatis, ulcerative colitis, fibrosis, and nephrosis (see U.S. Pat. No. 7,186,809, herein specifically incorporated by reference).

The invention encompasses combination therapies in which the anti-IL-4R antibody or antibody fragment is administered in combination with a second therapeutic agent. Co-administration and combination therapy are not limited to simultaneous administration, but include treatment regimens in which an anti-IL-4R antibody or antibody fragment is administered at least once during a course of treatment that involves administering at least one other therapeutic agent to the patient. A second therapeutic agent may be another IL-4 antagonist, such as another antibody/antibody fragment, or a soluble cytokine receptor, an IgE antagonist, an anti-asthma medication (corticosteroids, non-steroidal agents, beta agonists, leukotriene antagonists, xanthines, fluticasone, salmeterol, albuterol) which may be delivered by inhalation or other appropriate means. In a specific embodiment, the anti-IL-4R antibody or antibody fragment of the invention may be administered with an IL-1 antagonist, such as rilonacept, or an IL-13 antagonist. The second agent may include one or more leukotriene receptor antagonists to treat disorders such as allergic inflammatory diseases, e.g., asthma and allergies. Examples of leukotriene receptor antagonists include but are not limited to montelukast, pranlukast, and zafirlukast. The second agent may include a cytokine inhibitor such as one or more of a TNF (etanercept, ENBREL™), IL-9, IL-5 or IL-17 antagonist.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human IL-4 Receptor

Mice comprising DNA loci encoding both a human Ig heavy chain variable region and a kappa light chain variable region (VelocImmune™, Regeneron Pharmaceuticals, Inc.; U.S. Pat. No. 6,596,541) were immunized with human IL-4R (hIL-4R, SEQ ID NO:1). The hIL-4R was administered by direct injection of purified antigen in an adjuvant or indirectly by providing the DNA sequence of hIL-4R in a DNA plasmid that contains the hIL-4R gene and expresses hIL-4R using the host's cellular protein expression machinery to produce antigen polypeptide in vivo. To obtain optimal immune response, animals were subsequently boosted every 3-4 weeks and bleeds obtained 10 days after each boost for assessment of progression of anti-antigen response.

When the mice attained maximum immune response, antibody-expressing B cells were harvested and fused with mouse myeloma cells to form hybridomas. Functionally desirable monoclonal antibodies were selected by screening conditioned media of the hybridomas or transfected cells for specificity, antigen-binding affinity, and potency in blocking hIL-4 binding to hIL-4R (described below).

Selected antibodies that displayed desirable antigen binding affinity, potency, and/or ability to block hIL-4 binding to hIL-4R included (HCVR/LCVR): VX 4E7-9 (SEQ ID NO:3/11; 387/389; 391/393); VX 3F7-6 (SEQ ID NO:19/27; 395/397; 399/401); VAB 16G1-1 (SEQ ID NO:35/43; 403/405; 407/409); VAB 16F3-1 (SEQ ID NO:51/59, 411/413, 415/417, 579/59 and 581/59); VAB 15C8-17 (SEQ ID NO:67/75, 419/421, 423/425); VAB 13A1-6 (SEQ ID NO:83/91, 427/429, 431/433); VAB 11G8-1 (SEQ ID NO:99/107, 435/437, 439/441); VAB 10G8-19 (SEQ ID NO:115/123, 443/445, 447/449); VAB 10C1-5 (SEQ ID NO:131/139, 451/453, 455/457); VAB 8G10-1 (SEQ ID NO:147/155, 459/461, 463/465); VAB 7B9-3 (SEQ ID NO:163/171, 467/469, 471/473); VAB 6C10-14 (SEQ ID NO:179/187, 475/477, 479/481); VAB 5C5-11 (SEQ ID NO:195/203, 483/485, 487/489); VAB 3B4-10 (SEQ ID NO:211/219, 491/493, 495/497); VAB 4D5-3 (SEQ ID NO:227/235, 499/501, 503/505); VAB 1H1-2 (SEQ ID NO:243/251, 507/509, 511/513); VAK5H4-4 (SEQ ID NO:259/267, 515/517, 519/521); VAK7G8-5 (SEQ ID NO:275/283, 523/525, 527/529); VAK8G11-13 (SEQ ID NO:291/299, 531/533, 535/537); VAK9C6-11 (SEQ ID NO:307/315, 539/541, 543/545); VAK10G6-7 (SEQ ID NO:323/331, 547/549, 551/553); VAK11D4-1 (SEQ ID NO:339/347, 555/557, 559/561); VAK12B11-9 (SEQ ID NO:355/363, 563/565, 567/569); and VAK10G12-5 (SEQ ID NO:371/379, 571/573, 575/577).

Example 2

Antigen Binding Affinity Determination.

Binding affinity ($K_D$) of selected antibodies with respect to hIL-4R was determined using a real-time biosensor surface plasmon resonance assay (BIAcore™ 2000). Briefly, antibody was captured on a goat anti-mouse (GAM) IgG polyclonal antibody surface created through direct chemical coupling of the GAM IgG to a BIAcore™ chip to form a captured antibody surface. Various concentrations (ranging from 12.5 nM to 0.625 nM) of monomeric hIL-4R (R&D Systems) or dimeric hIL-4R-hFc were injected over the captured antibody surface. Binding of antigen to antibody and dissociation of the bound complex, were monitored in real time. Equilibrium dissociation constants ($K_D$) and dissociation rate constants were ascertained by performing kinetic analysis using BIA evaluation software. BIA evaluation software was also used to calculate the half-life of antigen/antibody complex dissociation ($T_{1/2}$). Results are shown in Table I. Control: a fully human anti-IL-4R antibody (U.S. Pat. No. 7,186,809; SEQ ID NOs:10 and 12). The results of the kinetic analyses revealed that the selected antibodies included high affinity antibodies that were capable of binding to dimeric receptor with $K_D$s under 1 nM. The binding affinity of anti-hIL-4R antibodies to either mouse or monkey (*Macaca fascicularis*) IL-4R was also tested. The selected antibodies (1) did not cross-react with mouse IL-4R; and (2) either failed to bind monkey IL-4R or bound monkey IL-4R with very low affinity.

TABLE 1

| Antibody | $K_D$ dimeric (pM) | $T_{1/2}$ dimeric (hr) | $K_D$ Monomeric (nM) | $T_{1/2}$ monomeric (min) |
|---|---|---|---|---|
| VX 4E7-9 | 111 | 19.1 | 1.43 | 48 |
| VX 3F7-6 | 654 | 2.7 | 3.91 | 16 |
| VAB 8G10-1 | 5,510 | 4.1 | 7.71 | 28 |
| VAB 7B9-3 | 52 | 6.1 | 1.01 | 13 |
| VAB 6C10-14 | 286 | 6.2 | 1.77 | 73 |
| VAB 5C5-11 | 27 | 7.7 | 0.13 | 47 |
| VAB 4D5-3 | 32 | 20.4 | 2.02 | 35 |
| VAB 3B4-10 | 53 | 20.4 | 0.59 | 102 |
| VAB 1H1-2 | 139 | 8.2 | 34.90 | 8 |
| VAB 16G1-1 | 38 | 7.3 | 0.93 | 15 |
| VAB 16F3-1 | 3 | 41 | 0.02 | 254 |
| VAB 15C8-17 | 45 | 3.6 | 0.82 | 15 |
| VAB 11G8-1 | 108 | 8.7 | 1.63 | 25 |
| VAB 10G8-19 | 52 | 2 | 11.40 | 2 |
| VAB 10C1-5 | 51 | 6.7 | 4.47 | 6 |
| VAK8G11-13 | 2 | 63 | 0.03 | 840 |
| VAK5H4-4 | 4 | 30 | 0.02 | 960 |
| VAK10G6-7 | 11 | 24 | 0.23 | 144 |
| VAK9C6-11 | 68 | 7 | 2.05 | 28 |
| VAK7G8-5 | 9 | 25 | 0.06 | 480 |
| VAK11D4-1 | 6 | 21 | 0.05 | 480 |
| VAK12B11-9 | 36 | 12 | 0.41 | 120 |
| VAK10G12-5 | 7 | 46 | 0.09 | 360 |
| Control | 71 | 2.1 | 1.23 | 16 |

Antibody-antigen binding affinity was also assessed using an ELISA-based solution competition assay. Briefly, antibodies (purified proteins at 1 or 3.3 ng/ml) were premixed with serial dilutions of antigen protein (monomeric or dimeric) ranging from 0 to 10 μg/ml. Solutions of the antibody and antigen mixture were then incubated for two to four hours at room temperature to reach binding equilibrium. Free antibody in the mixtures was then measured using a quantitative sandwich ELISA. Briefly, 96-well Maxisorp™ plates (VWR, West Chester, Pa.) were coated with 2 µg/ml hIL-4R-hFc protein in PBS overnight at 4° C. followed by blocking non-specific binding with BSA. The antibody-antigen mixture solutions were then transferred to the coated Maxisorb™ plates followed by a one-hour incubation. The plates were then washed with washing buffer and plate-bound antibodies were detected with an HRP-conjugated goat anti-mouse IgG polyclonal antibody reagent (Jackson ImmunoResearch) or an HRP-conjugated goat anti-human IgG polyclonal antibody reagent (Jackson ImmunoResearch) for control antibody and developed using calorimetric substrates such as BD OptEIA™ (BD Biosciences Pharmingen, San Diego, Calif.). After the reaction was stopped with 1 M phosphoric or sulfuric acid, absorbances at 450 nm were recorded and the data were analyzed using GraphPad™ Prism software. The dependency of the signals on the concentrations of antigen in solution was analyzed with a four parameter fit analysis and reported as $IC_{50}$, the antigen concentration required to achieve 50% reduction of the signal from the antibody samples without the presence of antigen in solution. The $IC_{50}$s were determined as described above and are summarized in Table 2. In a preferred embodiment, the antibody or antibody fragment of the invention exhibits an $IC_{50}$ for dimeric hIL-4R of about 20 pM or less, and an $IC_{50}$ for monomeric hIL-4R of about 150 pM or less, or about 100 pM or less, as measured by ELISA solution competition assay.

TABLE 2

| Antibody | $IC_{50}$ Dimeric hIL4R (pM) | $IC_{50}$ Monomeric hIL4R (pM) |
|---|---|---|
| VX 4E7-9 | 94 | 175 |
| VX 3F7-6 | 184 | 2,900 |
| VAB 8G10-1 | 85 | 517 |
| VAB 7B9-3 | 7 | 2,980 |
| VAB 6C10-14 | 203 | 489 |
| VAB 5C5-11 | 6 | 5,220 |
| VAB 4D5-3 | 35 | 285 |
| VAB 3B4-10 | 88 | 336 |
| VAB 1H1-2 | 70 | 779 |
| VAB 16G1-1 | 9 | 595 |
| VAB 16F3-1 | 5 | 7 |
| VAB 15C8-17 | 9 | 418 |
| VAB 11G8-1 | 76 | 473 |
| VAB 10G8-19 | 4 | 89 |
| VAB 10C1-5 | 12 | 12,900 |
| VAK 5H4-4 | 18 | 130 |
| VAK 7G8-5 | 18 | 92 |
| VAK 8G11-13 | 15 | 103 |
| VAK 9C6-11 | 46 | 1,400 |
| VAK 10G6-7 | 25 | 165 |
| VAK 11D4-1 | 23 | 109 |
| VAK 12B11-9 | 64 | 325 |
| VAK 10G12-5 | 41 | 169 |
| Control | 14 | 3,500 |

Example 3

Inhibition of hIL-4 and hIL-4R Interaction

The ability of the selected antibodies to block hIL-4 binding to hIL-4R were screened by BIAcore™ hIL-4 blocking assay and potency was measured by a quantitative hIL-4 blocking immunoassay as described below. Results are summarized in Table 3.

The ability of the antibodies to block hIL-4 binding to the hIL-4R receptor was determined using surface plasmon resonance. Purified hIL-4R-hFc molecules were captured by goat anti-human IgG polyclonal antibody immobilized on CM-5 to a density of 260 RU, to prepare a receptor-coated surface. Human IL-4 (0.25 ml at 50 nM) was then injected over the receptor-coated surface and the amount of bound hIL-4 was recorded (first injection of hIL-4). The bound hIL-4 was then removed with a pulse of 3 M $MgCl_2$ followed by conditioning buffer. Purified anti-hIL4R antibodies were then injected over the receptor surface followed by a second injection of hIL-4 at the same concentration (second injection of hIL-4).). The percent reduction in hIL-4 binding resulting from preformed antibody and receptor complex is reported in Table 3.

To further evaluate ability to block hIL-4 binding to hIL-4R, a quantitative immunoassay was performed. Briefly, solutions of 25 pM hIL-4R-Fc were premixed with antibody protein ranging from ~50 nM to 0 nM in serial dilutions, followed by a one hour incubation at room temperature. Concentration of free hIL-4R-Fc (no antibody bound) was determined using a hIL-4R-specific sandwich ELISA. Detection plates for hIL-4R were prepared by binding biotinylated hIL-4 (0.5 ug/ml) on streptavidin-coated 96-well plates. Pre-bound antibody-antigen samples were transferred to the hIL-4-coated detection plate. After a one-hour incubation at room temperature, the detection plate was washed and plate-bound hIL-4R-hFc was detected using HRP conjugated goat anti-hFc polyclonal antibodies and developed using colorimetric substrates such as BD OptEIA™ (BD Biosciences Pharmingen, San Diego, Calif.). After the reaction was stopped with 1 M phosphoric or sulfuric acid, absorbances at 450 nm were recorded and the data were analyzed using GraphPad™ Prism software. $IC_{50}$s were determined as the amount of antibody required to reduce 50% of IL-4R-hFc detectable to plate bound hIL-4. In a preferred embodiment, the antibody or antibody fragment of the invention exhibits an $IC_{50}$ for blocking 25 pM hIL-4R of less than about 50 pM, or less than about 40 pM, or less than about 30 pM, or less than about 20 pM, as measured by ELISA.

TABLE 3

| Antibody | % Inhibition (BIAcore ™) | $IC_{50}$ (ELISA pM) |
|---|---|---|
| VX 4E7-9 | 79 | 118 |
| VX 3F7-6 | 86 | 274 |
| VAB 8G10-1 | 74 | 244 |
| VAB 7B9-3 | 96 | 59 |
| VAB 6C10-14 | 79 | 441 |
| VAB 5C5-11 | 96 | 24 |
| VAB 4D5-3 | 82 | 240 |
| VAB 3B4-10 | 72 | 322 |
| VAB 1H1-2 | 78 | 146 |
| VAB 16G1-1 | 92 | 18 |
| VAB 16F3-1 | 97 | 19 |
| VAB 15C8-17 | 97 | 29 |
| VAB 11G8-1 | 77 | 240 |
| VAB 10G8-19 | 85 | 18 |
| VAB 10C1-5 | 93 | 34 |
| VAK 5H4-4 | 96 | 33 |
| VAK 7G8-5 | 95 | 27 |
| VAK 8G11-13 | 95 | 26 |
| VAK 9C6-11 | 96 | 67 |
| VAK 10G6-7 | 95 | 37 |
| VAK 11D4-1 | 95 | 35 |
| VAK 12B11-9 | 96 | 99 |
| VAK 10G12-5 | 94 | 59 |

Example 4

Neutralization of Biological Effect of hIL-4 In Vitro

The IL-4-mediated signal transduction pathway has been documented extensively in the literature (for example, see review of Hebenstreit et al. 2006 Cytokine Growth Factor Rev. 17(3):173-88, 2006). IL-4 can stimulate two receptor complexes, type I and type II. Type I receptor complexes are formed by the binding of IL-4 to IL-4R and the subsequent heterodimerization with the common gamma chain. Alternatively, IL4/IL4R complex can heterodimerize with the IL-13 receptor 1 to form type II receptor complexes. Both type I and type II complexes signal mainly through STAT6. Therefore, the ability of the selected antibodies to block signaling through STAT6 was assessed as described below.

A cell line with high sensitivity to hIL-4 and hIL-13 was established. HEK293 cells were stably transfected with human STAT6 and a STAT6 luciferase reporter plasmid, and was maintained in growth media (DMEM, 10% FBS, L-glutamine, penicillin, streptomycin). A robust IL-4 receptor-mediated response was achieved when 10 pM hIL-4 was added to the growth medium of the STAT6-transfected HEK293 cells. For bioassay of the hIL-4 response, cells were washed once in assay media (Optimem I (Gibco) plus 0.1% FBS) and plated at $1 \times 10^4$ cells/well (96 well plate) in 80 µl of assay media. Purified antibodies were serially diluted into assay media (final concentrations ranging from 20 nM to 0) and 10 µl of each of the test antibody was added to the cells along with 10 µl of hIL-4 (10 pM constant final concentration). Cells were then incubated at 37° C., 5% $CO_2$ for 6 hrs. The extent of cellular response was measured in a luciferase assay (Promega Biotech). Results are shown in Table 4.

Inhibition of IL-4-dependent biological activity in vitro was also confirmed using either a human erythroblast cell line, TF1, or a modified, II-13Rα overexpressing TF1 cell line (TF1/A12). In this bioassay, 20,000 cells were seeded in each well of a 96-well plate in RPMI 1640 medium containing 10% FBS, 2 mM L-glutamine, and penicillin and streptomycin. Twenty-five µl of purified antibodies ranging from 0 to 50 nM (final concentration) were added together with 25 µl of hIL-4 recombinant protein to a final concentration of either 50 pM for cell line TF1 or 20 pM for cell line TF1/A12. Cells were then allowed to grow for 3 days at 37° C. and final cell counts were measured using a CCK8 kit (Dojindo, Japan). Ability of antibody to block TF-1 cell growth is reported in Table 4 as the concentration of antibody required to achieve 50% reduction of cell proliferation.

TABLE 4

| Antibody | STAT6 Bioassay $IC_{50}$ (nM) | TF1 Bioassay $IC_{50}$ (nM) | TF1/A12 Bioassay $IC_{50}$ (nM) |
|---|---|---|---|
| VX 4E7-9 | 7.90 | | 10 |
| VX 3F7-6 | >10 | | >50 |
| VAB 8G10-1 | >10 | | >50 |
| VAB 7B9-3 | 3.40 | | 8.20 |
| VAB 6C10-14 | >10 | | 23 |
| VAB 5C5-11 | 0.14 | 0.21 | 0.37 |
| VAB 4D5-3 | 3.80 | | 21 |
| VAB 3B4-10 | >10 | | >50 |
| VAB 1H1-2 | >10 | | >50 |
| VAB 16G1-1 | 0.14 | 0.12 | 0.70 |
| VAB 16F3-1 | 0.032 | 0.046 | 0.067 |
| VAB 15C8-17 | 0.32 | 0.44 | 4.70 |
| VAB 11G8-1 | >10 | | >50 |
| VAB 10G8-19 | 1.80 | | 12.8 |
| VAB 10C1-5 | 1.90 | | 22.8 |
| VAK 5H4-4 | 0.132 | 0.150 | 0.182 |
| VAK 7G8-5 | 0.06 | 0.13 | |
| VAK 8G11-13 | 0.08 | 0.16 | |
| VAK 9C6-11 | 0.48 | 0.31 | |
| VAK 10G6-7 | 0.11 | 0.23 | |
| VAK 11D4-1 | 0.20 | 0.20 | |
| VAK 12B11-9 | 0.49 | 0.57 | |
| VAK 10G12-5 | 0.36 | 0.58 | |

Example 5

Neutralization of Biological Effect of hIL-13 In Vitro

Since IL-4R has been shown to be a modulator for IL-13 activity through its binding to IL-13/IL-13R complex, the selected antibodies were tested for their ability to block IL-13 activity in a modification of the HEK293 STAT6 luciferase assay described above, with the modification being replacement of 10 pM IL-4 with 40 pM hIL-13. The antibodies were also assessed for potency in blocking hIL-13 activity in the TF-1 cell line assay described above, with hIL-13 at 150 pM in the presence of 0-50 nM antibodies. Results are shown in Table 5.

TABLE 5

| Antibody | STAT6 Bioassay $IC_{50}$ (nM) | TF1 Bioassay $IC_{50}$ (nM) |
|---|---|---|
| VX 4E7-9 | 6.30 | |
| VX 3F7-6 | >10 | |
| VAB 8G10-1 | >10 | |
| VAB 7B9-3 | 1.10 | |
| VAB 6C10-14 | >10 | |
| VAB 5C5-11 | 0.06 | 0.82 |
| VAB 4D5-3 | 3.30 | |
| VAB 3B4-10 | 8.30 | |
| VAB 1H1-2 | >10 | |
| VAB 16G1-1 | 0.09 | 0.44 |
| VAB 16F3-1 | 0.018 | 0.079 |
| VAB 15C8-17 | 0.20 | 2.60 |
| VAB 11G8-1 | 8.80 | |
| VAB 10G8-19 | 0.97 | |
| VAB 10C1-5 | 1.00 | |
| VAK 5H4-4 | 0.084 | 0.240 |
| VAK 7G8-5 | 0.04 | 0.36 |
| VAK 8G11-13 | 0.06 | 0.42 |
| VAK 9C6-11 | 0.30 | 1.00 |
| VAK 10G6-7 | 0.07 | 0.46 |
| VAK 11D4-1 | 0.14 | 0.44 |
| VAK 12B11-9 | 0.37 | 1.60 |
| VAK 10G12-5 | 0.26 | 1.90 |

Example 6

Antibody Binding Profile Assessment

An antibody binding profile can be established by determining the effect that an antibody (bound to its antigen) can have on the ability of a panel of different antibodies to subsequent bind the same antigen. For example, the antigen can be immobilized on a support to form an antigen-coated surface, the antigen-coated surface can be saturated with the antibody, and then the antibody-saturated antigen-coated surface can be exposed to a panel of other antibodies. The extent of binding of the panel of other antibodies to the antibody-saturated antigen surface provides an antibody binding profile. OCTET™-based sequential binding assays were employed to generate an antibody binding profile. Briefly, a group of 24 strepavidin High Binding FA Biosensors (ForteBio, Inc., Menlo Park, Calif.) were first incubated with antigen, biotin-hIL-4R-hFc, at 2 µg/ml for 10 min at 30° C. to achieve saturation and the amount of bound antigen was measured as a change in thickness (nm) of the biological layer due to bound protein, which is directly measured by the wavelength shift. Biotin-hIL-4R-hFc-bound biosensors were then incubated with the first antibody (control antibody) at 50 µg/ml for 15 min at 30° C. to achieve saturation and the amount of bound control antibody was measured as a change in thickness (nm) of the biological layer. Each control antibody-bound sensor was then incubated with one of a panel of 24 different anti-hIL-4R antibodies (second antibody) at 50 µg/ml for 15 min at 30° C., and the amount of second antibody bound was measured as a change in thickness of the biological layer. The same assay was repeated using either VAB16F3-1 or VAK5H4-4 anti-hIL-4R antibody as the first antibody. Results are shown in FIG. 1A-C.

Selected anti-hIL-4R antibodies were also assessed by Western blot (data not shown). Briefly, hIL-4R monomer (200 ng per lane) and mfIL-4R His-tagged monomer (200 ng per lane) were electrophoresed on SDS-PAGE gels using both reducing and non-reducing sample buffer. Four separate gels were each transferred to a PVDF membrane and each membrane was exposed to one of four primary antibodies: anti-His mAb (Qiagen), VAB 16F3-1, VAK 5H4-4, or control anti-hIL-4R antibody, with either HRP-conjugated goat anti-mIgG or anti-hIgG (Pierce) as secondary antibody. All three anti-hIL-4R antibodies recognized the non-reduced form of hIL-4R. Only VAB 16F3-1 and VAK 5H4-4 detected the reduced form of hIL-4R. None of the anti-hIL-4R antibodies detected monkey IL-4R.

The invention claimed is:

1. A method of treating a disease or disorder which is improved, ameliorated or inhibited by removal, inhibition or reduction of human interleukin-4 (hIL-4) activity, said method comprising administering to a patient in need thereof an antibody or antigen-binding fragment thereof which specifically binds to a hIL-4 receptor, wherein said antibody comprises a heavy chain variable region (HCVR) comprising the three heavy chain CDRs (HCDR1, HCDR2 and HCDR3) from SEQ ID NO:581, and a light chain variable region (LCVR) comprising the three light chain CDRs (LCDR1, LCDR2 and LCDR3) from SEQ ID NO:417, wherein the disease or disorder is asthma.

2. The method of claim 1, wherein said HCVR comprises SEQ ID NO:581.

3. The method of claim 1, wherein said LCVR comprises SEQ ID NO:417.

4. The method of claim 1, wherein said HCVR comprises SEQ ID NO:581 and said LCVR comprises SEQ ID NO:417.

* * * * *

SEQUENCE LISTING

```
<160> NUMBER OF SEQ ID NOS: 590

<210> SEQ ID NO 1
<211> LENGTH: 207
<212> TYPE: PRT
<213> ORGANISM: homo sapiens

<400> SEQUENCE: 1

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205

<210> SEQ ID NO 2
<211> LENGTH: 351
<212> TYPE: DNA
<213> ORGANISM: Artificial Sequence
<220> FEATURE:
<223> OTHER INFORMATION: Synthetic
```

<400> SEQUENCE: 2

```
caggttcagc tggtgcagtc tggagctgag gtgaagaagc ctggggcctc agtgaaggtc    60
tcctgcaagg cttctggtta ccctttacc aactatggta tcagctgggt gcgacaggcc   120
cctggacaag ggcttgagtg gatgggatgg atcagcgttt acaatggtaa aacaaactat   180
gcacagaagc tccagggcag agtcaccatg accacagaca catccacgac cacagcctac   240
atggaaatga ggagcctgag atctgacgac acggccgttt attactgtgc gagaggtagt   300
ggctacgatt tggactactg gggccaggga accctggtct ccgtctcctc a            351
```

<210> SEQ ID NO 3
<211> LENGTH: 117
<212> TYPE: PRT
<213> ORGANISM: Artificial Sequence
<220> FEATURE:
<223> OTHER INFORMATION: Synthetic

<400> SEQUENCE: 3

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Gly Ile Ser Trp Val Arg Gln Ala Pro Gly Gln Gly Leu Glu Trp Met
         35                  40                  45

Gly Trp Ile Ser Val Tyr Asn Gly Lys Thr Asn Tyr Ala Gln Lys Leu
     50                  55                  60

Gln Gly Arg Val Thr Met Thr Thr Asp Thr Ser Thr Thr Thr Ala Tyr
 65                  70                  75                  80

Met Glu Met Arg Ser Leu Arg Ser Asp Asp Thr Ala Val Tyr Tyr Cys
                 85                  90                  95

Ala Arg Gly Ser Gly Tyr Asp Leu Asp Tyr Trp Gly Gln Gly Thr Leu
            100                 105                 110

Val Ser Val Ser Ser
        115

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4

```
ggttacacct ttaccaacta tggt                                            24
```

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Gly Tyr Thr Phe Thr Asn Tyr Gly
 1               5

<210> SEQ ID NO 6
<211> LENGTH: 24
<212> TYPE: DNA
<213> ORGANISM: Artificial Sequence
<220> FEATURE:

```
<223> OTHER INFORMATION: Synthetic

<400> SEQUENCE: 6
atcagcgttt acaatggtaa aaca                                        24

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Ile Ser Val Tyr Asn Gly Lys Thr
1               5

<210> SEQ ID NO 8
<211> LENGTH: 30
<212> TYPE: DNA
<213> ORGANISM: Artificial Sequence
<220> FEATURE:
<223> OTHER INFORMATION: Synthetic

<400> SEQUENCE: 8
gcgagaggta gtggctacga tttggactac                                  30

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Ala Arg Gly Ser Gly Tyr Asp Leu Asp Tyr
1               5                   10

<210> SEQ ID NO 10
<211> LENGTH: 321
<212> TYPE: DNA
<213> ORGANISM: Artificial Sequence
<220> FEATURE:
<223> OTHER INFORMATION: Synthetic

<400> SEQUENCE: 10
gccatccaga tgacccagtc tccatcctcc ctgtctgcat ctgtcggaga cagagtcacc    60
atcacttgcc gggcaagtca gggcattaga aatgctttag ctggtatca gcagaaacca   120 gggaaagccc ctaagctcct gatctatgct gcatccagtt tacaaagtgg ggtcccatca   180
aggttcagcg gcagtggatc tggcacagat ttcactctca ccttcagcag cctgcagcct   240
gaagattttg caacttatta ctgtctacaa gatttcaatt acccgtacac ttttggccag   300
gggaccaagc tggagatcaa a                                           321

<210> SEQ ID NO 11
<211> LENGTH: 107
<212> TYPE: PRT
<213> ORGANISM: Artificial Sequence
<220> FEATURE:
<223> OTHER INFORMATION: Synthetic

<400> SEQUENCE: 11

Ala Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Arg Asn Ala
             20                  25                  30

Leu Gly Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Phe Ser Ser Leu Gln Pro
65                  70                  75                  80

Glu Asp Phe Ala Thr Tyr Tyr Cys Leu Gln Asp Phe Asn Tyr Pro Tyr
                 85                  90                  95

Thr Phe Gly Gln Gly Thr Lys Leu Glu Ile Lys
            100                 105
```

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
cagggcatta gaaatgct                                           18

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

```
Gln Gly Ile Arg Asn Ala
 1               5
```

<210> SEQ ID NO 14
<211> LENGTH: 9
<212> TYPE: DNA
<213> ORGANISM: Artificial Sequence
<220> FEATURE:
<223> OTHER INFORMATION: Synthetic

<400> SEQUENCE: 14 gctgcatcc                                                      9

<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

```
Ala Ala Ser
 1
```

<210> SEQ ID NO 16
<211> LENGTH: 27
<212> TYPE: DNA
<213> ORGANISM: Artificial Sequence
<220> FEATURE:
<223> OTHER INFORMATION: Synthetic

<400> SEQUENCE: 16
ctacaagatt tcaattaccc gtacact                                 27

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Leu Gln Asp Phe Asn Tyr Pro Tyr Thr
1               5

<210> SEQ ID NO 18
<211> LENGTH: 384
<212> TYPE: DNA
<213> ORGANISM: Artificial Sequence
<220> FEATURE:
<223> OTHER INFORMATION: Synthetic

<400> SEQUENCE: 18

```
gaggtgcagc tggtggagtc tgggggaggc ttggtccagc ctgggggtc cctaagactc      60
tcctgtgcag cctctggatt cacctttagt tccttctgga tgacctgggt ccgccaggct    120
ccagggaagg ggctggagtg ggtggccaac ataaagcaag atggaagtga aaatactat    180
gtggactctg tgaagggccg attcaccatt tcccgagaca cgccaagaa ctcactgtat    240
ctgcaaatga acagcctgag agccgaggac acggctgttt attactgtgc gagagatccc    300
gggcgaacta tggttcgggg aggtataaga tattactatg gtatggacgt ctggggccaa    360
gggaccacgg tcaccgtctc ctca                                            384
```

<210> SEQ ID NO 19
<211> LENGTH: 128
<212> TYPE: PRT
<213> ORGANISM: Artificial Sequence
<220> FEATURE:
<223> OTHER INFORMATION: Synthetic

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Arg Thr Met Val Arg Gly Gly Ile Arg Tyr Tyr
            100                 105                 110

Tyr Gly Met Asp Val Trp Gly Gln Gly Thr Thr Val Thr Val Ser Ser
        115                 120                 125

<210> SEQ ID NO 20
<211> LENGTH: 24
<212> TYPE: DNA
<213> ORGANISM: Artificial Sequence
<220> FEATURE:
<223> OTHER INFORMATION: Synthetic

```
<400> SEQUENCE: 20
ggattcacct ttagttcctt ctgg                                              24

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Gly Phe Thr Phe Ser Ser Phe Trp
 1               5

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
ataaagcaag atggaagtga gaaa                                              24

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Ile Lys Gln Asp Gly Ser Glu Lys
 1               5

<210> SEQ ID NO 24
<211> LENGTH: 63
<212> TYPE: DNA
<213> ORGANISM: Artificial Sequence
<220> FEATURE:
<223> OTHER INFORMATION: Synthetic

<400> SEQUENCE: 24
gcgagagatc ccgggcgaac tatggttcgg ggaggtataa gatattacta tggtatggac       60
gtc                                                                     63

<210> SEQ ID NO 25
<211> LENGTH: 21
<212> TYPE: PRT
<213> ORGANISM: Artificial Sequence
<220> FEATURE:
<223> OTHER INFORMATION: Synthetic

<400> SEQUENCE: 25

Ala Arg Asp Pro Gly Arg Thr Met Val Arg Gly Gly Ile Arg Tyr Tyr
 1               5                  10                  15

Tyr Gly Met Asp Val
            20

<210> SEQ ID NO 26
<211> LENGTH: 321
<212> TYPE: DNA
<213> ORGANISM: Artificial Sequence
<220> FEATURE:
```

-continued

<223> OTHER INFORMATION: Synthetic

<400> SEQUENCE: 26

```
gacatccaga tgacccagtc tccatcttcc gtgtctgcat ctgtaggaga cagagtcacc    60
atcagttgtc gggcgagtca gggtgttagt agctggttag cctggtatca gcagaaacca   120
gggaacgccc ctaagctcct gatctctgct gcatccagta tacaaagtgg ggtcccatca   180
aggttcagcg gcagtggatc tgggacagat ttcactctca ccatcagcag cctgcagcct   240
gaagattttg caacttacta ttgtcaacag gctaacagtt ccctctcac tttcggcgga    300
gggaccaagg tggagatcaa a                                             321
```

<210> SEQ ID NO 27
<211> LENGTH: 107
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Gly Val Ser Ser Trp
            20                  25                  30

Leu Ala Trp Tyr Gln Gln Lys Pro Gly Asn Ala Pro Lys Leu Leu Ile
        35                  40                  45

Ser Ala Ala Ser Ser Ile Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28

```
cagggtgtta gtagctgg                                                  18
```

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Gln Gly Val Ser Ser Trp
1               5

<210> SEQ ID NO 30
<211> LENGTH: 9
<212> TYPE: DNA
<213> ORGANISM: Artificial Sequence
<220> FEATURE:
<223> OTHER INFORMATION: Synthetic

```
<400> SEQUENCE: 30 gctgcatcc                                                                    9

<210> SEQ ID NO 31
<211> LENGTH: 3
<212> TYPE: PRT
<213> ORGANISM: Artificial Sequence
<220> FEATURE:
<223> OTHER INFORMATION: Synthetic

<400> SEQUENCE: 31

Ala Ala Ser
 1

<210> SEQ ID NO 32
<211> LENGTH: 27
<212> TYPE: DNA
<213> ORGANISM: Artificial Sequence
<220> FEATURE:
<223> OTHER INFORMATION: Synthetic

<400> SEQUENCE: 32
caacaggcta acagtttccc tctcact                                               27

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Gln Gln Ala Asn Ser Phe Pro Leu Thr
 1               5

<210> SEQ ID NO 34
<211> LENGTH: 366
<212> TYPE: DNA
<213> ORGANISM: Artificial Sequence
<220> FEATURE:
<223> OTHER INFORMATION: Synthetic

<400> SEQUENCE: 34
gaggtgaagt tggcggagtc tgggggaggc ttggtccagc cggggggggtc cctgagactc          60 tcctgtgcag cctctggatt cacctttagt agccattgga tgaactgggt ccgccaggct         120
ccagggaagg ggctggagtg ggtggccaac ataaagcaag atggaagtga taaatactat         180
gtggactctg tgaagggccg attcaccatc tccagagaca acgccaagaa ctcactctat         240
ctgcaattga acagcctgat agccgaggac acggctgtgt attactgtgc gagagatcgg         300
ggggttagac cacctcgtgg ggcttttgat atctggggcc aagggacaat ggtcaccgtc         360
tcttca                                                                   366

<210> SEQ ID NO 35
<211> LENGTH: 122
<212> TYPE: PRT
<213> ORGANISM: Artificial Sequence
<220> FEATURE:
<223> OTHER INFORMATION: Synthetic

<400> SEQUENCE: 35

Glu Val Lys Leu Ala Glu Ser Gly Gly Gly Leu Val Gln Pro Gly Gly
 1               5                  10                  15
```

-continued

```
Ser Leu Arg Leu Ser Cys Ala Ala Ser Gly Phe Thr Phe Ser Ser His
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Ile Ala Glu Asp Thr Ala Val Tyr Tyr Cys
                85                  90                  95

Ala Arg Asp Arg Gly Val Arg Pro Arg Gly Ala Phe Asp Ile Trp
            100                 105                 110

Gly Gln Gly Thr Met Val Thr Val Ser Ser
            115                 120
```

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
ggattcacct ttagtagcca ttgg                                    24

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

```
Gly Phe Thr Phe Ser Ser His Trp
 1               5
```

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
ataaagcaag atggaagtga taaa                                    24

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

```
Ile Lys Gln Asp Gly Ser Asp Lys
 1               5
```

<210> SEQ ID NO 40
<211> LENGTH: 45
<212> TYPE: DNA
<213> ORGANISM: Artificial Sequence
<220> FEATURE:
<223> OTHER INFORMATION: Synthetic

<400> SEQUENCE: 40
gcgagagatc gggggttag accacctcgt ggggcttttg atatc    45

<210> SEQ ID NO 41
<211> LENGTH: 15
<212> TYPE: PRT
<213> ORGANISM: Artificial Sequence
<220> FEATURE:
<223> OTHER INFORMATION: Synthetic

<400> SEQUENCE: 41

Ala Arg Asp Arg Gly Val Arg Pro Pro Arg Gly Ala Phe Asp Ile
1               5                   10                  15

<210> SEQ ID NO 42
<211> LENGTH: 321
<212> TYPE: DNA
<213> ORGANISM: Artificial Sequence
<220> FEATURE:
<223> OTHER INFORMATION: Synthetic

<400> SEQUENCE: 42
gacatccaga tgacccagtc tccatcttcc gtgtctgcat ctgtaggaga cagagtcacc    60
atcacttgtc gggcgagtca gggtatcagc agctggttag cctggtatca gcagaaacca   120
gggaaagccc ctaagctcct gatctatgct gcatccagtt ttcaaagtgg ggtcccatca   180
aggttcagcg gcagtggatc tgggacagat ttcactctca ccatcagcag cctgcagcct   240
gaagattttg caacttactt ttgtcaacag gctaacagtt tccctctcac tttcggcgga   300
gggaccacgg tggagatcaa a                                             321

<210> SEQ ID NO 43
<211> LENGTH: 107
<212> TYPE: PRT
<213> ORGANISM: Artificial Sequence
<220> FEATURE:
<223> OTHER INFORMATION: Synthetic

<400> SEQUENCE: 43

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Phe Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Leu
                85                  90                  95

Thr Phe Gly Gly Gly Thr Thr Val Glu Ile Lys
            100                 105

<210> SEQ ID NO 44
<211> LENGTH: 18
<212> TYPE: DNA
<213> ORGANISM: Artificial Sequence
<220> FEATURE:
<223> OTHER INFORMATION: Synthetic

```
<400> SEQUENCE: 44
cagggtatca gcagctgg                                                      18

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Gln Gly Ile Ser Ser Trp
 1               5

<210> SEQ ID NO 46
<211> LENGTH: 9
<212> TYPE: DNA
<213> ORGANISM: Artificial Sequence
<220> FEATURE:
<223> OTHER INFORMATION: Synthetic

<400> SEQUENCE: 46 gctgcatcc                                                                 9

<210> SEQ ID NO 47
<211> LENGTH: 3
<212> TYPE: PRT
<213> ORGANISM: Artificial Sequence
<220> FEATURE:
<223> OTHER INFORMATION: Synthetic

<400> SEQUENCE: 47

Ala Ala Ser
 1

<210> SEQ ID NO 48
<211> LENGTH: 27
<212> TYPE: DNA
<213> ORGANISM: Artificial Sequence
<220> FEATURE:
<223> OTHER INFORMATION: Synthetic

<400> SEQUENCE: 48
caacaggcta acagtttccc tctcact                                            27

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Gln Gln Ala Asn Ser Phe Pro Leu Thr
 1               5

<210> SEQ ID NO 50
<211> LENGTH: 384
<212> TYPE: DNA
<213> ORGANISM: Artificial Sequence
<220> FEATURE:
<223> OTHER INFORMATION: Synthetic

<400> SEQUENCE: 50
caggttcagc tggtgcagtc tggagctgag gtgaagaagc ctggggcctc agtgaaggtc        60
```

```
tcctgcaagg cttctggtta cacctttaat agttatggaa tcagctgggt gcgacaggcc    120
cctggacaag ggcttgagtg gatgggatgg atcagaactt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagatgag    300
gcccgtatag tagtggctgg tacaactcct tactactacg gtatggacgt ctggggccaa    360
gggaccacgg tcaccgtctc ctca                                           384
```

<210> SEQ ID NO 51
<211> LENGTH: 128
<212> TYPE: PRT
<213> ORGANISM: Artificial Sequence
<220> FEATURE:
<223> OTHER INFORMATION: Synthetic

<400> SEQUENCE: 51

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Ser Tyr
            20                  25                  30

Gly Ile Ser Trp Val Arg Gln Ala Pro Gly Gln Gly Leu Glu Trp Met
        35                  40                  45

Gly Trp Ile Arg Thr Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Glu Ala Arg Ile Val Val Ala Gly Thr Thr Pro Tyr Tyr
            100                 105                 110

Tyr Gly Met Asp Val Trp Gly Gln Gly Thr Thr Val Thr Val Ser Ser
        115                 120                 125
```

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52

```
ggttacacct ttaatagtta tgga                                            24
```

<210> SEQ ID NO 53
<211> LENGTH: 8
<212> TYPE: PRT
<213> ORGANISM: Artificial Sequence
<220> FEATURE:
<223> OTHER INFORMATION: Synthetic

<400> SEQUENCE: 53

```
Gly Tyr Thr Phe Asn Ser Tyr Gly
 1               5
```

<210> SEQ ID NO 54
<211> LENGTH: 24
<212> TYPE: DNA
<213> ORGANISM: Artificial Sequence
<220> FEATURE:
<223> OTHER INFORMATION: Synthetic -continued

```
<400> SEQUENCE: 54
atcagaactt acaatggtaa caca                                              24

<210> SEQ ID NO 55
<211> LENGTH: 8
<212> TYPE: PRT
<213> ORGANISM: Artificial Sequence
<220> FEATURE:
<223> OTHER INFORMATION: Synthetic

<400> SEQUENCE: 55

Ile Arg Thr Tyr Asn Gly Asn Thr
 1               5

<210> SEQ ID NO 56
<211> LENGTH: 63
<212> TYPE: DNA
<213> ORGANISM: Artificial Sequence
<220> FEATURE:
<223> OTHER INFORMATION: Synthetic

<400> SEQUENCE: 56
gcgagagatg aggcccgtat agtagtggct ggtacaactc cttactacta cggtatggac       60
gtc                                                                    63

<210> SEQ ID NO 57
<211> LENGTH: 21
<212> TYPE: PRT
<213> ORGANISM: Artificial Sequence
<220> FEATURE:
<223> OTHER INFORMATION: Synthetic

<400> SEQUENCE: 57

Ala Arg Asp Glu Ala Arg Ile Val Val Ala Gly Thr Thr Pro Tyr Tyr
 1               5                  10                  15

Tyr Gly Met Asp Val
            20

<210> SEQ ID NO 58
<211> LENGTH: 321
<212> TYPE: DNA
<213> ORGANISM: Artificial Sequence
<220> FEATURE:
<223> OTHER INFORMATION: Synthetic

<400> SEQUENCE: 58
gacatccaga tgacccagtc tccatcttcc gtgtctgcat ctgtgggaga cagagtcacc       60
atcacttgtc gggcgagtca ggatattagt atttggttag cctggtatca gcagagtcca     120
gggaaagccc ctaaactcct gatcaatgtt gcatcccgtt tgcaaagtgg ggtcccatca     180
aggttcagcg gcagtggatc tgggacagat tcactctcac catcaacag tctgcagcct     240 gaagattttg taacttacta ttgtcaacag gctaacagtt tcccgatcac cttcggccaa     300
gggacacgac tggcgaccaa a                                               321

<210> SEQ ID NO 59
<211> LENGTH: 107
<212> TYPE: PRT
<213> ORGANISM: Artificial Sequence
<220> FEATURE:
<223> OTHER INFORMATION: Synthetic

<400> SEQUENCE: 59
```

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ile Trp
            20                  25                  30

Leu Ala Trp Tyr Gln Gln Ser Pro Gly Lys Ala Pro Lys Leu Leu Ile
        35                  40                  45

Asn Val Ala Ser Arg Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Val Thr Tyr Tyr Cys Gln Gln Ala Asn Ser Phe Pro Ile
                85                  90                  95

Thr Phe Gly Gln Gly Thr Arg Leu Ala Thr Lys
            100                 105

<210> SEQ ID NO 60
<211> LENGTH: 18
<212> TYPE: DNA
<213> ORGANISM: Artificial Sequence
<220> FEATURE:
<223> OTHER INFORMATION: Synthetic

<400> SEQUENCE: 60
caggatatta gtatttgg                                                    18

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

Gln Asp Ile Ser Ile Trp
1               5

<210> SEQ ID NO 62
<211> LENGTH: 9
<212> TYPE: DNA
<213> ORGANISM: Artificial Sequence
<220> FEATURE:
<223> OTHER INFORMATION: Synthetic

<400> SEQUENCE: 62 gttgcatcc                                                               9

<210> SEQ ID NO 63
<211> LENGTH: 3
<212> TYPE: PRT
<213> ORGANISM: Artificial Sequence
<220> FEATURE:
<223> OTHER INFORMATION: Synthetic

<400> SEQUENCE: 63

Val Ala Ser
1

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
caacaggcta acagtttccc gatcacc                                              27

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Gln Gln Ala Asn Ser Phe Pro Ile Thr
 1               5

<210> SEQ ID NO 66
<211> LENGTH: 351
<212> TYPE: DNA
<213> ORGANISM: Artificial Sequence
<220> FEATURE:
<223> OTHER INFORMATION: Synthetic

<400> SEQUENCE: 66
caggtgcagc tggtggagtc tgggggaggc ttggtccagc ctggagggtc cctgagactc        60
tcctgtgcag tttctggatt cacaatcagt gaccactaca tgagctggat ccgccaggct       120
ccagggaagg ggctggagtg gatttcatac attagtagta gtggtagtaa aatatactac       180
gcagactctg tgaagggccg attcaccatc tccagggaca acgccaagaa ctcactgttt       240
ctgcaaatga acagcctgag agccgaggac acggccgttt attactgtgc gagaacacga       300
cagctcgtgg gggactactg gggccaggga accctggtca ccgtctcctc a                351

<210> SEQ ID NO 67
<211> LENGTH: 117
<212> TYPE: PRT
<213> ORGANISM: Artificial Sequence
<220> FEATURE:
<223> OTHER INFORMATION: Synthetic

<400> SEQUENCE: 67

Gln Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Ile Ser Asp His
            20                  25                  30

Tyr Met Ser Trp Ile Arg Gln Ala Pro Gly Lys Gly Leu Glu Trp Ile
        35                  40                  45

Ser Tyr Ile Ser Ser Ser Gly Ser Lys Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Thr Arg Gln Leu Val Gly Asp Tyr Trp Gly Gln Gly Thr Leu
            100                 105                 110

Val Thr Val Ser Ser
        115

<210> SEQ ID NO 68
<211> LENGTH: 24
<212> TYPE: DNA
<213> ORGANISM: Artificial Sequence
<220> FEATURE:

<223> OTHER INFORMATION: Synthetic

<400> SEQUENCE: 68
ggattcacaa tcagtgacca ctac                                    24

<210> SEQ ID NO 69
<211> LENGTH: 8
<212> TYPE: PRT
<213> ORGANISM: Artificial Sequence
<220> FEATURE:
<223> OTHER INFORMATION: Synthetic

<400> SEQUENCE: 69

Gly Phe Thr Ile Ser Asp His Tyr
 1               5

<210> SEQ ID NO 70
<211> LENGTH: 24
<212> TYPE: DNA
<213> ORGANISM: Artificial Sequence
<220> FEATURE:
<223> OTHER INFORMATION: Synthetic

<400> SEQUENCE: 70
attagtagta gtggtagtaa aata                                    24

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Ile Ser Ser Ser Gly Ser Lys Ile
 1               5

<210> SEQ ID NO 72
<211> LENGTH: 30
<212> TYPE: DNA
<213> ORGANISM: Artificial Sequence
<220> FEATURE:
<223> OTHER INFORMATION: Synthetic

<400> SEQUENCE: 72
gcgagaacac gacagctcgt gggggactac                              30

<210> SEQ ID NO 73
<211> LENGTH: 10
<212> TYPE: PRT
<213> ORGANISM: Artificial Sequence
<220> FEATURE:
<223> OTHER INFORMATION: Synthetic

<400> SEQUENCE: 73

Ala Arg Thr Arg Gln Leu Val Gly Asp Tyr
 1               5                  10

<210> SEQ ID NO 74
<211> LENGTH: 321
<212> TYPE: DNA
<213> ORGANISM: Artificial Sequence
<220> FEATURE:
<223> OTHER INFORMATION: Synthetic

<400> SEQUENCE: 74

-continued

```
gacatccagt tgacccagtc tccatccttc ctgtctgcat ctgtaggaga cagagtcacc    60
atcacttgct gggccagtca gggcattagc agttatttag cctggtatca gcaaaaacca   120
gggaaagccc ctaagctcct gatctttgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatagtt acccgctcac tttcggcgga   300
gggaccaagg tggagatcag a                                             321
```

<210> SEQ ID NO 75
<211> LENGTH: 107
<212> TYPE: PRT
<213> ORGANISM: Artificial Sequence
<220> FEATURE:
<223> OTHER INFORMATION: Synthetic

<400> SEQUENCE: 75

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Phe Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Arg
            100                 105

<210> SEQ ID NO 76
<211> LENGTH: 18
<212> TYPE: DNA
<213> ORGANISM: Artificial Sequence
<220> FEATURE:
<223> OTHER INFORMATION: Synthetic

<400> SEQUENCE: 76

```
cagggcatta gcagttat                                                  18
```

<210> SEQ ID NO 77
<211> LENGTH: 6
<212> TYPE: PRT
<213> ORGANISM: Artificial Sequence
<220> FEATURE:
<223> OTHER INFORMATION: Synthetic

<400> SEQUENCE: 77

Gln Gly Ile Ser Ser Tyr
1               5

<210> SEQ ID NO 78
<211> LENGTH: 9
<212> TYPE: DNA
<213> ORGANISM: Artificial Sequence
<220> FEATURE:
<223> OTHER INFORMATION: Synthetic

<400> SEQUENCE: 78

```
gctgcatcc                                                             9
```

<210> SEQ ID NO 79
<211> LENGTH: 3
<212> TYPE: PRT
<213> ORGANISM: Artificial Sequence
<220> FEATURE:
<223> OTHER INFORMATION: Synthetic

<400> SEQUENCE: 79

Ala Ala Ser
 1

<210> SEQ ID NO 80
<211> LENGTH: 27
<212> TYPE: DNA
<213> ORGANISM: Artificial Sequence
<220> FEATURE:
<223> OTHER INFORMATION: Synthetic

<400> SEQUENCE: 80
caacagctta atagttaccc gctcact                                          27

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Gln Gln Leu Asn Ser Tyr Pro Leu Thr
 1               5

<210> SEQ ID NO 82
<211> LENGTH: 372
<212> TYPE: DNA
<213> ORGANISM: Artificial Sequence
<220> FEATURE:
<223> OTHER INFORMATION: Synthetic

<400> SEQUENCE: 82
gaagtgcagc tggtggagtc tgggggaggc ttggtacagc ctggcaggtc cctgagactc        60
tcctgtgcag cctctggatt cacctttgat aattatgcca tgcactgggt ccggcaagct       120
ccagggaagg gcctggagtg ggtctcaggt attaggtgga atagtggtag cataggctat       180
gcggactctg tgaagggccg attcaccatc tccagagaca cgccaagaa ctccctgtat        240 ctgcaaatga atagtctgag agctgaggac acggccttgt attactgtgc aaaagaaggt       300
ggatatagtg ctaccgcccc cggacccttc tttgactact ggggccaggg aaccctggtc       360
accgtctcct cc                                                          372

<210> SEQ ID NO 83
<211> LENGTH: 124
<212> TYPE: PRT
<213> ORGANISM: Artificial Sequence
<220> FEATURE:
<223> OTHER INFORMATION: Synthetic

<400> SEQUENCE: 83

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
            35                  40                  45

Ser Gly Ile Arg Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Glu Gly Gly Tyr Ser Gly Tyr Arg Pro Gly Pro Phe Phe Asp
            100                 105                 110

Tyr Trp Gly Gln Gly Thr Leu Val Thr Val Ser Ser
            115                 120

<210> SEQ ID NO 84
<211> LENGTH: 24
<212> TYPE: DNA
<213> ORGANISM: Artificial Sequence
<220> FEATURE:
<223> OTHER INFORMATION: Synthetic

<400> SEQUENCE: 84
ggattcacct ttgataatta tgcc                                         24

<210> SEQ ID NO 85
<211> LENGTH: 8
<212> TYPE: PRT
<213> ORGANISM: Artificial Sequence
<220> FEATURE:
<223> OTHER INFORMATION: Synthetic

<400> SEQUENCE: 85

Gly Phe Thr Phe Asp Asn Tyr Ala
 1               5

<210> SEQ ID NO 86
<211> LENGTH: 24
<212> TYPE: DNA
<213> ORGANISM: Artificial Sequence
<220> FEATURE:
<223> OTHER INFORMATION: Synthetic

<400> SEQUENCE: 86
attaggtgga atagtggtag cata                                         24

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

Ile Arg Trp Asn Ser Gly Ser Ile
 1               5

<210> SEQ ID NO 88
<211> LENGTH: 51
<212> TYPE: DNA
<213> ORGANISM: Artificial Sequence
<220> FEATURE:
<223> OTHER INFORMATION: Synthetic

<400> SEQUENCE: 88
gcaaaagaag gtggatatag tggctaccgc cccggaccct tctttgacta c            51

<210> SEQ ID NO 89
<211> LENGTH: 17
<212> TYPE: PRT
<213> ORGANISM: Artificial Sequence
<220> FEATURE:
<223> OTHER INFORMATION: Synthetic

<400> SEQUENCE: 89

Ala Lys Glu Gly Gly Tyr Ser Gly Tyr Arg Pro Gly Pro Phe Phe Asp
 1               5                  10                  15

Tyr

<210> SEQ ID NO 90
<211> LENGTH: 321
<212> TYPE: DNA
<213> ORGANISM: Artificial Sequence
<220> FEATURE:
<223> OTHER INFORMATION: Synthetic

<400> SEQUENCE: 90
gaaatagtga tgacgcagtc tccagccacc ctgtctgtgt ctccagggga aagagccacc     60
ctctcctgca gggccagtca gagtgttaac tacaacttag cctggtacca gcataaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggccgctcac tttcggcgga    300
gggaccaagg tggagatcaa a                                              321

<210> SEQ ID NO 91
<211> LENGTH: 107
<212> TYPE: PRT
<213> ORGANISM: Artificial Sequence
<220> FEATURE:
<223> OTHER INFORMATION: Synthetic

<400> SEQUENCE: 91

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Asn Tyr Asn
            20                  25                  30

Leu Ala Trp Tyr Gln His Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 92
<211> LENGTH: 18
<212> TYPE: DNA
<213> ORGANISM: Artificial Sequence
<220> FEATURE:
<223> OTHER INFORMATION: Synthetic

<400> SEQUENCE: 92
cagagtgtta actacaac                                                       18

<210> SEQ ID NO 93
<211> LENGTH: 6
<212> TYPE: PRT
<213> ORGANISM: Artificial Sequence
<220> FEATURE:
<223> OTHER INFORMATION: Synthetic

<400> SEQUENCE: 93

Gln Ser Val Asn Tyr Asn
 1               5

<210> SEQ ID NO 94
<211> LENGTH: 9
<212> TYPE: DNA
<213> ORGANISM: Artificial Sequence
<220> FEATURE:
<223> OTHER INFORMATION: Synthetic

<400> SEQUENCE: 94 ggtgcatcc                                                                  9

<210> SEQ ID NO 95
<211> LENGTH: 3
<212> TYPE: PRT
<213> ORGANISM: Artificial Sequence
<220> FEATURE:
<223> OTHER INFORMATION: Synthetic

<400> SEQUENCE: 95

Gly Ala Ser
 1

<210> SEQ ID NO 96
<211> LENGTH: 27
<212> TYPE: DNA
<213> ORGANISM: Artificial Sequence
<220> FEATURE:
<223> OTHER INFORMATION: Synthetic

<400> SEQUENCE: 96
cagcagtata ataactggcc gctcact                                              27

<210> SEQ ID NO 97
<211> LENGTH: 9
<212> TYPE: PRT
<213> ORGANISM: Artificial Sequence
<220> FEATURE:
<223> OTHER INFORMATION: Synthetic

<400> SEQUENCE: 97

Gln Gln Tyr Asn Asn Trp Pro Leu Thr
 1               5

<210> SEQ ID NO 98
<211> LENGTH: 351
<212> TYPE: DNA
<213> ORGANISM: Artificial Sequence
<220> FEATURE:
<223> OTHER INFORMATION: Synthetic

<400> SEQUENCE: 98
caggttcagc tggtgcagtc tggagctgag gtgaagaagc ctggggcctc agtgaaggtc          60
tcctgcaagg cttctggtta cacctttacc aactatggta tcagctgggt gcgacaggcc         120

```
cctggacaag ggcttgagtg gatgggatgg atcagcgttt acaatggtca cacaaactat    180
gcacagaagc tccagggcag agtcaccatg accacagaca catccacgag cacagcctac    240
atggagctga ggagcctcag atctgacgac acggccgtgt attactgtgc gagagggagt    300
ggctacgatt ttgactcctg gggccaggga accctggtca ccgtctcctc a             351
```

```
<210> SEQ ID NO 99
<211> LENGTH: 117
<212> TYPE: PRT
<213> ORGANISM: Artificial Sequence
<220> FEATURE:
<223> OTHER INFORMATION: Synthetic

<400> SEQUENCE: 99
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Gly Tyr Asp Phe Asp Ser Trp Gly Gln Gly Thr Leu
            100                 105                 110

Val Thr Val Ser Ser
        115

```
<210> SEQ ID NO 100
<211> LENGTH: 24
<212> TYPE: DNA
<213> ORGANISM: Artificial Sequence
<220> FEATURE:
<223> OTHER INFORMATION: Synthetic

<400> SEQUENCE: 100
ggttacacct ttaccaacta tggt                                             24

<210> SEQ ID NO 101
<211> LENGTH: 8
<212> TYPE: PRT
<213> ORGANISM: Artificial Sequence
<220> FEATURE:
<223> OTHER INFORMATION: Synthetic

<400> SEQUENCE: 101
```

Gly Tyr Thr Phe Thr Asn Tyr Gly
1               5

```
<210> SEQ ID NO 102
<211> LENGTH: 24
<212> TYPE: DNA
<213> ORGANISM: Artificial Sequence
<220> FEATURE:
<223> OTHER INFORMATION: Synthetic

<400> SEQUENCE: 102
atcagcgttt acaatggtca caca                                             24
```

<210> SEQ ID NO 103
<211> LENGTH: 8
<212> TYPE: PRT
<213> ORGANISM: Artificial Sequence
<220> FEATURE:
<223> OTHER INFORMATION: Synthetic

<400> SEQUENCE: 103

Ile Ser Val Tyr Asn Gly His Thr
 1               5

<210> SEQ ID NO 104
<211> LENGTH: 30
<212> TYPE: DNA
<213> ORGANISM: Artificial Sequence
<220> FEATURE:
<223> OTHER INFORMATION: Synthetic

<400> SEQUENCE: 104
gcgagaggga gtggctacga ttttgactcc                                        30

<210> SEQ ID NO 105
<211> LENGTH: 10
<212> TYPE: PRT
<213> ORGANISM: Artificial Sequence
<220> FEATURE:
<223> OTHER INFORMATION: Synthetic

<400> SEQUENCE: 105

Ala Arg Gly Ser Gly Tyr Asp Phe Asp Ser
 1               5                  10

<210> SEQ ID NO 106
<211> LENGTH: 321
<212> TYPE: DNA
<213> ORGANISM: Artificial Sequence
<220> FEATURE:
<223> OTHER INFORMATION: Synthetic

<400> SEQUENCE: 106
gccatccaga tgacccagtc ttcatcctcc ctgtctgcat ctgttggaga cagagtcacc        60
atcacttgcc gggcaagtca ggccattaga aatgctttag ctggtatca gcagaaaccg       120 gggaaagccc ctaaggtcct gatctatgct gcatccagtt tacaaagtgg catcccatca      180
aggttcagcg gcagtggatc tggcacagat ttcactctca ccatcagcag cctgcagcct      240
gaagattttg caacttatta ctgtctacaa gattacgatt accgtacac ttttggccag       300 gggaccaagc tggagatcaa a                                                321

<210> SEQ ID NO 107
<211> LENGTH: 107
<212> TYPE: PRT
<213> ORGANISM: Artificial Sequence
<220> FEATURE:
<223> OTHER INFORMATION: Synthetic

<400> SEQUENCE: 107

Ala Ile Gln Met Thr Gln Ser Ser Ser Leu Ser Ala Ser Val Gly
 1               5                  10                  15

Asp Arg Val Thr Ile Thr Cys Arg Ala Ser Gln Ala Ile Arg Asn Ala
             20                  25                  30

Leu Gly Trp Tyr Gln Gln Lys Pro Gly Lys Ala Pro Lys Val Leu Ile
         35                  40                  45

```
Tyr Ala Ala Ser Ser Leu Gln Ser Gly Ile Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asp Tyr Pro Tyr
                 85                  90                  95

Thr Phe Gly Gln Gly Thr Lys Leu Glu Ile Lys
            100                 105
```

<210> SEQ ID NO 108
<211> LENGTH: 18
<212> TYPE: DNA
<213> ORGANISM: Artificial Sequence
<220> FEATURE:
<223> OTHER INFORMATION: Synthetic

<400> SEQUENCE: 108
caggccatta gaaatgct                                              18

<210> SEQ ID NO 109
<211> LENGTH: 6
<212> TYPE: PRT
<213> ORGANISM: Artificial Sequence
<220> FEATURE:
<223> OTHER INFORMATION: Synthetic

<400> SEQUENCE: 109

```
Gln Ala Ile Arg Asn Ala
 1               5
```

<210> SEQ ID NO 110
<211> LENGTH: 9
<212> TYPE: DNA
<213> ORGANISM: Artificial Sequence
<220> FEATURE:
<223> OTHER INFORMATION: Synthetic

<400> SEQUENCE: 110 gctgcatcc                                                         9

<210> SEQ ID NO 111
<211> LENGTH: 3
<212> TYPE: PRT
<213> ORGANISM: Artificial Sequence
<220> FEATURE:
<223> OTHER INFORMATION: Synthetic

<400> SEQUENCE: 111

```
Ala Ala Ser
 1
```

<210> SEQ ID NO 112
<211> LENGTH: 27
<212> TYPE: DNA
<213> ORGANISM: Artificial Sequence
<220> FEATURE:
<223> OTHER INFORMATION: Synthetic

<400> SEQUENCE: 112
ctacaagatt acgattaccc gtacact                                    27

<210> SEQ ID NO 113
<211> LENGTH: 9
<212> TYPE: PRT
<213> ORGANISM: Artificial Sequence
<220> FEATURE:
<223> OTHER INFORMATION: Synthetic

<400> SEQUENCE: 113

Leu Gln Asp Tyr Asp Tyr Pro Tyr Thr
1               5

<210> SEQ ID NO 114
<211> LENGTH: 348
<212> TYPE: DNA
<213> ORGANISM: Artificial Sequence
<220> FEATURE:
<223> OTHER INFORMATION: Synthetic

<400> SEQUENCE: 114
caggtgcagc tggtacagtc tggggctgag gtgaagaagc ctggggcctc agtgaaggtc      60
tcctgcaagg cttctagata caccttcacc agttatgata tcaactgggt gcgacaggcc     120
actggacaag gcttgagtg gatgggatgg atgaacccaa acagtggtaa cacaggctat     180
gcacagaagt tccagggcag agtcaccatg accaggaaca cctccacaag cacagcctac     240
atggagctga gcagcctgag atctgaggac acggccgtgt attactgtgc gagagtacga     300
cgcttttttg actactgggg ccagggaacc ctggtcaccg tctcctca                 348

<210> SEQ ID NO 115
<211> LENGTH: 116
<212> TYPE: PRT
<213> ORGANISM: Artificial Sequence
<220> FEATURE:
<223> OTHER INFORMATION: Synthetic

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Arg Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Arg Phe Phe Asp Tyr Trp Gly Gln Gly Thr Leu Val
            100                 105                 110

Thr Val Ser Ser
        115

<210> SEQ ID NO 116
<211> LENGTH: 24
<212> TYPE: DNA
<213> ORGANISM: Artificial Sequence
<220> FEATURE:
<223> OTHER INFORMATION: Synthetic

<400> SEQUENCE: 116
agatacacct tcaccagtta tgat                                              24

<210> SEQ ID NO 117
<211> LENGTH: 8

<212> TYPE: PRT
<213> ORGANISM: Artificial Sequence
<220> FEATURE:
<223> OTHER INFORMATION: Synthetic

<400> SEQUENCE: 117

Arg Tyr Thr Phe Thr Ser Tyr Asp
1               5

<210> SEQ ID NO 118
<211> LENGTH: 24
<212> TYPE: DNA
<213> ORGANISM: Artificial Sequence
<220> FEATURE:
<223> OTHER INFORMATION: Synthetic

<400> SEQUENCE: 118
atgaacccaa acagtggtaa caca                                          24

<210> SEQ ID NO 119
<211> LENGTH: 8
<212> TYPE: PRT
<213> ORGANISM: Artificial Sequence
<220> FEATURE:
<223> OTHER INFORMATION: Synthetic

<400> SEQUENCE: 119

Met Asn Pro Asn Ser Gly Asn Thr
1               5

<210> SEQ ID NO 120
<211> LENGTH: 27
<212> TYPE: DNA
<213> ORGANISM: Artificial Sequence
<220> FEATURE:
<223> OTHER INFORMATION: Synthetic

<400> SEQUENCE: 120
gcgagagtac gacgcttttt tgactac                                       27

<210> SEQ ID NO 121
<211> LENGTH: 9
<212> TYPE: PRT
<213> ORGANISM: Artificial Sequence
<220> FEATURE:
<223> OTHER INFORMATION: Synthetic

<400> SEQUENCE: 121

Ala Arg Val Arg Arg Phe Phe Asp Tyr
1               5

<210> SEQ ID NO 122
<211> LENGTH: 321
<212> TYPE: DNA
<213> ORGANISM: Artificial Sequence
<220> FEATURE:
<223> OTHER INFORMATION: Synthetic

<400> SEQUENCE: 122
gacatccagt tgacccagtc tccatccttc ctgtctgcat ctgtaggaga cagagtcacc    60
atcacttgct gggccagtca gggcattatc agttatttag cctggtatca gcaaaaacca   120
gggaaagccc ctaagctcct gatctatgct gcatccactt tgcacagtgg ggtcccatca   180
aggttcagcg gcagtggatc tgggacagaa ttcactctca caatcagcag cctgcagcct   240
gaagattttg caacttatta ctgtcaccag cttaaaagtt acccgatcac cttcggccaa   300

-continued

```
gggacacgac tggagattaa a                                              321

<210> SEQ ID NO 123
<211> LENGTH: 107
<212> TYPE: PRT
<213> ORGANISM: Artificial Sequence
<220> FEATURE:
<223> OTHER INFORMATION: Synthetic

<400> SEQUENCE: 123

Asp Ile Gln Leu Thr Gln Ser Pro Ser Phe Leu Ser Ala Ser Val Gly
 1               5                  10                  15

Asp Arg Val Thr Ile Thr Cys Trp Ala Ser Gln Gly Ile Ile Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys His Gln Leu Lys Ser Tyr Pro Ile
                85                  90                  95

Thr Phe Gly Gln Gly Thr Arg Leu Glu Ile Lys
            100                 105

<210> SEQ ID NO 124
<211> LENGTH: 18
<212> TYPE: DNA
<213> ORGANISM: Artificial Sequence
<220> FEATURE:
<223> OTHER INFORMATION: Synthetic

<400> SEQUENCE: 124
cagggcatta tcagttat                                                   18

<210> SEQ ID NO 125
<211> LENGTH: 6
<212> TYPE: PRT
<213> ORGANISM: Artificial Sequence
<220> FEATURE:
<223> OTHER INFORMATION: Synthetic

<400> SEQUENCE: 125

Gln Gly Ile Ile Ser Tyr
 1               5

<210> SEQ ID NO 126
<211> LENGTH: 9
<212> TYPE: DNA
<213> ORGANISM: Artificial Sequence
<220> FEATURE:
<223> OTHER INFORMATION: Synthetic

<400> SEQUENCE: 126 gctgcatcc                                                              9

<210> SEQ ID NO 127
<211> LENGTH: 3
<212> TYPE: PRT
<213> ORGANISM: Artificial Sequence
<220> FEATURE:
<223> OTHER INFORMATION: Synthetic
```

-continued

<400> SEQUENCE: 127

Ala Ala Ser
 1

<210> SEQ ID NO 128
<211> LENGTH: 27
<212> TYPE: DNA
<213> ORGANISM: Artificial Sequence
<220> FEATURE:
<223> OTHER INFORMATION: Synthetic

<400> SEQUENCE: 128
caccagctta aaagttaccc gatcacc                                          27

<210> SEQ ID NO 129
<211> LENGTH: 9
<212> TYPE: PRT
<213> ORGANISM: Artificial Sequence
<220> FEATURE:
<223> OTHER INFORMATION: Synthetic

<400> SEQUENCE: 129

His Gln Leu Lys Ser Tyr Pro Ile Thr
 1               5

<210> SEQ ID NO 130
<211> LENGTH: 348
<212> TYPE: DNA
<213> ORGANISM: Artificial Sequence
<220> FEATURE:
<223> OTHER INFORMATION: Synthetic

<400> SEQUENCE: 130
caggtgcagt tggtggagac tgggggagac ttggtcaggc ctggagggtc cctgagactc       60
tcctgtacag cctctggatt caccctcagt gactactaca tgagctggat ccgtcaggct      120
ccagggaagg ggctggagtg ggtttcatac attaggagaa gtggtaatac catatactac      180
gcagactctg tgaagggccg attcaccatc tccaggaca acgccaagaa ctcactgtat       240
ctgcaaatga acagcctgag agccgaggac acggccgtat attactgtgc gagagggggg      300
gactgggcgg acgtctgggg ccaagggacc acggtcaccg tctcctca                  348

<210> SEQ ID NO 131
<211> LENGTH: 116
<212> TYPE: PRT
<213> ORGANISM: Artificial Sequence
<220> FEATURE:
<223> OTHER INFORMATION: Synthetic

<400> SEQUENCE: 131

Gln Val Gln Leu Val Glu Thr Gly Gly Asp Leu Val Arg Pro Gly Gly
 1               5                  10                  15

Ser Leu Arg Leu Ser Cys Thr Ala Ser Gly Phe Thr Leu Ser Asp Tyr
             20                  25                  30

Tyr Met Ser Trp Ile Arg Gln Ala Pro Gly Lys Gly Leu Glu Trp Val
         35                  40                  45

Ser Tyr Ile Arg Arg Ser Gly Asn Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

```
Ala Arg Gly Gly Asp Trp Ala Asp Val Trp Gly Gln Gly Thr Thr Val
            100                 105                 110
Thr Val Ser Ser
        115
```

<210> SEQ ID NO 132
<211> LENGTH: 24
<212> TYPE: DNA
<213> ORGANISM: Artificial Sequence
<220> FEATURE:
<223> OTHER INFORMATION: Synthetic

<400> SEQUENCE: 132
ggattcaccc tcagtgacta ctac                                          24

<210> SEQ ID NO 133
<211> LENGTH: 8
<212> TYPE: PRT
<213> ORGANISM: Artificial Sequence
<220> FEATURE:
<223> OTHER INFORMATION: Synthetic

<400> SEQUENCE: 133

```
Gly Phe Thr Leu Ser Asp Tyr Tyr
 1               5
```

<210> SEQ ID NO 134
<211> LENGTH: 24
<212> TYPE: DNA
<213> ORGANISM: Artificial Sequence
<220> FEATURE:
<223> OTHER INFORMATION: Synthetic

<400> SEQUENCE: 134
attaggagaa gtggtaatac cata                                          24

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

```
Ile Arg Arg Ser Gly Asn Thr Ile
 1               5
```

<210> SEQ ID NO 136
<211> LENGTH: 27
<212> TYPE: DNA
<213> ORGANISM: Artificial Sequence
<220> FEATURE:
<223> OTHER INFORMATION: Synthetic

<400> SEQUENCE: 136
gcgagagggg gggactgggc ggacgtc                                       27

<210> SEQ ID NO 137
<211> LENGTH: 9
<212> TYPE: PRT
<213> ORGANISM: Artificial Sequence
<220> FEATURE:
<223> OTHER INFORMATION: Synthetic

<400> SEQUENCE: 137

Ala Arg Gly Gly Asp Trp Ala Asp Val
 1               5

<210> SEQ ID NO 138
<211> LENGTH: 321
<212> TYPE: DNA
<213> ORGANISM: Artificial Sequence
<220> FEATURE:
<223> OTHER INFORMATION: Synthetic

<400> SEQUENCE: 138
gacatccaga tgacccagtc tccatcctca ctgtctgcct ctgtgggaga cagagtcacc      60
atcacttgtc gggcgagtca gggcattagc atttatttag cctggtttca gcagaaacca     120
gggaaagccc ctaagtccct gatctatgct gcatccagtt tgcaacgtgg ggtcccatca     180
aagttcagcg gcagtggatc tgggacagat ttcactctca ccatcagtag cctgcagcct     240
gaagattttg caacttatta ctgccaacag tataatagtt acccgtacac ttttggccag     300
gggaccaaac tggaaatcaa a                                               321

<210> SEQ ID NO 139
<211> LENGTH: 107
<212> TYPE: PRT
<213> ORGANISM: Artificial Sequence
<220> FEATURE:
<223> OTHER INFORMATION: Synthetic

<400> SEQUENCE: 139

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ile Tyr
             20                  25                  30

Leu Ala Trp Phe Gln Gln Lys Pro Gly Lys Ala Pro Lys Ser Leu Ile
         35                  40                  45

Tyr Ala Ala Ser Ser Leu Gln Arg Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105

<210> SEQ ID NO 140
<211> LENGTH: 18
<212> TYPE: DNA
<213> ORGANISM: Artificial Sequence
<220> FEATURE:
<223> OTHER INFORMATION: Synthetic

<400> SEQUENCE: 140
cagggcatta gcatttat                                                    18

<210> SEQ ID NO 141
<211> LENGTH: 6
<212> TYPE: PRT
<213> ORGANISM: Artificial Sequence
<220> FEATURE:
<223> OTHER INFORMATION: Synthetic

<400> SEQUENCE: 141

Gln Gly Ile Ser Ile Tyr

<210> SEQ ID NO 142
<211> LENGTH: 9
<212> TYPE: DNA
<213> ORGANISM: Artificial Sequence
<220> FEATURE:
<223> OTHER INFORMATION: Synthetic

<400> SEQUENCE: 142 gctgcatcc                                                                   9

<210> SEQ ID NO 143
<211> LENGTH: 3
<212> TYPE: PRT
<213> ORGANISM: Artificial Sequence
<220> FEATURE:
<223> OTHER INFORMATION: Synthetic

<400> SEQUENCE: 143

Ala Ala Ser
 1

<210> SEQ ID NO 144
<211> LENGTH: 27
<212> TYPE: DNA
<213> ORGANISM: Artificial Sequence
<220> FEATURE:
<223> OTHER INFORMATION: Synthetic

<400> SEQUENCE: 144
caacagtata atagttaccc gtacact                                              27

<210> SEQ ID NO 145
<211> LENGTH: 9
<212> TYPE: PRT
<213> ORGANISM: Artificial Sequence
<220> FEATURE:
<223> OTHER INFORMATION: Synthetic

<400> SEQUENCE: 145

Gln Gln Tyr Asn Ser Tyr Pro Tyr Thr
 1               5

<210> SEQ ID NO 146
<211> LENGTH: 351
<212> TYPE: DNA
<213> ORGANISM: Artificial Sequence
<220> FEATURE:
<223> OTHER INFORMATION: Synthetic

<400> SEQUENCE: 146
caggttcagc tggtgcagtc tggacctgag gtgaagaagc ctggggcctc agtgaaggtc      60
tcctgcaagg cttctggtta cacctttacc aactatggta tcagctgggt gcgacaggcc     120
cctggacaag ggcttgagtg gatgggatgg atcagcgttt acaatggtaa cataaactat     180
gcacagaagc tccagggcag agtcaccatg accacagaca catccacgag cacagcctac     240
atggacctga ggagcctgag atctgacgac acggccgtgt attactgtgc gagagggagt     300
ggctacgatt ttgactactg gggccaggga accctggtca ccgtctcctc a              351

<210> SEQ ID NO 147
<211> LENGTH: 117
<212> TYPE: PRT
<213> ORGANISM: Artificial Sequence

```
<220> FEATURE:
<223> OTHER INFORMATION: Synthetic

<400> SEQUENCE: 147

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Ile Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Asp Leu Arg Ser Leu Arg Ser Asp Thr Ala Val Tyr Tyr Cys
                85                  90                  95

Ala Arg Gly Ser Gly Tyr Asp Phe Asp Tyr Trp Gly Gln Gly Thr Leu
            100                 105                 110

Val Thr Val Ser Ser
        115

<210> SEQ ID NO 148
<211> LENGTH: 24
<212> TYPE: DNA
<213> ORGANISM: Artificial Sequence
<220> FEATURE:
<223> OTHER INFORMATION: Synthetic

<400> SEQUENCE: 148
ggttacacct ttaccaacta tggt                                          24

<210> SEQ ID NO 149
<211> LENGTH: 8
<212> TYPE: PRT
<213> ORGANISM: Artificial Sequence
<220> FEATURE:
<223> OTHER INFORMATION: Synthetic

<400> SEQUENCE: 149

Gly Tyr Thr Phe Thr Asn Tyr Gly
1               5

<210> SEQ ID NO 150
<211> LENGTH: 24
<212> TYPE: DNA
<213> ORGANISM: Artificial Sequence
<220> FEATURE:
<223> OTHER INFORMATION: Synthetic

<400> SEQUENCE: 150
atcagcgttt acaatggtaa cata                                          24

<210> SEQ ID NO 151
<211> LENGTH: 8
<212> TYPE: PRT
<213> ORGANISM: Artificial Sequence
<220> FEATURE:
<223> OTHER INFORMATION: Synthetic

<400> SEQUENCE: 151

Ile Ser Val Tyr Asn Gly Asn Ile
1               5
```

<210> SEQ ID NO 152
<211> LENGTH: 30
<212> TYPE: DNA
<213> ORGANISM: Artificial Sequence
<220> FEATURE:
<223> OTHER INFORMATION: Synthetic

<400> SEQUENCE: 152
gcgagaggga gtggctacga ttttgactac                                    30

<210> SEQ ID NO 153
<211> LENGTH: 10
<212> TYPE: PRT
<213> ORGANISM: Artificial Sequence
<220> FEATURE:
<223> OTHER INFORMATION: Synthetic

<400> SEQUENCE: 153

Ala Arg Gly Ser Gly Tyr Asp Phe Asp Tyr
 1               5                  10

<210> SEQ ID NO 154
<211> LENGTH: 321
<212> TYPE: DNA
<213> ORGANISM: Artificial Sequence
<220> FEATURE:
<223> OTHER INFORMATION: Synthetic

<400> SEQUENCE: 154
gccatccaga tgacccagtc tccatcctcc ctgtctgcat ctgttggaga cagagtcacc    60
atcacttgcc gggcaagtca ggacattaga aatgctttag ctggtatca gcagaaacca   120 gggaaagccc ctaagctcct gatctatgct gcatccagtt tacaaagtgg ggtcccatca   180
aggttcagcg gcagtgcttc tggcacagat ttcactctca ccatcagcag cctgcagcct   240
gaagattttg cagcttatta ctgtctacaa gattacaatt acccgtacac ttttggccag   300
gggaccaagc tggagatcaa a                                            321

<210> SEQ ID NO 155
<211> LENGTH: 107
<212> TYPE: PRT
<213> ORGANISM: Artificial Sequence
<220> FEATURE:
<223> OTHER INFORMATION: Synthetic

<400> SEQUENCE: 155

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Ala
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Ala Ser Gly Thr Asp Phe Thr Leu Thr Ile Ser Ser Leu Gln Pro
65                  70                  75                  80

Glu Asp Phe Ala Ala Tyr Tyr Cys Leu Gln Asp Tyr Asn Tyr Pro Tyr
                85                  90                  95

Thr Phe Gly Gln Gly Thr Lys Leu Glu Ile Lys
            100                 105

<210> SEQ ID NO 156
<211> LENGTH: 18
<212> TYPE: DNA
<213> ORGANISM: Artificial Sequence
<220> FEATURE:
<223> OTHER INFORMATION: Synthetic

<400> SEQUENCE: 156
caggacatta gaaatgct                                                    18

<210> SEQ ID NO 157
<211> LENGTH: 6
<212> TYPE: PRT
<213> ORGANISM: Artificial Sequence
<220> FEATURE:
<223> OTHER INFORMATION: Synthetic

<400> SEQUENCE: 157

Gln Asp Ile Arg Asn Ala
 1               5

<210> SEQ ID NO 158
<211> LENGTH: 9
<212> TYPE: DNA
<213> ORGANISM: Artificial Sequence
<220> FEATURE:
<223> OTHER INFORMATION: Synthetic

<400> SEQUENCE: 158 gctgcatcc                                                               9

<210> SEQ ID NO 159
<211> LENGTH: 3
<212> TYPE: PRT
<213> ORGANISM: Artificial Sequence
<220> FEATURE:
<223> OTHER INFORMATION: Synthetic

<400> SEQUENCE: 159

Ala Ala Ser
 1

<210> SEQ ID NO 160
<211> LENGTH: 27
<212> TYPE: DNA
<213> ORGANISM: Artificial Sequence
<220> FEATURE:
<223> OTHER INFORMATION: Synthetic

<400> SEQUENCE: 160
ctacaagatt acaattaccc gtacact                                          27

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

Leu Gln Asp Tyr Asn Tyr Pro Tyr Thr
 1               5

<210> SEQ ID NO 162
<211> LENGTH: 366
<212> TYPE: DNA
<213> ORGANISM: Artificial Sequence

```
<220> FEATURE:
<223> OTHER INFORMATION: Synthetic

<400> SEQUENCE: 162
caggttcagc tggtgcagtc tggagctgag gtgaagaagc ctggggcctc agtgaaggtc      60
tcctgcaagg attctgctta cacctttaat agatatggta tcagctgggt gcgacaggcc     120
cctggacaag gccttgagtg gatgggatgg atcagcgctt acactggtaa cacagtctat     180
gcacagaagc tccagggcag agtcaccatg accacagaca attccacgag cacagcttac     240
atggagctga ggagcctgag atctgacgac acggccgtgt attactgtgc gagagataag     300 tcgattttg gagtggttag agggtttgac tactggggcc agggaaccct ggtcaccgtc      360
tcctca                                                                 366

<210> SEQ ID NO 163
<211> LENGTH: 122
<212> TYPE: PRT
<213> ORGANISM: Artificial Sequence
<220> FEATURE:
<223> OTHER INFORMATION: Synthetic

<400> SEQUENCE: 163
```

Gln Val Gln Leu Val Gln Ser Gly Ala Glu Val Lys Lys Pro Gly Ala
 1               5                   10                  15

Ser Val Lys Val Ser Cys Lys Asp Ser Ala Tyr Thr Phe Asn Arg Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Thr Gly Asn Thr Val Tyr Ala Gln Lys Leu
     50                  55                  60

Gln Gly Arg Val Thr Met Thr Thr Asp Asn Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Lys Ser Ile Phe Gly Val Val Arg Gly Phe Asp Tyr Trp
            100                 105                 110

Gly Gln Gly Thr Leu Val Thr Val Ser Ser
        115                 120

```
<210> SEQ ID NO 164
<211> LENGTH: 24
<212> TYPE: DNA
<213> ORGANISM: Artificial Sequence
<220> FEATURE:
<223> OTHER INFORMATION: Synthetic

<400> SEQUENCE: 164
gcttacacct ttaatagata tggt                                              24

<210> SEQ ID NO 165
<211> LENGTH: 8
<212> TYPE: PRT
<213> ORGANISM: Artificial Sequence
<220> FEATURE:
<223> OTHER INFORMATION: Synthetic

<400> SEQUENCE: 165
```

Ala Tyr Thr Phe Asn Arg Tyr Gly
 1               5

<210> SEQ ID NO 166
<211> LENGTH: 24
<212> TYPE: DNA
<213> ORGANISM: Artificial Sequence
<220> FEATURE:
<223> OTHER INFORMATION: Synthetic

<400> SEQUENCE: 166
atcagcgctt acactggtaa caca                                          24

<210> SEQ ID NO 167
<211> LENGTH: 8
<212> TYPE: PRT
<213> ORGANISM: Artificial Sequence
<220> FEATURE:
<223> OTHER INFORMATION: Synthetic

<400> SEQUENCE: 167

Ile Ser Ala Tyr Thr Gly Asn Thr
 1               5

<210> SEQ ID NO 168
<211> LENGTH: 45
<212> TYPE: DNA
<213> ORGANISM: Artificial Sequence
<220> FEATURE:
<223> OTHER INFORMATION: Synthetic

<400> SEQUENCE: 168
gcgagagata agtcgatttt tggagtggtt agagggtttg actac                   45

<210> SEQ ID NO 169
<211> LENGTH: 15
<212> TYPE: PRT
<213> ORGANISM: Artificial Sequence
<220> FEATURE:
<223> OTHER INFORMATION: Synthetic

<400> SEQUENCE: 169

Ala Arg Asp Lys Ser Ile Phe Gly Val Val Arg Gly Phe Asp Tyr
 1               5                  10                  15

<210> SEQ ID NO 170
<211> LENGTH: 321
<212> TYPE: DNA
<213> ORGANISM: Artificial Sequence
<220> FEATURE:
<223> OTHER INFORMATION: Synthetic

<400> SEQUENCE: 170
gaaatagtga tgacgcagtc tccagtcacc ctgtctctgt ctccagggga aagagccacc    60
ctcccctgca gggccagtca gagtgttagc agcagcttag cctggtacca gcagaaagct   120
ggccagtctc ccaggctcct catctatggt gcatctacca gggccactgg tatcccagcc   180
aggttcagtg gcagtgggtc tgggacggag ttcactctca ccatcagcaa cctgcagtct   240
gaagattttg cagtttatta ctgtcagcag tataataact ggcctctcac tttcggcgga   300
gggaccaagg tggagatcaa a                                            321

<210> SEQ ID NO 171
<211> LENGTH: 107
<212> TYPE: PRT
<213> ORGANISM: Artificial Sequence
<220> FEATURE:
<223> OTHER INFORMATION: Synthetic

<400> SEQUENCE: 171

Glu Ile Val Met Thr Gln Ser Pro Val Thr Leu Ser Leu Ser Pro Gly
1               5                   10                  15

Glu Arg Ala Thr Leu Pro Cys Arg Ala Ser Gln Ser Val Ser Ser Ser
            20                  25                  30

Leu Ala Trp Tyr Gln Gln Lys Ala Gly Gln Ser Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Asn Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 172
<211> LENGTH: 18
<212> TYPE: DNA
<213> ORGANISM: Artificial Sequence
<220> FEATURE:
<223> OTHER INFORMATION: Synthetic

<400> SEQUENCE: 172
cagagtgtta gcagcagc                                                 18

<210> SEQ ID NO 173
<211> LENGTH: 6
<212> TYPE: PRT
<213> ORGANISM: Artificial Sequence
<220> FEATURE:
<223> OTHER INFORMATION: Synthetic

<400> SEQUENCE: 173

Gln Ser Val Ser Ser Ser
1               5

<210> SEQ ID NO 174
<211> LENGTH: 9
<212> TYPE: DNA
<213> ORGANISM: Artificial Sequence
<220> FEATURE:
<223> OTHER INFORMATION: Synthetic

<400> SEQUENCE: 174 ggtgcatct                                                            9

<210> SEQ ID NO 175
<211> LENGTH: 3
<212> TYPE: PRT
<213> ORGANISM: Artificial Sequence
<220> FEATURE:
<223> OTHER INFORMATION: Synthetic

<400> SEQUENCE: 175

Gly Ala Ser
1

<210> SEQ ID NO 176
<211> LENGTH: 27
<212> TYPE: DNA
<213> ORGANISM: Artificial Sequence
<220> FEATURE:

<223> OTHER INFORMATION: Synthetic

<400> SEQUENCE: 176
cagcagtata ataactggcc tctcact                                              27

<210> SEQ ID NO 177
<211> LENGTH: 9
<212> TYPE: PRT
<213> ORGANISM: Artificial Sequence
<220> FEATURE:
<223> OTHER INFORMATION: Synthetic

<400> SEQUENCE: 177

Gln Gln Tyr Asn Asn Trp Pro Leu Thr
 1               5

<210> SEQ ID NO 178
<211> LENGTH: 351
<212> TYPE: DNA
<213> ORGANISM: Artificial Sequence
<220> FEATURE:
<223> OTHER INFORMATION: Synthetic

<400> SEQUENCE: 178
caggttcagc tggtgcagtc tggagctgaa gtgaagaagc ctggggcctc agtgaaggtc      60
tcctgcaagg cttctggtta caccttracc aactatggcc tcacttgggt gcgacaggcc     120
ccgggacgag gtcttgagtg gatgggatgg atcagtgttt acaatggcaa cacaaactat     180
gcacagacgc tcaagggcag agtcaccatg accacagaca catccacgag cacagcctac     240
atggaactga gagcctgag atctgacgac acggccgttt attactgtgc gagagggagt     300
ggctacgatt ttgactactg gggccaggga accctggtca ccgtctcctc a              351

<210> SEQ ID NO 179
<211> LENGTH: 117
<212> TYPE: PRT
<213> ORGANISM: Artificial Sequence
<220> FEATURE:
<223> OTHER INFORMATION: Synthetic

<400> SEQUENCE: 179

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Gly Leu Thr Trp Val Arg Gln Ala Pro Gly Arg Gly Leu Glu Trp Met
         35                  40                  45

Gly Trp Ile Ser Val Tyr Asn Gly Asn Thr Asn Tyr Ala Gln Thr Leu
     50                  55                  60

Lys Gly Arg Val Thr Met Thr Thr Asp Thr Ser Thr Ser Thr Ala Tyr
 65                  70                  75                  80

Met Glu Leu Lys Ser Leu Arg Ser Asp Asp Thr Ala Val Tyr Tyr Cys
                 85                  90                  95

Ala Arg Gly Ser Gly Tyr Asp Phe Asp Tyr Trp Gly Gln Gly Thr Leu
            100                 105                 110

Val Thr Val Ser Ser
        115

<210> SEQ ID NO 180
<211> LENGTH: 24
<212> TYPE: DNA

<213> ORGANISM: Artificial Sequence
<220> FEATURE:
<223> OTHER INFORMATION: Synthetic

<400> SEQUENCE: 180
ggttacacct ttaccaacta tggc                                    24

<210> SEQ ID NO 181
<211> LENGTH: 8
<212> TYPE: PRT
<213> ORGANISM: Artificial Sequence
<220> FEATURE:
<223> OTHER INFORMATION: Synthetic

<400> SEQUENCE: 181

Gly Tyr Thr Phe Thr Asn Tyr Gly
 1               5

<210> SEQ ID NO 182
<211> LENGTH: 24
<212> TYPE: DNA
<213> ORGANISM: Artificial Sequence
<220> FEATURE:
<223> OTHER INFORMATION: Synthetic

<400> SEQUENCE: 182
atcagtgttt acaatggcaa caca                                    24

<210> SEQ ID NO 183
<211> LENGTH: 8
<212> TYPE: PRT
<213> ORGANISM: Artificial Sequence
<220> FEATURE:
<223> OTHER INFORMATION: Synthetic

<400> SEQUENCE: 183

Ile Ser Val Tyr Asn Gly Asn Thr
 1               5

<210> SEQ ID NO 184
<211> LENGTH: 30
<212> TYPE: DNA
<213> ORGANISM: Artificial Sequence
<220> FEATURE:
<223> OTHER INFORMATION: Synthetic

<400> SEQUENCE: 184
gcgagaggga gtggctacga ttttgactac                              30

<210> SEQ ID NO 185
<211> LENGTH: 10
<212> TYPE: PRT
<213> ORGANISM: Artificial Sequence
<220> FEATURE:
<223> OTHER INFORMATION: Synthetic

<400> SEQUENCE: 185

Ala Arg Gly Ser Gly Tyr Asp Phe Asp Tyr
 1               5                  10

<210> SEQ ID NO 186
<211> LENGTH: 321
<212> TYPE: DNA
<213> ORGANISM: Artificial Sequence
<220> FEATURE:
<223> OTHER INFORMATION: Synthetic -continued

<400> SEQUENCE: 186

```
gccatccaga tgacccagtc tccttcctcc ctgtctgcat ctgttggaga cagagtcgcc      60
atcacttgcc gggcaagtca ggacattaga aatgatttag gctggtatca gcagaaacca     120
gggaaagccc ctaagcttct gatccatact gcttccagtt tacaaagtgg ggtcccatca     180
aggttcagcg gcagtggatc tggcacagat tcactctca ccatcagcaa cctgcagcct      240
gaagattttg ccacttatta ctgtctccaa gataatagtt acccgtacac ttttggccag     300
gggaccaagc tggagatcaa t                                               321
```

<210> SEQ ID NO 187
<211> LENGTH: 107
<212> TYPE: PRT
<213> ORGANISM: Artificial Sequence
<220> FEATURE:
<223> OTHER INFORMATION: Synthetic

<400> SEQUENCE: 187

```
Ala Ile Gln Met Thr Gln Ser Pro Ser Ser Leu Ser Ala Ser Val Gly
 1               5                  10                  15
Asp Arg Val Ala Ile Thr Cys Arg Ala Ser Gln Asp Ile Arg Asn Asp
            20                  25                  30
Leu Gly Trp Tyr Gln Gln Lys Pro Gly Lys Ala Pro Lys Leu Leu Ile
        35                  40                  45
His Thr Ala Ser Ser Leu Gln Ser Gly Val Pro Ser Arg Phe Ser Gly
    50                  55                  60
Ser Gly Ser Gly Thr Asp Phe Thr Leu Thr Ile Ser Asn Leu Gln Pro
65                  70                  75                  80
Glu Asp Phe Ala Thr Tyr Tyr Cys Leu Gln Asp Asn Ser Tyr Pro Tyr
                85                  90                  95
Thr Phe Gly Gln Gly Thr Lys Leu Glu Ile Asn
           100                 105
```

<210> SEQ ID NO 188
<211> LENGTH: 18
<212> TYPE: DNA
<213> ORGANISM: Artificial Sequence
<220> FEATURE:
<223> OTHER INFORMATION: Synthetic

<400> SEQUENCE: 188

```
caggacatta gaaatgat                                                    18
```

<210> SEQ ID NO 189
<211> LENGTH: 6
<212> TYPE: PRT
<213> ORGANISM: Artificial Sequence
<220> FEATURE:
<223> OTHER INFORMATION: Synthetic

<400> SEQUENCE: 189

```
Gln Asp Ile Arg Asn Asp
 1               5
```

<210> SEQ ID NO 190
<211> LENGTH: 9
<212> TYPE: DNA
<213> ORGANISM: Artificial Sequence
<220> FEATURE:
<223> OTHER INFORMATION: Synthetic

<400> SEQUENCE: 190

```
<210> SEQ ID NO 191
<211> LENGTH: 3
<212> TYPE: PRT
<213> ORGANISM: Artificial Sequence
<220> FEATURE:
<223> OTHER INFORMATION: Synthetic

<400> SEQUENCE: 191

Thr Ala Ser
 1

<210> SEQ ID NO 192
<211> LENGTH: 27
<212> TYPE: DNA
<213> ORGANISM: Artificial Sequence
<220> FEATURE:
<223> OTHER INFORMATION: Synthetic

<400> SEQUENCE: 192
ctccaagata atagttaccc gtacact                                            27

<210> SEQ ID NO 193
<211> LENGTH: 9
<212> TYPE: PRT
<213> ORGANISM: Artificial Sequence
<220> FEATURE:
<223> OTHER INFORMATION: Synthetic

<400> SEQUENCE: 193

Leu Gln Asp Asn Ser Tyr Pro Tyr Thr
 1               5

<210> SEQ ID NO 194
<211> LENGTH: 348
<212> TYPE: DNA
<213> ORGANISM: Artificial Sequence
<220> FEATURE:
<223> OTHER INFORMATION: Synthetic

<400> SEQUENCE: 194
caggtgcaac tggtgcagtc tggggctgag gtgcagaagc ctggggcctc agtgaaggtc         60
tcctgcaagg cttctggata caccttcacc ggccagtata ttcactgggt tcgacaggcc        120
cctggacaag gacttgagtg gatgggatgg atcaacccta acagtggtgg cacaaacttt        180
gcacagaagt tcaggacagg gtcaccatg accagggaca cgtccatcgg cacagtatac         240
atggaactga ggaggctgac atctgacgac acggccgtat tttattgtgt gagagaaaag        300
agaggttttg atatctgggg ccaagggaca atggtcaccg tttcttca                    348

<210> SEQ ID NO 195
<211> LENGTH: 116
<212> TYPE: PRT
<213> ORGANISM: Artificial Sequence
<220> FEATURE:
<223> OTHER INFORMATION: Synthetic

<400> SEQUENCE: 195

Gln Val Gln Leu Val Gln Ser Gly Ala Glu Val Gln Lys Pro Gly Ala
 1               5                  10                  15

Ser Val Lys Val Ser Cys Lys Ala Ser Gly Tyr Thr Phe Thr Gly Gln
            20                  25                  30
```

Tyr Ile His Trp Val Arg Gln Ala Pro Gly Gln Gly Leu Glu Trp Met
         35                  40                  45

Gly Trp Ile Asn Pro Asn Ser Gly Gly Thr Asn Phe Ala Gln Lys Phe
    50                  55                  60

Gln Asp Arg Val Thr Met Thr Arg Asp Thr Ser Ile Gly Thr Val Tyr
65                  70                  75                  80

Met Glu Leu Arg Arg Leu Thr Ser Asp Asp Thr Ala Val Phe Tyr Cys
                85                  90                  95

Val Arg Glu Lys Arg Gly Phe Asp Ile Trp Gly Gln Gly Thr Met Val
            100                 105                 110

Thr Val Ser Ser
        115

<210> SEQ ID NO 196
<211> LENGTH: 24
<212> TYPE: DNA
<213> ORGANISM: Artificial Sequence
<220> FEATURE:
<223> OTHER INFORMATION: Synthetic

<400> SEQUENCE: 196
ggatacacct tcaccggcca gtat                                          24

<210> SEQ ID NO 197
<211> LENGTH: 8
<212> TYPE: PRT
<213> ORGANISM: Artificial Sequence
<220> FEATURE:
<223> OTHER INFORMATION: Synthetic

<400> SEQUENCE: 197

Gly Tyr Thr Phe Thr Gly Gln Tyr
 1               5

<210> SEQ ID NO 198
<211> LENGTH: 24
<212> TYPE: DNA
<213> ORGANISM: Artificial Sequence
<220> FEATURE:
<223> OTHER INFORMATION: Synthetic

<400> SEQUENCE: 198
atcaacccta acagtggtgg caca                                          24

<210> SEQ ID NO 199
<211> LENGTH: 8
<212> TYPE: PRT
<213> ORGANISM: Artificial Sequence
<220> FEATURE:
<223> OTHER INFORMATION: Synthetic

<400> SEQUENCE: 199

Ile Asn Pro Asn Ser Gly Gly Thr
 1               5

<210> SEQ ID NO 200
<211> LENGTH: 27
<212> TYPE: DNA
<213> ORGANISM: Artificial Sequence
<220> FEATURE:
<223> OTHER INFORMATION: Synthetic

<400> SEQUENCE: 200
gtgagagaaa agagaggttt tgatatc                                       27

<210> SEQ ID NO 201
<211> LENGTH: 9
<212> TYPE: PRT
<213> ORGANISM: Artificial Sequence
<220> FEATURE:
<223> OTHER INFORMATION: Synthetic

<400> SEQUENCE: 201

Val Arg Glu Lys Arg Gly Phe Asp Ile
 1               5

<210> SEQ ID NO 202
<211> LENGTH: 321
<212> TYPE: DNA
<213> ORGANISM: Artificial Sequence
<220> FEATURE:
<223> OTHER INFORMATION: Synthetic

<400> SEQUENCE: 202
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggccattcac tttcggccct   300
gggaccaaag tggatatcaa a                                             321

<210> SEQ ID NO 203
<211> LENGTH: 107
<212> TYPE: PRT
<213> ORGANISM: Artificial Sequence
<220> FEATURE:
<223> OTHER INFORMATION: Synthetic

<400> SEQUENCE: 203

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105

<210> SEQ ID NO 204
<211> LENGTH: 18
<212> TYPE: DNA
<213> ORGANISM: Artificial Sequence
<220> FEATURE:
<223> OTHER INFORMATION: Synthetic

<400> SEQUENCE: 204
cagagtgtta gcagcaac                                                  18

<210> SEQ ID NO 205
<211> LENGTH: 6
<212> TYPE: PRT
<213> ORGANISM: Artificial Sequence
<220> FEATURE:
<223> OTHER INFORMATION: Synthetic

<400> SEQUENCE: 205

Gln Ser Val Ser Ser Asn
 1               5

<210> SEQ ID NO 206
<211> LENGTH: 9
<212> TYPE: DNA
<213> ORGANISM: Artificial Sequence
<220> FEATURE:
<223> OTHER INFORMATION: Synthetic

<400> SEQUENCE: 206 ggtgcatcc                                                                  9

<210> SEQ ID NO 207
<211> LENGTH: 3
<212> TYPE: PRT
<213> ORGANISM: Artificial Sequence
<220> FEATURE:
<223> OTHER INFORMATION: Synthetic

<400> SEQUENCE: 207

Gly Ala Ser
 1

<210> SEQ ID NO 208
<211> LENGTH: 27
<212> TYPE: DNA
<213> ORGANISM: Artificial Sequence
<220> FEATURE:
<223> OTHER INFORMATION: Synthetic

<400> SEQUENCE: 208
cagcagtata ataactggcc attcact                                             27

<210> SEQ ID NO 209
<211> LENGTH: 9
<212> TYPE: PRT
<213> ORGANISM: Artificial Sequence
<220> FEATURE:
<223> OTHER INFORMATION: Synthetic

<400> SEQUENCE: 209

Gln Gln Tyr Asn Asn Trp Pro Phe Thr
 1               5

<210> SEQ ID NO 210
<211> LENGTH: 351
<212> TYPE: DNA
<213> ORGANISM: Artificial Sequence
<220> FEATURE:
<223> OTHER INFORMATION: Synthetic

<400> SEQUENCE: 210
caggttcatc tggtgcagtc tggagctgag gtgaagaagc ctggggcctc agtgaaggtc         60
tcctgcaagg cttctggtta ccctttacc aactatggta tcggctgggt gcgacaggcc        120
cctggacaag gcttgagtg gatgggatgg atcagtattt acaatggtaa cacaaattat        180

| | | | |
|---|---|---|---|
| gcacagaggc tccagggcag agtcaccatg accacagaca catccacgag cacagccttc | | | 240 |
| atggacctga ggagcctgaa atctgacgac acggccgttt attactgtgc gagaggtagt | | | 300 |
| ggctacaatt tcgaccactg gggccaggga accctggtca ccgtctcctc c | | | 351 |

```
<210> SEQ ID NO 211
<211> LENGTH: 117
<212> TYPE: PRT
<213> ORGANISM: Artificial Sequence
<220> FEATURE:
<223> OTHER INFORMATION: Synthetic

<400> SEQUENCE: 211
```

Gln Val His Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Gly Ile Gly Trp Val Arg Gln Ala Pro Gly Gln Gly Leu Glu Trp Met
         35                  40                  45

Gly Trp Ile Ser Ile Tyr Asn Gly Asn Thr Asn Tyr Ala Gln Arg Leu
     50                  55                  60

Gln Gly Arg Val Thr Met Thr Thr Asp Thr Ser Thr Ser Thr Ala Phe
 65                  70                  75                  80

Met Asp Leu Arg Ser Leu Lys Ser Asp Asp Thr Ala Val Tyr Tyr Cys
                 85                  90                  95

Ala Arg Gly Ser Gly Tyr Asn Phe Asp His Trp Gly Gln Gly Thr Leu
            100                 105                 110

Val Thr Val Ser Ser
        115

```
<210> SEQ ID NO 212
<211> LENGTH: 24
<212> TYPE: DNA
<213> ORGANISM: Artificial Sequence
<220> FEATURE:
<223> OTHER INFORMATION: Synthetic

<400> SEQUENCE: 212
```
ggttacacct ttaccaacta tggt                                      24

```
<210> SEQ ID NO 213
<211> LENGTH: 8
<212> TYPE: PRT
<213> ORGANISM: Artificial Sequence
<220> FEATURE:
<223> OTHER INFORMATION: Synthetic

<400> SEQUENCE: 213
```

Gly Tyr Thr Phe Thr Asn Tyr Gly
 1               5

```
<210> SEQ ID NO 214
<211> LENGTH: 24
<212> TYPE: DNA
<213> ORGANISM: Artificial Sequence
<220> FEATURE:
<223> OTHER INFORMATION: Synthetic

<400> SEQUENCE: 214
```
atcagtattt acaatggtaa caca                                      24

```
<210> SEQ ID NO 215
```

<211> LENGTH: 8
<212> TYPE: PRT
<213> ORGANISM: Artificial Sequence
<220> FEATURE:
<223> OTHER INFORMATION: Synthetic

<400> SEQUENCE: 215

Ile Ser Ile Tyr Asn Gly Asn Thr
1               5

<210> SEQ ID NO 216
<211> LENGTH: 30
<212> TYPE: DNA
<213> ORGANISM: Artificial Sequence
<220> FEATURE:
<223> OTHER INFORMATION: Synthetic

<400> SEQUENCE: 216
gcgagaggta gtggctacaa tttcgaccac                                     30

<210> SEQ ID NO 217
<211> LENGTH: 10
<212> TYPE: PRT
<213> ORGANISM: Artificial Sequence
<220> FEATURE:
<223> OTHER INFORMATION: Synthetic

<400> SEQUENCE: 217

Ala Arg Gly Ser Gly Tyr Asn Phe Asp His
1               5                   10

<210> SEQ ID NO 218
<211> LENGTH: 321
<212> TYPE: DNA
<213> ORGANISM: Artificial Sequence
<220> FEATURE:
<223> OTHER INFORMATION: Synthetic

<400> SEQUENCE: 218
gccatccaga tgacccagtc tccatcctcc ctgtctgcat ctgtaggaga cagagtcacc      60
atcacttgcc gggcaagtca gggcattaga aatgatttag gctggtatca gcagataccg     120
gggaaagccc ctaaactcct gatctatgct gcatccagtt tacaaagtgg ggtcccgtca     180
aggttcagcg gcagtggatc tggcacagat ttcactctca ccatcagcaa cctgcagcct     240
gaagattttg cagtttattt ctgtctacaa gataacactt atccgtacac ttttggccag     300
gggaccaatc tggagagcaa a                                              321

<210> SEQ ID NO 219
<211> LENGTH: 107
<212> TYPE: PRT
<213> ORGANISM: Artificial Sequence
<220> FEATURE:
<223> OTHER INFORMATION: Synthetic

<400> SEQUENCE: 219

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Asn Leu Gln Pro
 65                  70                  75                  80

Glu Asp Phe Ala Val Tyr Phe Cys Leu Gln Asp Asn Thr Tyr Pro Tyr
                 85                  90                  95

Thr Phe Gly Gln Gly Thr Asn Leu Glu Ser Lys
            100                 105

<210> SEQ ID NO 220
<211> LENGTH: 18
<212> TYPE: DNA
<213> ORGANISM: Artificial Sequence
<220> FEATURE:
<223> OTHER INFORMATION: Synthetic

<400> SEQUENCE: 220
cagggcatta gaaatgat                                                       18

<210> SEQ ID NO 221
<211> LENGTH: 6
<212> TYPE: PRT
<213> ORGANISM: Artificial Sequence
<220> FEATURE:
<223> OTHER INFORMATION: Synthetic

<400> SEQUENCE: 221

Gln Gly Ile Arg Asn Asp
 1               5

<210> SEQ ID NO 222
<211> LENGTH: 9
<212> TYPE: DNA
<213> ORGANISM: Artificial Sequence
<220> FEATURE:
<223> OTHER INFORMATION: Synthetic

<400> SEQUENCE: 222 gctgcatcc                                                                  9

<210> SEQ ID NO 223
<211> LENGTH: 3
<212> TYPE: PRT
<213> ORGANISM: Artificial Sequence
<220> FEATURE:
<223> OTHER INFORMATION: Synthetic

<400> SEQUENCE: 223

Ala Ala Ser
 1

<210> SEQ ID NO 224
<211> LENGTH: 27
<212> TYPE: DNA
<213> ORGANISM: Artificial Sequence
<220> FEATURE:
<223> OTHER INFORMATION: Synthetic

<400> SEQUENCE: 224
ctacaagata acacttatcc gtacact                                             27

<210> SEQ ID NO 225
<211> LENGTH: 9
<212> TYPE: PRT
<213> ORGANISM: Artificial Sequence
<220> FEATURE:
<223> OTHER INFORMATION: Synthetic
```

<400> SEQUENCE: 225

Leu Gln Asp Asn Thr Tyr Pro Tyr Thr
1               5

<210> SEQ ID NO 226
<211> LENGTH: 351
<212> TYPE: DNA
<213> ORGANISM: Artificial Sequence
<220> FEATURE:
<223> OTHER INFORMATION: Synthetic

<400> SEQUENCE: 226

```
caggttcagt tggtgcagtc tggacctgag gtgaagaagc ctggggcctc agtgaaggtc      60
tcctgcaagg cttctggtta ccctttacc aactatggta tcagttgggt gcgacaggcc     120
cctggacaag ggcttgagtg gatgggatgg atcagcgttt acaatggtaa acaaactat     180
gcacagaagt tccagggcag agtcaccatg accacagaca catccacgag cacagcctac     240
atggacctga ggagcctgag atctgacgac acggccgtat attactgtgc gagagggagt     300
ggctacgatt ttgactactg gggccaggga accctggtca ccgtctcctc a              351
```

<210> SEQ ID NO 227
<211> LENGTH: 117
<212> TYPE: PRT
<213> ORGANISM: Artificial Sequence
<220> FEATURE:
<223> OTHER INFORMATION: Synthetic

<400> SEQUENCE: 227

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Lys Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Gly Ser Gly Tyr Asp Phe Asp Tyr Trp Gly Gln Gly Thr Leu
            100                 105                 110

Val Thr Val Ser Ser
        115

<210> SEQ ID NO 228
<211> LENGTH: 24
<212> TYPE: DNA
<213> ORGANISM: Artificial Sequence
<220> FEATURE:
<223> OTHER INFORMATION: Synthetic

<400> SEQUENCE: 228

```
ggttacacct ttaccaacta tggt                                              24
```

<210> SEQ ID NO 229
<211> LENGTH: 8
<212> TYPE: PRT
<213> ORGANISM: Artificial Sequence
<220> FEATURE:
<223> OTHER INFORMATION: Synthetic

<400> SEQUENCE: 229

Gly Tyr Thr Phe Thr Asn Tyr Gly
1               5

<210> SEQ ID NO 230
<211> LENGTH: 24
<212> TYPE: DNA
<213> ORGANISM: Artificial Sequence
<220> FEATURE:
<223> OTHER INFORMATION: Synthetic

<400> SEQUENCE: 230
atcagcgttt acaatggtaa aaca                                          24

<210> SEQ ID NO 231
<211> LENGTH: 8
<212> TYPE: PRT
<213> ORGANISM: Artificial Sequence
<220> FEATURE:
<223> OTHER INFORMATION: Synthetic

<400> SEQUENCE: 231

Ile Ser Val Tyr Asn Gly Lys Thr
1               5

<210> SEQ ID NO 232
<211> LENGTH: 30
<212> TYPE: DNA
<213> ORGANISM: Artificial Sequence
<220> FEATURE:
<223> OTHER INFORMATION: Synthetic

<400> SEQUENCE: 232
gcgagaggga gtggctacga ttttgactac                                    30

<210> SEQ ID NO 233
<211> LENGTH: 10
<212> TYPE: PRT
<213> ORGANISM: Artificial Sequence
<220> FEATURE:
<223> OTHER INFORMATION: Synthetic

<400> SEQUENCE: 233

Ala Arg Gly Ser Gly Tyr Asp Phe Asp Tyr
1               5                   10

<210> SEQ ID NO 234
<211> LENGTH: 321
<212> TYPE: DNA
<213> ORGANISM: Artificial Sequence
<220> FEATURE:
<223> OTHER INFORMATION: Synthetic

<400> SEQUENCE: 234
gccatccaga tgacccagtc tccatcctcc ctgtctgcat ctgtaggaga cagagtcacc    60
atcacttgcc gggcaagtca gggcattaga aatgctttag ctggtatca gcagaaacca   120 gggaaagccc ctaagctcct gatctttgct tcatccagtt tacaaagtgg ggtcccatca   180
aggttcagcg gcagtggatc tggcacagat tcactctca ccatccgcag cctgcagcct   240
gaagattttg cagcttatta ctgtctacaa gattataatt acccgtacac ttttggccag   300
gggaccaagc tggagatcaa a                                            321

<210> SEQ ID NO 235
<211> LENGTH: 107
<212> TYPE: PRT
<213> ORGANISM: Artificial Sequence
<220> FEATURE:
<223> OTHER INFORMATION: Synthetic

<400> SEQUENCE: 235

```
Ala Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Ala
            20                  25                  30
Leu Gly Trp Tyr Gln Gln Lys Pro Gly Lys Ala Pro Lys Leu Leu Ile
        35                  40                  45
Phe Ala Ser Ser Leu Gln Ser Gly Val Pro Ser Arg Phe Ser Gly
    50                  55                  60
Ser Gly Ser Gly Thr Asp Phe Thr Leu Thr Ile Arg Ser Leu Gln Pro
65                  70                  75                  80
Glu Asp Phe Ala Ala Tyr Tyr Cys Leu Gln Asp Tyr Asn Tyr Pro Tyr
                85                  90                  95
Thr Phe Gly Gln Gly Thr Lys Leu Glu Ile Lys
            100                 105
```

<210> SEQ ID NO 236
<211> LENGTH: 18
<212> TYPE: DNA
<213> ORGANISM: Artificial Sequence
<220> FEATURE:
<223> OTHER INFORMATION: Synthetic

<400> SEQUENCE: 236
cagggcatta gaaatgct                                            18

<210> SEQ ID NO 237
<211> LENGTH: 6
<212> TYPE: PRT
<213> ORGANISM: Artificial Sequence
<220> FEATURE:
<223> OTHER INFORMATION: Synthetic

<400> SEQUENCE: 237

```
Gln Gly Ile Arg Asn Ala
 1               5
```

<210> SEQ ID NO 238
<211> LENGTH: 9
<212> TYPE: DNA
<213> ORGANISM: Artificial Sequence
<220> FEATURE:
<223> OTHER INFORMATION: Synthetic

<400> SEQUENCE: 238 gcttcatcc                                                       9

<210> SEQ ID NO 239
<211> LENGTH: 3
<212> TYPE: PRT
<213> ORGANISM: Artificial Sequence
<220> FEATURE:
<223> OTHER INFORMATION: Synthetic

<400> SEQUENCE: 239

Ala Ser Ser
 1

<210> SEQ ID NO 240
<211> LENGTH: 27
<212> TYPE: DNA
<213> ORGANISM: Artificial Sequence
<220> FEATURE:
<223> OTHER INFORMATION: Synthetic

<400> SEQUENCE: 240
ctacaagatt ataattaccc gtacact                                          27

<210> SEQ ID NO 241
<211> LENGTH: 9
<212> TYPE: PRT
<213> ORGANISM: Artificial Sequence
<220> FEATURE:
<223> OTHER INFORMATION: Synthetic

<400> SEQUENCE: 241

Leu Gln Asp Tyr Asn Tyr Pro Tyr Thr
 1               5

<210> SEQ ID NO 242
<211> LENGTH: 351
<212> TYPE: DNA
<213> ORGANISM: Artificial Sequence
<220> FEATURE:
<223> OTHER INFORMATION: Synthetic

<400> SEQUENCE: 242
caggttcagc tggtgcagtc tggagctgag gtgaagaagc ctggggcctc agtgaaggtc      60
tcctgcaagg cttctggtta cacctttacc agctatggta tcagctgggt gcgacaggcc    120
cctggacaag gcttgagtg gatgggatgg atcagtgttt acaatggtaa cacaaactat      180
gcacagaagc tccagggcag agtcaccatg accacagaca catccacgag cacagcctac    240
atggacctga ggagcctgag atctgacgac gcggccgtgt attactgtgc gagagggagt    300
ggctacgatt ttgactactg gggccaggga accctggtca ccgtctcctc a             351

<210> SEQ ID NO 243
<211> LENGTH: 117
<212> TYPE: PRT
<213> ORGANISM: Artificial Sequence
<220> FEATURE:
<223> OTHER INFORMATION: Synthetic

<400> SEQUENCE: 243

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Val Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
 65                  70                  75                  80

Met Asp Leu Arg Ser Leu Arg Ser Asp Asp Ala Ala Val Tyr Tyr Cys
                85                  90                  95

Ala Arg Gly Ser Gly Tyr Asp Phe Asp Tyr Trp Gly Gln Gly Thr Leu 100                 105                 110

Val Thr Val Ser Ser
        115

<210> SEQ ID NO 244
<211> LENGTH: 24
<212> TYPE: DNA
<213> ORGANISM: Artificial Sequence
<220> FEATURE:
<223> OTHER INFORMATION: Synthetic

<400> SEQUENCE: 244
ggttacacct ttaccagcta tggt                                          24

<210> SEQ ID NO 245
<211> LENGTH: 8
<212> TYPE: PRT
<213> ORGANISM: Artificial Sequence
<220> FEATURE:
<223> OTHER INFORMATION: Synthetic

<400> SEQUENCE: 245

Gly Tyr Thr Phe Thr Ser Tyr Gly
1               5

<210> SEQ ID NO 246
<211> LENGTH: 24
<212> TYPE: DNA
<213> ORGANISM: Artificial Sequence
<220> FEATURE:
<223> OTHER INFORMATION: Synthetic

<400> SEQUENCE: 246
atcagtgttt acaatggtaa caca                                          24

<210> SEQ ID NO 247
<211> LENGTH: 8
<212> TYPE: PRT
<213> ORGANISM: Artificial Sequence
<220> FEATURE:
<223> OTHER INFORMATION: Synthetic

<400> SEQUENCE: 247

Ile Ser Val Tyr Asn Gly Asn Thr
1               5

<210> SEQ ID NO 248
<211> LENGTH: 30
<212> TYPE: DNA
<213> ORGANISM: Artificial Sequence
<220> FEATURE:
<223> OTHER INFORMATION: Synthetic

<400> SEQUENCE: 248
gcgagaggga gtggctacga ttttgactac                                    30

<210> SEQ ID NO 249
<211> LENGTH: 10
<212> TYPE: PRT
<213> ORGANISM: Artificial Sequence
<220> FEATURE:
<223> OTHER INFORMATION: Synthetic

<400> SEQUENCE: 249

Ala Arg Gly Ser Gly Tyr Asp Phe Asp Tyr
1               5                   10

<210> SEQ ID NO 250
<211> LENGTH: 321
<212> TYPE: DNA
<213> ORGANISM: Artificial Sequence
<220> FEATURE:
<223> OTHER INFORMATION: Synthetic

<400> SEQUENCE: 250

```
gccatccaga tgacccagtc tccatcctcc ctgtctgcat ctgtaggaga cagagtcacc    60
atcacttgcc gggcaagtca gggcattaga aatgctttag ctggtatca gcagaaacca   120
gggaaagccc ctaaactcct gatctatgct gcatccagtt tacaaagtgg ggtcccatca   180
aggttcagcg gcagtggatc tggtacagat ttcactctca ccatcagcag cctgcagtct   240
gaagattttg caacttatta ctgtctacaa gattacaatt acccgtacac ttttggccag   300
gggaccaagc tggagatcaa a                                              321
```

<210> SEQ ID NO 251
<211> LENGTH: 107
<212> TYPE: PRT
<213> ORGANISM: Artificial Sequence
<220> FEATURE:
<223> OTHER INFORMATION: Synthetic

<400> SEQUENCE: 251

```
Ala Ile Gln Met Thr Gln Ser Pro Ser Ser Leu Ser Ala Ser Val Gly
  1               5                  10                  15
Asp Arg Val Thr Ile Thr Cys Arg Ala Ser Gln Gly Ile Arg Asn Ala
             20                  25                  30
Leu Gly Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Ser
 65                  70                  75                  80
Glu Asp Phe Ala Thr Tyr Tyr Cys Leu Gln Asp Tyr Asn Tyr Pro Tyr
                 85                  90                  95
Thr Phe Gly Gln Gly Thr Lys Leu Glu Ile Lys
            100                 105
```

<210> SEQ ID NO 252
<211> LENGTH: 18
<212> TYPE: DNA
<213> ORGANISM: Artificial Sequence
<220> FEATURE:
<223> OTHER INFORMATION: Synthetic

<400> SEQUENCE: 252

```
cagggcatta gaaatgct                                                   18
```

<210> SEQ ID NO 253
<211> LENGTH: 6
<212> TYPE: PRT
<213> ORGANISM: Artificial Sequence
<220> FEATURE:
<223> OTHER INFORMATION: Synthetic

<400> SEQUENCE: 253

```
Gln Gly Ile Arg Asn Ala
  1               5
```

```
<210> SEQ ID NO 254
<211> LENGTH: 9
<212> TYPE: DNA
<213> ORGANISM: Artificial Sequence
<220> FEATURE:
<223> OTHER INFORMATION: Synthetic

<400> SEQUENCE: 254 gctgcatcc                                                                 9

<210> SEQ ID NO 255
<211> LENGTH: 3
<212> TYPE: PRT
<213> ORGANISM: Artificial Sequence
<220> FEATURE:
<223> OTHER INFORMATION: Synthetic

<400> SEQUENCE: 255

Ala Ala Ser
 1

<210> SEQ ID NO 256
<211> LENGTH: 27
<212> TYPE: DNA
<213> ORGANISM: Artificial Sequence
<220> FEATURE:
<223> OTHER INFORMATION: Synthetic

<400> SEQUENCE: 256
ctacaagatt acaattaccc gtacact                                            27

<210> SEQ ID NO 257
<211> LENGTH: 9
<212> TYPE: PRT
<213> ORGANISM: Artificial Sequence
<220> FEATURE:
<223> OTHER INFORMATION: Synthetic

<400> SEQUENCE: 257

Leu Gln Asp Tyr Asn Tyr Pro Tyr Thr
 1               5

<210> SEQ ID NO 258
<211> LENGTH: 357
<212> TYPE: DNA
<213> ORGANISM: Artificial Sequence
<220> FEATURE:
<223> OTHER INFORMATION: Synthetic

<400> SEQUENCE: 258
caggtgcgac tggtggagtc tgggggaggc gtggtccagc ctggagggtc cctgagactc        60
tcctgtgtag cctctggatt caccttcaga agctatggca tgcactgggt ccgccaggct       120
ccaggcaggg gactggagtg ggtggcagtt atatcatatg atggcagtaa aacattctac       180
gtagattccg tgaaggtccg attcaccatc tccagagaca attccaagaa cacgctttat       240
ttggaaatga acagcctgag agttgacgac acggctgtgt atttctgtgt gaaagaagga       300
agaagtggga gttggttcga ccctggggc cagggaaccc tggtcgccgt ctcctca           357

<210> SEQ ID NO 259
<211> LENGTH: 119
<212> TYPE: PRT
<213> ORGANISM: Artificial Sequence
<220> FEATURE:
<223> OTHER INFORMATION: Synthetic
```

<400> SEQUENCE: 259

Gln Val Arg Leu Val Glu Ser Gly Gly Gly Val Val Gln Pro Gly Gly
1               5                   10                  15

Ser Leu Arg Leu Ser Cys Val Ala Ser Gly Phe Thr Phe Arg Ser Tyr
            20                  25                  30

Gly Met His Trp Val Arg Gln Ala Pro Gly Arg Gly Leu Glu Trp Val
        35                  40                  45

Ala Val Ile Ser Tyr Asp Gly Ser Lys Thr Phe Tyr Val Asp Ser Val
    50                  55                  60

Lys Val Arg Phe Thr Ile Ser Arg Asp Asn Ser Lys Asn Thr Leu Tyr
65                  70                  75                  80

Leu Glu Met Asn Ser Leu Arg Val Asp Asp Thr Ala Val Tyr Phe Cys
                85                  90                  95

Val Lys Glu Gly Arg Ser Gly Ser Trp Phe Asp Pro Trp Gly Gln Gly
            100                 105                 110

Thr Leu Val Ala Val Ser Ser
        115

<210> SEQ ID NO 260
<211> LENGTH: 24
<212> TYPE: DNA
<213> ORGANISM: Artificial Sequence
<220> FEATURE:
<223> OTHER INFORMATION: Synthetic

<400> SEQUENCE: 260
ggattcacct tcagaagcta tggc                                          24

<210> SEQ ID NO 261
<211> LENGTH: 8
<212> TYPE: PRT
<213> ORGANISM: Artificial Sequence
<220> FEATURE:
<223> OTHER INFORMATION: Synthetic

<400> SEQUENCE: 261

Gly Phe Thr Phe Arg Ser Tyr Gly
1               5

<210> SEQ ID NO 262
<211> LENGTH: 24
<212> TYPE: DNA
<213> ORGANISM: Artificial Sequence
<220> FEATURE:
<223> OTHER INFORMATION: Synthetic

<400> SEQUENCE: 262
atatcatatg atggcagtaa aaca                                          24

<210> SEQ ID NO 263
<211> LENGTH: 8
<212> TYPE: PRT
<213> ORGANISM: Artificial Sequence
<220> FEATURE:
<223> OTHER INFORMATION: Synthetic

<400> SEQUENCE: 263

Ile Ser Tyr Asp Gly Ser Lys Thr
1               5

<210> SEQ ID NO 264

```
<211> LENGTH: 36
<212> TYPE: DNA
<213> ORGANISM: Artificial Sequence
<220> FEATURE:
<223> OTHER INFORMATION: Synthetic

<400> SEQUENCE: 264
gtgaaagaag gaagaagtgg gagttggttc gacccc                                36

<210> SEQ ID NO 265
<211> LENGTH: 12
<212> TYPE: PRT
<213> ORGANISM: Artificial Sequence
<220> FEATURE:
<223> OTHER INFORMATION: Synthetic

<400> SEQUENCE: 265

Val Lys Glu Gly Arg Ser Gly Ser Trp Phe Asp Pro
 1               5                  10

<210> SEQ ID NO 266
<211> LENGTH: 321
<212> TYPE: DNA
<213> ORGANISM: Artificial Sequence
<220> FEATURE:
<223> OTHER INFORMATION: Synthetic

<400> SEQUENCE: 266
gacatccaga tgacccagtc tccatcctca ctgtctgcgt ctgtaggaga cagagtcacc        60
atcacttgtc gggcgagtca ggccattaac aattttttag cctggtttca gcagaaacca      120
gggaaaaccc ctaactccct gatctttgct acatccagtt tacaaagtgg ggtcccatca      180
aggttcagcg ccggtggatc tgggacagac ttcactctca ccatcagcag cctgcagcct      240
gaagattttg caacttatta ctgccaacag tataatagtc acccgtggac gttcggccaa      300
gggaccaagg tggaaatcaa a                                                321

<210> SEQ ID NO 267
<211> LENGTH: 107
<212> TYPE: PRT
<213> ORGANISM: Artificial Sequence
<220> FEATURE:
<223> OTHER INFORMATION: Synthetic

<400> SEQUENCE: 267

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Asn Asn Phe
             20                  25                  30

Leu Ala Trp Phe Gln Gln Lys Pro Gly Lys Thr Pro Asn Ser Leu Ile
         35                  40                  45

Phe Ala Thr Ser Ser Leu Gln Ser Gly Val Pro Ser Arg Phe Ser Ala
     50                  55                  60

Gly Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                 85                  90                  95

Thr Phe Gly Gln Gly Thr Lys Val Glu Ile Lys
            100                 105

<210> SEQ ID NO 268
<211> LENGTH: 18
```

```
<212> TYPE: DNA
<213> ORGANISM: Artificial Sequence
<220> FEATURE:
<223> OTHER INFORMATION: Synthetic

<400> SEQUENCE: 268
caggccatta acaatttt                                                      18

<210> SEQ ID NO 269
<211> LENGTH: 6
<212> TYPE: PRT
<213> ORGANISM: Artificial Sequence
<220> FEATURE:
<223> OTHER INFORMATION: Synthetic

<400> SEQUENCE: 269

Gln Ala Ile Asn Asn Phe
 1               5

<210> SEQ ID NO 270
<211> LENGTH: 9
<212> TYPE: DNA
<213> ORGANISM: Artificial Sequence
<220> FEATURE:
<223> OTHER INFORMATION: Synthetic

<400> SEQUENCE: 270 gctacatcc                                                                 9

<210> SEQ ID NO 271
<211> LENGTH: 3
<212> TYPE: PRT
<213> ORGANISM: Artificial Sequence
<220> FEATURE:
<223> OTHER INFORMATION: Synthetic

<400> SEQUENCE: 271

Ala Thr Ser
 1

<210> SEQ ID NO 272
<211> LENGTH: 27
<212> TYPE: DNA
<213> ORGANISM: Artificial Sequence
<220> FEATURE:
<223> OTHER INFORMATION: Synthetic

<400> SEQUENCE: 272
cagcagtata atagtcaccc gtggacg                                            27

<210> SEQ ID NO 273
<211> LENGTH: 9
<212> TYPE: PRT
<213> ORGANISM: Artificial Sequence
<220> FEATURE:
<223> OTHER INFORMATION: Synthetic

<400> SEQUENCE: 273

Gln Gln Tyr Asn Ser His Pro Trp Thr
 1               5

<210> SEQ ID NO 274
<211> LENGTH: 357
<212> TYPE: DNA
<213> ORGANISM: Artificial Sequence
<220> FEATURE:
<223> OTHER INFORMATION: Synthetic
```

-continued

<400> SEQUENCE: 274

```
caggtgcgac tggtggagtc tgggggaggc gtggtccagc ctggagggtc cctgagactc      60
tcctgtactg cctctggatt catcttcaga agttatggca tgcactgggt ccgccaggct     120
ccaggcaggg gactggagtg ggtggcagtc atatcatatg atggcagtaa aacattctac     180
gtagattccg tgaaggtccg attcaccatc tccagagaca actccaagaa cacgctttat     240
ttggagatga acagcctgag agttgacgac acggctgtat atttctgtgt gaaagaagga     300
agaagtggga gttggttcga cccctgggggc cagggaaccc tggtcgccgt ctcctca      357
```

<210> SEQ ID NO 275
<211> LENGTH: 119
<212> TYPE: PRT
<213> ORGANISM: Artificial Sequence
<220> FEATURE:
<223> OTHER INFORMATION: Synthetic

<400> SEQUENCE: 275

```
Gln Val Arg Leu Val Glu Ser Gly Gly Gly Val Val Gln Pro Gly Gly
 1               5                  10                  15

Ser Leu Arg Leu Ser Cys Thr Ala Ser Gly Phe Ile Phe Arg Ser Tyr
            20                  25                  30

Gly Met His Trp Val Arg Gln Ala Pro Gly Arg Gly Leu Glu Trp Val
        35                  40                  45

Ala Val Ile Ser Tyr Asp Gly Ser Lys Thr Phe Tyr Val Asp Ser Val
    50                  55                  60

Lys Val Arg Phe Thr Ile Ser Arg Asp Asn Ser Lys Asn Thr Leu Tyr
65                  70                  75                  80

Leu Glu Met Asn Ser Leu Arg Val Asp Asp Thr Ala Val Tyr Phe Cys
                85                  90                  95

Val Lys Glu Gly Arg Ser Gly Ser Trp Phe Asp Pro Trp Gly Gln Gly
            100                 105                 110

Thr Leu Val Ala Val Ser Ser
        115
```

<210> SEQ ID NO 276
<211> LENGTH: 24
<212> TYPE: DNA
<213> ORGANISM: Artificial Sequence
<220> FEATURE:
<223> OTHER INFORMATION: Synthetic

<400> SEQUENCE: 276

```
ggattcatct tcagaagtta tggc                                              24
```

<210> SEQ ID NO 277
<211> LENGTH: 8
<212> TYPE: PRT
<213> ORGANISM: Artificial Sequence
<220> FEATURE:
<223> OTHER INFORMATION: Synthetic

<400> SEQUENCE: 277

```
Gly Phe Ile Phe Arg Ser Tyr Gly
 1               5
```

<210> SEQ ID NO 278
<211> LENGTH: 24
<212> TYPE: DNA
<213> ORGANISM: Artificial Sequence

```
<220> FEATURE:
<223> OTHER INFORMATION: Synthetic

<400> SEQUENCE: 278
atatcatatg atggcagtaa aaca                                          24

<210> SEQ ID NO 279
<211> LENGTH: 8
<212> TYPE: PRT
<213> ORGANISM: Artificial Sequence
<220> FEATURE:
<223> OTHER INFORMATION: Synthetic

<400> SEQUENCE: 279

Ile Ser Tyr Asp Gly Ser Lys Thr
1               5

<210> SEQ ID NO 280
<211> LENGTH: 36
<212> TYPE: DNA
<213> ORGANISM: Artificial Sequence
<220> FEATURE:
<223> OTHER INFORMATION: Synthetic

<400> SEQUENCE: 280
gtgaaagaag gaagaagtgg gagttggttc gacccc                             36

<210> SEQ ID NO 281
<211> LENGTH: 12
<212> TYPE: PRT
<213> ORGANISM: Artificial Sequence
<220> FEATURE:
<223> OTHER INFORMATION: Synthetic

<400> SEQUENCE: 281

Val Lys Glu Gly Arg Ser Gly Ser Trp Phe Asp Pro
1               5                   10

<210> SEQ ID NO 282
<211> LENGTH: 321
<212> TYPE: DNA
<213> ORGANISM: Artificial Sequence
<220> FEATURE:
<223> OTHER INFORMATION: Synthetic

<400> SEQUENCE: 282
gacatccaca tgacccagtc tccatcctca ctgtctgcgt ctgtaggaga cagagtcacc    60
atcacttgtc gggcgagtca ggccattaac aattttttag cctggtttca gcagaaacca   120
gggaaaaccc ctaagtccct gatctttgct catccagtt tacaaagtgg ggtcccatca    180
aggttcagcg gcagtggatc tgggacagac ttcactctca ccatcagcag cctgcagcct   240
gaagattttg caacttatta ctgccaacag tataatagtc acccgtggac gttcggccaa   300
gggaccaagg tggaaatcag a                                            321

<210> SEQ ID NO 283
<211> LENGTH: 107
<212> TYPE: PRT
<213> ORGANISM: Artificial Sequence
<220> FEATURE:
<223> OTHER INFORMATION: Synthetic

<400> SEQUENCE: 283

Asp Ile His Met Thr Gln Ser Pro Ser Ser Leu Ser Ala Ser Val Gly
1               5                   10                  15
```

```
Asp Arg Val Thr Ile Thr Cys Arg Ala Ser Gln Ala Ile Asn Asn Phe
            20                  25                  30

Leu Ala Trp Phe Gln Gln Lys Pro Gly Lys Thr Pro Lys Ser Leu Ile
        35                  40                  45

Phe Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Arg
            100                 105
```

<210> SEQ ID NO 284
<211> LENGTH: 18
<212> TYPE: DNA
<213> ORGANISM: Artificial Sequence
<220> FEATURE:
<223> OTHER INFORMATION: Synthetic

<400> SEQUENCE: 284
caggccatta acaatttt                                                18

<210> SEQ ID NO 285
<211> LENGTH: 6
<212> TYPE: PRT
<213> ORGANISM: Artificial Sequence
<220> FEATURE:
<223> OTHER INFORMATION: Synthetic

<400> SEQUENCE: 285

```
Gln Ala Ile Asn Asn Phe
1               5
```

<210> SEQ ID NO 286
<211> LENGTH: 9
<212> TYPE: DNA
<213> ORGANISM: Artificial Sequence
<220> FEATURE:
<223> OTHER INFORMATION: Synthetic

<400> SEQUENCE: 286 gctacatcc                                                           9

<210> SEQ ID NO 287
<211> LENGTH: 3
<212> TYPE: PRT
<213> ORGANISM: Artificial Sequence
<220> FEATURE:
<223> OTHER INFORMATION: Synthetic

<400> SEQUENCE: 287

```
Ala Thr Ser
1
```

<210> SEQ ID NO 288
<211> LENGTH: 27
<212> TYPE: DNA
<213> ORGANISM: Artificial Sequence
<220> FEATURE:
<223> OTHER INFORMATION: Synthetic

<400> SEQUENCE: 288
caacagtata atagtcaccc gtggacg 27

<210> SEQ ID NO 289
<211> LENGTH: 9
<212> TYPE: PRT
<213> ORGANISM: Artificial Sequence
<220> FEATURE:
<223> OTHER INFORMATION: Synthetic

<400> SEQUENCE: 289

Gln Gln Tyr Asn Ser His Pro Trp Thr
1               5

<210> SEQ ID NO 290
<211> LENGTH: 357
<212> TYPE: DNA
<213> ORGANISM: Artificial Sequence
<220> FEATURE:
<223> OTHER INFORMATION: Synthetic

<400> SEQUENCE: 290
caggtgcgac tggtggagtc tgggggaggc gtggtccagc ctggagggtc cctgagactc      60
tcctgtgctg cctctggatt catcttcaga agctatggca tgcactgggt ccgccaggct     120
ccaggcaggg gactggagtg ggtggcagtc atatcatatg atggcagtaa aacattctac     180
gtagattccg tgaaggtccg attcaccata tccagagaca actccaagaa cacgctttat     240
ttggaaatga acagcctgag agttgacgac acggctgtat atttctgtgt gaaagaagga     300
agaagtggga gttggttcga cccctggggc cagggaaccc tggtcgccgt ctcctca       357

<210> SEQ ID NO 291
<211> LENGTH: 119
<212> TYPE: PRT
<213> ORGANISM: Artificial Sequence
<220> FEATURE:
<223> OTHER INFORMATION: Synthetic

<400> SEQUENCE: 291

Gln Val Arg Leu Val Glu Ser Gly Gly Gly Val Val Gln Pro Gly Gly
1               5                   10                  15

Ser Leu Arg Leu Ser Cys Ala Ala Ser Gly Phe Ile Phe Arg Ser Tyr
            20                  25                  30

Gly Met His Trp Val Arg Gln Ala Pro Gly Arg Gly Leu Glu Trp Val
        35                  40                  45

Ala Val Ile Ser Tyr Asp Gly Ser Lys Thr Phe Tyr Val Asp Ser Val
    50                  55                  60

Lys Val Arg Phe Thr Ile Ser Arg Asp Asn Ser Lys Asn Thr Leu Tyr
65                  70                  75                  80

Leu Glu Met Asn Ser Leu Arg Val Asp Asp Thr Ala Val Tyr Phe Cys
                85                  90                  95

Val Lys Glu Gly Arg Ser Gly Ser Trp Phe Asp Pro Trp Gly Gln Gly
            100                 105                 110

Thr Leu Val Ala Val Ser Ser
        115

<210> SEQ ID NO 292
<211> LENGTH: 24
<212> TYPE: DNA
<213> ORGANISM: Artificial Sequence
<220> FEATURE:
<223> OTHER INFORMATION: Synthetic

```
<400> SEQUENCE: 292
ggattcatct tcagaagcta tggc                                              24

<210> SEQ ID NO 293
<211> LENGTH: 8
<212> TYPE: PRT
<213> ORGANISM: Artificial Sequence
<220> FEATURE:
<223> OTHER INFORMATION: Synthetic

<400> SEQUENCE: 293

Gly Phe Ile Phe Arg Ser Tyr Gly
 1               5

<210> SEQ ID NO 294
<211> LENGTH: 24
<212> TYPE: DNA
<213> ORGANISM: Artificial Sequence
<220> FEATURE:
<223> OTHER INFORMATION: Synthetic

<400> SEQUENCE: 294
atatcatatg atggcagtaa aaca                                              24

<210> SEQ ID NO 295
<211> LENGTH: 8
<212> TYPE: PRT
<213> ORGANISM: Artificial Sequence
<220> FEATURE:
<223> OTHER INFORMATION: Synthetic

<400> SEQUENCE: 295

Ile Ser Tyr Asp Gly Ser Lys Thr
 1               5

<210> SEQ ID NO 296
<211> LENGTH: 36
<212> TYPE: DNA
<213> ORGANISM: Artificial Sequence
<220> FEATURE:
<223> OTHER INFORMATION: Synthetic

<400> SEQUENCE: 296
gtgaaagaag gaagaagtgg gagttggttc gacccc                                 36

<210> SEQ ID NO 297
<211> LENGTH: 12
<212> TYPE: PRT
<213> ORGANISM: Artificial Sequence
<220> FEATURE:
<223> OTHER INFORMATION: Synthetic

<400> SEQUENCE: 297

Val Lys Glu Gly Arg Ser Gly Ser Trp Phe Asp Pro
 1               5                  10

<210> SEQ ID NO 298
<211> LENGTH: 321
<212> TYPE: DNA
<213> ORGANISM: Artificial Sequence
<220> FEATURE:
<223> OTHER INFORMATION: Synthetic

<400> SEQUENCE: 298
gacatccaca tgacccagtc tccatcctca ctgtctgcgt ctgtaggaga cagagtcacc       60
```

-continued

| | |
|---|---|
| atcacttgtc gggcgagtca ggccattaac aatttttag cctggtttca gcagaaacca | 120 |
| gggaaaaccc ctaagtccct gatctttgct acatccagtt tacaaagtgg ggtcccatca | 180 |
| aggttcagcg gcagtggatc tgggacagac ttcactctca ccatcagcag cctgcagcct | 240 |
| gaagattttg caactattta ctgccaacag tataatagtc acccgtggac gttcggccaa | 300 |
| gggaccaagg tggaaatcaa a | 321 |

<210> SEQ ID NO 299
<211> LENGTH: 107
<212> TYPE: PRT
<213> ORGANISM: Artificial Sequence
<220> FEATURE:
<223> OTHER INFORMATION: Synthetic

<400> SEQUENCE: 299

Asp Ile His Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn Phe
            20                  25                  30

Leu Ala Trp Phe Gln Gln Lys Pro Gly Lys Thr Pro Lys Ser Leu Ile
        35                  40                  45

Phe Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys
            100                 105

<210> SEQ ID NO 300
<211> LENGTH: 18
<212> TYPE: DNA
<213> ORGANISM: Artificial Sequence
<220> FEATURE:
<223> OTHER INFORMATION: Synthetic

<400> SEQUENCE: 300

| | |
|---|---|
| caggccatta acaattt | 18 |

<210> SEQ ID NO 301
<211> LENGTH: 6
<212> TYPE: PRT
<213> ORGANISM: Artificial Sequence
<220> FEATURE:
<223> OTHER INFORMATION: Synthetic

<400> SEQUENCE: 301

Gln Ala Ile Asn Asn Phe
1               5

<210> SEQ ID NO 302
<211> LENGTH: 9
<212> TYPE: DNA
<213> ORGANISM: Artificial Sequence
<220> FEATURE:
<223> OTHER INFORMATION: Synthetic

<400> SEQUENCE: 302

| | |
|---|---|
| gctacatcc | 9 |

<210> SEQ ID NO 303
<211> LENGTH: 3
<212> TYPE: PRT
<213> ORGANISM: Artificial Sequence
<220> FEATURE:
<223> OTHER INFORMATION: Synthetic

<400> SEQUENCE: 303

Ala Thr Ser
 1

<210> SEQ ID NO 304
<211> LENGTH: 27
<212> TYPE: DNA
<213> ORGANISM: Artificial Sequence
<220> FEATURE:
<223> OTHER INFORMATION: Synthetic

<400> SEQUENCE: 304
caacagtata atagtcaccc gtggacg                                         27

<210> SEQ ID NO 305
<211> LENGTH: 9
<212> TYPE: PRT
<213> ORGANISM: Artificial Sequence
<220> FEATURE:
<223> OTHER INFORMATION: Synthetic

<400> SEQUENCE: 305

Gln Gln Tyr Asn Ser His Pro Trp Thr
 1               5

<210> SEQ ID NO 306
<211> LENGTH: 354
<212> TYPE: DNA
<213> ORGANISM: Artificial Sequence
<220> FEATURE:
<223> OTHER INFORMATION: Synthetic

<400> SEQUENCE: 306
caggtgcagc tggtggagtc tgggggaggc gtggtccagc ctggggaggtc cctgagactc      60 tcctgtgcag cctctggatt caccttcagt agctatggca tgcactgggt ccgccaggct     120
ccaggcaagg gtctggagtg ggtgacagtt atatcatatg atggaagtat taaatattat     180
gtagactccg tgaagggccg attcaccatc tccagagaca attccaagaa cacgctgttt     240
ctgcaaatga atagcctgcg agttgaggac acggctgtgt attactgtgc gaaggaaggt     300
aggaagtacg gtatggacgt ctggggccaa gggaccacgg tcaccgtctc ctca           354

<210> SEQ ID NO 307
<211> LENGTH: 118
<212> TYPE: PRT
<213> ORGANISM: Artificial Sequence
<220> FEATURE:
<223> OTHER INFORMATION: Synthetic

<400> SEQUENCE: 307

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Thr Val Ile Ser Tyr Asp Gly Ser Ile Lys Tyr Tyr Val Asp Ser Val

```
            50                  55                  60
Lys Gly Arg Phe Thr Ile Ser Arg Asp Asn Ser Lys Asn Thr Leu Phe
 65                  70                  75                  80

Leu Gln Met Asn Ser Leu Arg Val Glu Asp Thr Ala Val Tyr Tyr Cys
                 85                  90                  95

Ala Lys Glu Gly Arg Lys Tyr Gly Met Asp Val Trp Gly Gln Gly Thr
            100                 105                 110

Thr Val Thr Val Ser Ser
        115
```

<210> SEQ ID NO 308
<211> LENGTH: 24
<212> TYPE: DNA
<213> ORGANISM: Artificial Sequence
<220> FEATURE:
<223> OTHER INFORMATION: Synthetic

<400> SEQUENCE: 308
ggattcacct tcagtagcta tggc                                    24

<210> SEQ ID NO 309
<211> LENGTH: 8
<212> TYPE: PRT
<213> ORGANISM: Artificial Sequence
<220> FEATURE:
<223> OTHER INFORMATION: Synthetic

<400> SEQUENCE: 309

```
Gly Phe Thr Phe Ser Ser Tyr Gly
 1               5
```

<210> SEQ ID NO 310
<211> LENGTH: 24
<212> TYPE: DNA
<213> ORGANISM: Artificial Sequence
<220> FEATURE:
<223> OTHER INFORMATION: Synthetic

<400> SEQUENCE: 310
atatcatatg atggaagtat taaa                                    24

<210> SEQ ID NO 311
<211> LENGTH: 8
<212> TYPE: PRT
<213> ORGANISM: Artificial Sequence
<220> FEATURE:
<223> OTHER INFORMATION: Synthetic

<400> SEQUENCE: 311

```
Ile Ser Tyr Asp Gly Ser Ile Lys
 1               5
```

<210> SEQ ID NO 312
<211> LENGTH: 33
<212> TYPE: DNA
<213> ORGANISM: Artificial Sequence
<220> FEATURE:
<223> OTHER INFORMATION: Synthetic

<400> SEQUENCE: 312
gcgaaggaag gtaggaagta cggtatggac gtc                          33

<210> SEQ ID NO 313
<211> LENGTH: 11

<212> TYPE: PRT
<213> ORGANISM: Artificial Sequence
<220> FEATURE:
<223> OTHER INFORMATION: Synthetic

<400> SEQUENCE: 313

Ala Lys Glu Gly Arg Lys Tyr Gly Met Asp Val
1               5                   10

<210> SEQ ID NO 314
<211> LENGTH: 321
<212> TYPE: DNA
<213> ORGANISM: Artificial Sequence
<220> FEATURE:
<223> OTHER INFORMATION: Synthetic

<400> SEQUENCE: 314
gacatccaga tgacccagtc tccttccacc ctgtctgcat ctgtaggaga cagagtcacc      60
atcacttgcc gggccagtca gattattagt agcttattgg tctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tatcatagtt acatgtacac ttttggccag    300
gggaccaagc tggagatcaa a                                              321

<210> SEQ ID NO 315
<211> LENGTH: 107
<212> TYPE: PRT
<213> ORGANISM: Artificial Sequence
<220> FEATURE:
<223> OTHER INFORMATION: Synthetic

<400> SEQUENCE: 315

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ile Ile Ser Ser Leu
            20                  25                  30

Leu Val Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Tyr Met Tyr
                85                  90                  95

Thr Phe Gly Gln Gly Thr Lys Leu Glu Ile Lys
            100                 105

<210> SEQ ID NO 316
<211> LENGTH: 18
<212> TYPE: DNA
<213> ORGANISM: Artificial Sequence
<220> FEATURE:
<223> OTHER INFORMATION: Synthetic

<400> SEQUENCE: 316
cagattatta gtagctta                                                   18

<210> SEQ ID NO 317
<211> LENGTH: 6
<212> TYPE: PRT

<210> SEQ ID NO 317
<211> LENGTH: 5
<212> TYPE: PRT
<213> ORGANISM: Artificial Sequence
<220> FEATURE:
<223> OTHER INFORMATION: Synthetic

<400> SEQUENCE: 317

Gln Ile Ile Ser Ser Leu
 1               5

<210> SEQ ID NO 318
<211> LENGTH: 9
<212> TYPE: DNA
<213> ORGANISM: Artificial Sequence
<220> FEATURE:
<223> OTHER INFORMATION: Synthetic

<400> SEQUENCE: 318 aaggcgtct                                                                  9

<210> SEQ ID NO 319
<211> LENGTH: 3
<212> TYPE: PRT
<213> ORGANISM: Artificial Sequence
<220> FEATURE:
<223> OTHER INFORMATION: Synthetic

<400> SEQUENCE: 319

Lys Ala Ser
 1

<210> SEQ ID NO 320
<211> LENGTH: 27
<212> TYPE: DNA
<213> ORGANISM: Artificial Sequence
<220> FEATURE:
<223> OTHER INFORMATION: Synthetic

<400> SEQUENCE: 320
caacagtatc atagttacat gtacact                                             27

<210> SEQ ID NO 321
<211> LENGTH: 9
<212> TYPE: PRT
<213> ORGANISM: Artificial Sequence
<220> FEATURE:
<223> OTHER INFORMATION: Synthetic

<400> SEQUENCE: 321

Gln Gln Tyr His Ser Tyr Met Tyr Thr
 1               5

<210> SEQ ID NO 322
<211> LENGTH: 357
<212> TYPE: DNA
<213> ORGANISM: Artificial Sequence
<220> FEATURE:
<223> OTHER INFORMATION: Synthetic

<400> SEQUENCE: 322
caggtgcagc tggtggagtc tgggggaggc gtggtccagc ctggggaggtc cctgagactc        60 tcctgtacag cctctggatt caccttcagt agctttggca tgcactgggt ccgccaggct       120
ccaggcaggg gactggagtg ggtggcagtt atatcatatg atggcagtaa aaatactac        180 gcagactccg tgaaggtccg attcaccatc tccagagaca actccaagaa cacgctttat       240
ctgcaaatga acagcctgag agttgacgac acggctgtgt atttctgtgc gaaagaagga       300

```
agaactggga attggttcga ccctgggggc cagggaccc tggtcgccgt ctcctca      357
```

<210> SEQ ID NO 323
<211> LENGTH: 119
<212> TYPE: PRT
<213> ORGANISM: Artificial Sequence
<220> FEATURE:
<223> OTHER INFORMATION: Synthetic

<400> SEQUENCE: 323

```
Gln Val Gln Leu Val Glu Ser Gly Gly Gly Val Val Gln Pro Gly Arg
  1               5                  10                  15

Ser Leu Arg Leu Ser Cys Thr Ala Ser Gly Phe Thr Phe Ser Ser Phe
             20                  25                  30

Gly Met His Trp Val Arg Gln Ala Pro Gly Arg Gly Leu Glu Trp Val
         35                  40                  45

Ala Val Ile Ser Tyr Asp Gly Ser Lys Lys Tyr Tyr Ala Asp Ser Val
     50                  55                  60

Lys Val Arg Phe Thr Ile Ser Arg Asp Asn Ser Lys Asn Thr Leu Tyr
 65                  70                  75                  80

Leu Gln Met Asn Ser Leu Arg Val Asp Asp Thr Ala Val Tyr Phe Cys
                 85                  90                  95

Ala Lys Glu Gly Arg Thr Gly Asn Trp Phe Asp Pro Trp Gly Gln Gly
            100                 105                 110

Thr Leu Val Ala Val Ser Ser
        115
```

<210> SEQ ID NO 324
<211> LENGTH: 24
<212> TYPE: DNA
<213> ORGANISM: Artificial Sequence
<220> FEATURE:
<223> OTHER INFORMATION: Synthetic

<400> SEQUENCE: 324

```
ggattcacct tcagtagctt tggc                                          24
```

<210> SEQ ID NO 325
<211> LENGTH: 8
<212> TYPE: PRT
<213> ORGANISM: Artificial Sequence
<220> FEATURE:
<223> OTHER INFORMATION: Synthetic

<400> SEQUENCE: 325

```
Gly Phe Thr Phe Ser Ser Phe Gly
  1               5
```

<210> SEQ ID NO 326
<211> LENGTH: 24
<212> TYPE: DNA
<213> ORGANISM: Artificial Sequence
<220> FEATURE:
<223> OTHER INFORMATION: Synthetic

<400> SEQUENCE: 326

```
atatcatatg atggcagtaa aaaa                                          24
```

<210> SEQ ID NO 327
<211> LENGTH: 8
<212> TYPE: PRT
<213> ORGANISM: Artificial Sequence
<220> FEATURE:

<223> OTHER INFORMATION: Synthetic

<400> SEQUENCE: 327

Ile Ser Tyr Asp Gly Ser Lys Lys
1               5

<210> SEQ ID NO 328
<211> LENGTH: 36
<212> TYPE: DNA
<213> ORGANISM: Artificial Sequence
<220> FEATURE:
<223> OTHER INFORMATION: Synthetic

<400> SEQUENCE: 328
gcgaaagaag gaagaactgg gaattggttc gacccc        36

<210> SEQ ID NO 329
<211> LENGTH: 12
<212> TYPE: PRT
<213> ORGANISM: Artificial Sequence
<220> FEATURE:
<223> OTHER INFORMATION: Synthetic

<400> SEQUENCE: 329

Ala Lys Glu Gly Arg Thr Gly Asn Trp Phe Asp Pro
1               5                   10

<210> SEQ ID NO 330
<211> LENGTH: 321
<212> TYPE: DNA
<213> ORGANISM: Artificial Sequence
<220> FEATURE:
<223> OTHER INFORMATION: Synthetic

<400> SEQUENCE: 330
gacatccaga tgacccagtc tccatcctca ctgtctgcat ctgtaggaga cagagtcacc        60
atcacttgtc gggcgagtca ggccattaac aattatttag cctggtttca gcagaaacca       120
gggaaaaccc ctaagtccct gatctttgct acatccagtt tacaaagtgg ggtcccatca       180
aggttcagcg gcactggatc tgggacagac ttcactctca ccatcagcag cctgcagcct       240
gaagattttg caacttatta ctgccaacag tataatagtc acccgtggac gttcggccaa       300
gggaccaagg tggaaatcag a                                                 321

<210> SEQ ID NO 331
<211> LENGTH: 107
<212> TYPE: PRT
<213> ORGANISM: Artificial Sequence
<220> FEATURE:
<223> OTHER INFORMATION: Synthetic

<400> SEQUENCE: 331

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn Tyr
            20                  25                  30

Leu Ala Trp Phe Gln Gln Lys Pro Gly Lys Thr Pro Lys Ser Leu Ile
        35                  40                  45

Phe Ala Thr Ser Ser Leu Gln Ser Gly Val Pro Ser Arg Phe Ser Gly
    50                  55                  60

Thr Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Asn Ser His Pro Trp
                85                  90                  95
Thr Phe Gly Gln Gly Thr Lys Val Glu Ile Arg
            100                 105

<210> SEQ ID NO 332
<211> LENGTH: 18
<212> TYPE: DNA
<213> ORGANISM: Artificial Sequence
<220> FEATURE:
<223> OTHER INFORMATION: Synthetic

<400> SEQUENCE: 332
caggccatta acaattat                                                 18

<210> SEQ ID NO 333
<211> LENGTH: 6
<212> TYPE: PRT
<213> ORGANISM: Artificial Sequence
<220> FEATURE:
<223> OTHER INFORMATION: Synthetic

<400> SEQUENCE: 333

Gln Ala Ile Asn Asn Tyr
 1               5

<210> SEQ ID NO 334
<211> LENGTH: 9
<212> TYPE: DNA
<213> ORGANISM: Artificial Sequence
<220> FEATURE:
<223> OTHER INFORMATION: Synthetic

<400> SEQUENCE: 334 gctacatcc                                                            9

<210> SEQ ID NO 335
<211> LENGTH: 3
<212> TYPE: PRT
<213> ORGANISM: Artificial Sequence
<220> FEATURE:
<223> OTHER INFORMATION: Synthetic

<400> SEQUENCE: 335

Ala Thr Ser
 1

<210> SEQ ID NO 336
<211> LENGTH: 27
<212> TYPE: DNA
<213> ORGANISM: Artificial Sequence
<220> FEATURE:
<223> OTHER INFORMATION: Synthetic

<400> SEQUENCE: 336
caacagtata atagtcaccc gtggacg                                       27

<210> SEQ ID NO 337
<211> LENGTH: 9
<212> TYPE: PRT
<213> ORGANISM: Artificial Sequence
<220> FEATURE:
<223> OTHER INFORMATION: Synthetic

<400> SEQUENCE: 337

Gln Gln Tyr Asn Ser His Pro Trp Thr
```

<210> SEQ ID NO 338
<211> LENGTH: 357
<212> TYPE: DNA
<213> ORGANISM: Artificial Sequence
<220> FEATURE:
<223> OTHER INFORMATION: Synthetic

<400> SEQUENCE: 338

```
caggtgcgac tggtggagtc tgggggaggc gtggtccagc ctggaaggtc cctgagactc    60
tcctgtgtag cctctggatt caccttcaga agttatggca tgcactgggt ccgccaggct   120
ccaggcaggg gactggagtg ggtggcagtc atatcatatg atggcagtca aacattctat   180
gtagattccg tgaaggtccg attcaccatc tccagagaca actccaacaa cacgctttat   240
ttggaaatga acagcctgag agttgacgac acggctgttt atttctgtgt gaaagaagga   300
agaagtggga gttggttcga ccctgggggc cagggaaccc tggtcgccgt ctcctca     357
```

<210> SEQ ID NO 339
<211> LENGTH: 119
<212> TYPE: PRT
<213> ORGANISM: Artificial Sequence
<220> FEATURE:
<223> OTHER INFORMATION: Synthetic

<400> SEQUENCE: 339

```
Gln Val Arg Leu Val Glu Ser Gly Gly Gly Val Val Gln Pro Gly Arg
 1               5                  10                  15
Ser Leu Arg Leu Ser Cys Val Ala Ser Gly Phe Thr Phe Arg Ser Tyr
            20                  25                  30
Gly Met His Trp Val Arg Gln Ala Pro Gly Arg Gly Leu Glu Trp Val
        35                  40                  45
Ala Val Ile Ser Tyr Asp Gly Ser Gln Thr Phe Tyr Val Asp Ser Val
    50                  55                  60
Lys Val Arg Phe Thr Ile Ser Arg Asp Asn Ser Asn Asn Thr Leu Tyr
65                  70                  75                  80
Leu Glu Met Asn Ser Leu Arg Val Asp Asp Thr Ala Val Tyr Phe Cys
                85                  90                  95
Val Lys Glu Gly Arg Ser Gly Ser Trp Phe Asp Pro Trp Gly Gln Gly
            100                 105                 110
Thr Leu Val Ala Val Ser Ser
        115
```

<210> SEQ ID NO 340
<211> LENGTH: 24
<212> TYPE: DNA
<213> ORGANISM: Artificial Sequence
<220> FEATURE:
<223> OTHER INFORMATION: Synthetic

<400> SEQUENCE: 340

```
ggattcacct tcagaagtta tggc                                           24
```

<210> SEQ ID NO 341
<211> LENGTH: 8
<212> TYPE: PRT
<213> ORGANISM: Artificial Sequence
<220> FEATURE:
<223> OTHER INFORMATION: Synthetic

<400> SEQUENCE: 341

```
Gly Phe Thr Phe Arg Ser Tyr Gly
 1               5

<210> SEQ ID NO 342
<211> LENGTH: 24
<212> TYPE: DNA
<213> ORGANISM: Artificial Sequence
<220> FEATURE:
<223> OTHER INFORMATION: Synthetic

<400> SEQUENCE: 342
atatcatatg atggcagtca aaca                                          24

<210> SEQ ID NO 343
<211> LENGTH: 8
<212> TYPE: PRT
<213> ORGANISM: Artificial Sequence
<220> FEATURE:
<223> OTHER INFORMATION: Synthetic

<400> SEQUENCE: 343

Ile Ser Tyr Asp Gly Ser Gln Thr
 1               5

<210> SEQ ID NO 344
<211> LENGTH: 36
<212> TYPE: DNA
<213> ORGANISM: Artificial Sequence
<220> FEATURE:
<223> OTHER INFORMATION: Synthetic

<400> SEQUENCE: 344
gtgaaagaag aagaagtgg gagttggttc gacccc                              36

<210> SEQ ID NO 345
<211> LENGTH: 12
<212> TYPE: PRT
<213> ORGANISM: Artificial Sequence
<220> FEATURE:
<223> OTHER INFORMATION: Synthetic

<400> SEQUENCE: 345

Val Lys Glu Gly Arg Ser Gly Ser Trp Phe Asp Pro
 1               5                  10

<210> SEQ ID NO 346
<211> LENGTH: 321
<212> TYPE: DNA
<213> ORGANISM: Artificial Sequence
<220> FEATURE:
<223> OTHER INFORMATION: Synthetic

<400> SEQUENCE: 346
gacatccaca tgacccagtc tccatcctca ctgtctgcgt ctgttggaga cagagtcacc    60
atcacttgtc gggcgagtca ggccattaat aattatttag cctggtttca gcagaaacca   120
gggagaaccc ctaagtccct gatctttgct acatccagtt tacaaagtgg ggtcccatca   180
aggttcagcg gcagtggatc tgggacagac ttcactctca ccatcagcag cctgcagcct   240
gaagattttg caacttatta ctgccaacag tataatagtc acccgtggac gttcggccaa   300
gggaccaagg tggaaatcaa a                                             321

<210> SEQ ID NO 347
<211> LENGTH: 107
```

```
<212> TYPE: PRT
<213> ORGANISM: Artificial Sequence
<220> FEATURE:
<223> OTHER INFORMATION: Synthetic

<400> SEQUENCE: 347

Asp Ile His Met Thr Gln Ser Pro Ser Ser Leu Ser Ala Ser Val Gly
1               5                   10                  15
Asp Arg Val Thr Ile Thr Cys Arg Ala Ser Gln Ala Ile Asn Asn Tyr
            20                  25                  30
Leu Ala Trp Phe Gln Gln Lys Pro Gly Arg Thr Pro Lys Ser Leu Ile
        35                  40                  45
Phe Ala Thr Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser His Pro Trp
                85                  90                  95
Thr Phe Gly Gln Gly Thr Lys Val Glu Ile Lys
            100                 105

<210> SEQ ID NO 348
<211> LENGTH: 18
<212> TYPE: DNA
<213> ORGANISM: Artificial Sequence
<220> FEATURE:
<223> OTHER INFORMATION: Synthetic

<400> SEQUENCE: 348
caggccatta ataattat                                                   18

<210> SEQ ID NO 349
<211> LENGTH: 6
<212> TYPE: PRT
<213> ORGANISM: Artificial Sequence
<220> FEATURE:
<223> OTHER INFORMATION: Synthetic

<400> SEQUENCE: 349

Gln Ala Ile Asn Asn Tyr
1               5

<210> SEQ ID NO 350
<211> LENGTH: 9
<212> TYPE: DNA
<213> ORGANISM: Artificial Sequence
<220> FEATURE:
<223> OTHER INFORMATION: Synthetic

<400> SEQUENCE: 350 gctacatcc                                                              9

<210> SEQ ID NO 351
<211> LENGTH: 3
<212> TYPE: PRT
<213> ORGANISM: Artificial Sequence
<220> FEATURE:
<223> OTHER INFORMATION: Synthetic

<400> SEQUENCE: 351

Ala Thr Ser
1
```

<210> SEQ ID NO 352
<211> LENGTH: 27
<212> TYPE: DNA
<213> ORGANISM: Artificial Sequence
<220> FEATURE:
<223> OTHER INFORMATION: Synthetic

<400> SEQUENCE: 352
caacagtata atagtcaccc gtggacg					27

<210> SEQ ID NO 353
<211> LENGTH: 9
<212> TYPE: PRT
<213> ORGANISM: Artificial Sequence
<220> FEATURE:
<223> OTHER INFORMATION: Synthetic

<400> SEQUENCE: 353

Gln Gln Tyr Asn Ser His Pro Trp Thr
 1               5

<210> SEQ ID NO 354
<211> LENGTH: 354
<212> TYPE: DNA
<213> ORGANISM: Artificial Sequence
<220> FEATURE:
<223> OTHER INFORMATION: Synthetic

<400> SEQUENCE: 354
caggtgcagt tggtggagtc agggggaggc gtggtccagc ctgggaggtc cctgagactc		60 tcctgtgcag cctctggatt caccttcagt agttatgcca tgtactgggt ccgccaggct		120 ccaggcaagg ggctggagtg ggtggcagtg atatcatatg atggaagtaa taaatactat		180 acagactccg tgaagggccg attcaccgtc tccagagaca attccaaaaa cacgctgttt		240 ctgcaaatga acagcctgag agctgaggac acggctctgt attactgtgc gaaagaaagt		300 tcttcgtacg gtttggacgt ctggggtcaa gggaccacgg tcaccgtctc ctca		354

<210> SEQ ID NO 355
<211> LENGTH: 118
<212> TYPE: PRT
<213> ORGANISM: Artificial Sequence
<220> FEATURE:
<223> OTHER INFORMATION: Synthetic

<400> SEQUENCE: 355

Gln Val Gln Leu Val Glu Ser Gly Gly Gly Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met Tyr Trp Val Arg Gln Ala Pro Gly Lys Gly Leu Glu Trp Val
            35                  40                  45

Ala Val Ile Ser Tyr Asp Gly Ser Asn Lys Tyr Tyr Thr Asp Ser Val
        50                  55                  60

Lys Gly Arg Phe Thr Val Ser Arg Asp Asn Ser Lys Asn Thr Leu Phe
65                  70                  75                  80

Leu Gln Met Asn Ser Leu Arg Ala Glu Asp Thr Ala Leu Tyr Tyr Cys
                85                  90                  95

Ala Lys Glu Ser Ser Ser Tyr Gly Leu Asp Val Trp Gly Gln Gly Thr
            100                 105                 110

Thr Val Thr Val Ser Ser
        115

```
<210> SEQ ID NO 356
<211> LENGTH: 24
<212> TYPE: DNA
<213> ORGANISM: Artificial Sequence
<220> FEATURE:
<223> OTHER INFORMATION: Synthetic

<400> SEQUENCE: 356
ggattcacct tcagtagtta tgcc                                               24

<210> SEQ ID NO 357
<211> LENGTH: 8
<212> TYPE: PRT
<213> ORGANISM: Artificial Sequence
<220> FEATURE:
<223> OTHER INFORMATION: Synthetic

<400> SEQUENCE: 357

Gly Phe Thr Phe Ser Ser Tyr Ala
1               5

<210> SEQ ID NO 358
<211> LENGTH: 24
<212> TYPE: DNA
<213> ORGANISM: Artificial Sequence
<220> FEATURE:
<223> OTHER INFORMATION: Synthetic

<400> SEQUENCE: 358
atatcatatg atggaagtaa taaa                                               24

<210> SEQ ID NO 359
<211> LENGTH: 8
<212> TYPE: PRT
<213> ORGANISM: Artificial Sequence
<220> FEATURE:
<223> OTHER INFORMATION: Synthetic

<400> SEQUENCE: 359

Ile Ser Tyr Asp Gly Ser Asn Lys
1               5

<210> SEQ ID NO 360
<211> LENGTH: 33
<212> TYPE: DNA
<213> ORGANISM: Artificial Sequence
<220> FEATURE:
<223> OTHER INFORMATION: Synthetic

<400> SEQUENCE: 360
gcgaaagaaa gttcttcgta cggtttggac gtc                                     33

<210> SEQ ID NO 361
<211> LENGTH: 11
<212> TYPE: PRT
<213> ORGANISM: Artificial Sequence
<220> FEATURE:
<223> OTHER INFORMATION: Synthetic

<400> SEQUENCE: 361

Ala Lys Glu Ser Ser Ser Tyr Gly Leu Asp Val
1               5                   10

<210> SEQ ID NO 362
<211> LENGTH: 321
```

-continued

<212> TYPE: DNA
<213> ORGANISM: Artificial Sequence
<220> FEATURE:
<223> OTHER INFORMATION: Synthetic

<400> SEQUENCE: 362

```
gacatccaga tgacccagtc tccttccacc ctgtctgcat ctgtaggaga cagagtcgcc      60
atcacttgcc gggccagtca gagtattagt aactggttgg cctggtatca gcagaaacca     120
gggaaagccc ctaaactcct gatctctaag gcgtctagtt taaaaagtgg ggtcccatca     180
aggttcagcg gcagtggatc tgggacagaa ttcactctca ccatcagcag cctgcagcct     240
gatgattttg cagcttatta ctgccaacag tataatagtt attcgtacac ttttggccag     300
gggaccaagc tggagataaa a                                                321
```

<210> SEQ ID NO 363
<211> LENGTH: 107
<212> TYPE: PRT
<213> ORGANISM: Artificial Sequence
<220> FEATURE:
<223> OTHER INFORMATION: Synthetic

<400> SEQUENCE: 363

```
Asp Ile Gln Met Thr Gln Ser Pro Ser Thr Leu Ser Ala Ser Val Gly
 1               5                  10                  15

Asp Arg Val Ala Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Ser Lys Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ala Tyr Tyr Cys Gln Gln Tyr Asn Ser Tyr Ser Tyr
                85                  90                  95

Thr Phe Gly Gln Gly Thr Lys Leu Glu Ile Lys
            100                 105
```

<210> SEQ ID NO 364
<211> LENGTH: 18
<212> TYPE: DNA
<213> ORGANISM: Artificial Sequence
<220> FEATURE:
<223> OTHER INFORMATION: Synthetic

<400> SEQUENCE: 364

```
cagagtatta gtaactgg                                                     18
```

<210> SEQ ID NO 365
<211> LENGTH: 6
<212> TYPE: PRT
<213> ORGANISM: Artificial Sequence
<220> FEATURE:
<223> OTHER INFORMATION: Synthetic

<400> SEQUENCE: 365

```
Gln Ser Ile Ser Asn Trp
 1               5
```

<210> SEQ ID NO 366
<211> LENGTH: 9
<212> TYPE: DNA

<210> SEQ ID NO 366
<211> LENGTH: 9
<212> TYPE: DNA
<213> ORGANISM: Artificial Sequence
<220> FEATURE:
<223> OTHER INFORMATION: Synthetic

<400> SEQUENCE: 366 aaggcgtct                                                                 9

<210> SEQ ID NO 367
<211> LENGTH: 3
<212> TYPE: PRT
<213> ORGANISM: Artificial Sequence
<220> FEATURE:
<223> OTHER INFORMATION: Synthetic

<400> SEQUENCE: 367

Lys Ala Ser
 1

<210> SEQ ID NO 368
<211> LENGTH: 27
<212> TYPE: DNA
<213> ORGANISM: Artificial Sequence
<220> FEATURE:
<223> OTHER INFORMATION: Synthetic

<400> SEQUENCE: 368
caacagtata atagttattc gtacact                                            27

<210> SEQ ID NO 369
<211> LENGTH: 9
<212> TYPE: PRT
<213> ORGANISM: Artificial Sequence
<220> FEATURE:
<223> OTHER INFORMATION: Synthetic

<400> SEQUENCE: 369

Gln Gln Tyr Asn Ser Tyr Ser Tyr Thr
 1               5

<210> SEQ ID NO 370
<211> LENGTH: 357
<212> TYPE: DNA
<213> ORGANISM: Artificial Sequence
<220> FEATURE:
<223> OTHER INFORMATION: Synthetic

<400> SEQUENCE: 370
caggtccaac tggtggagtc tgggggaggc gtggtccagc ctggggggtc cctgagactc        60
tcctgtgcag cctctggatt caccttcagt agctatggca tgcactgggt ccgccaggct       120
ccaggcaggg gactggagtg ggtggcagtt ttatcatatg atggcagtaa agaattctac       180
gcagactccg tgaaggtccg attcaccgtc tccagagaca actccaagaa cacgctttat       240
ctgcaaatga gcagcctgag agttgaggac acggctatat atttctgtgc gaaagaagga       300
agaactggga attggttcga cccctggggc cagggaaccc tggtcgccgt ctcctca          357

<210> SEQ ID NO 371
<211> LENGTH: 119
<212> TYPE: PRT
<213> ORGANISM: Artificial Sequence
<220> FEATURE:
<223> OTHER INFORMATION: Synthetic

<400> SEQUENCE: 371

Gln Val Gln Leu Val Glu Ser Gly Gly Gly Val Val Gln Pro Gly Gly

-continued

```
                1               5                  10                  15
Ser Leu Arg Leu Ser Cys Ala Ala Ser Gly Phe Thr Phe Ser Ser Tyr
                20                  25                  30

Gly Met His Trp Val Arg Gln Ala Pro Gly Arg Gly Leu Glu Trp Val
            35                  40                  45

Ala Val Leu Ser Tyr Asp Gly Ser Lys Glu Phe Tyr Ala Asp Ser Val
        50                  55                  60

Lys Val Arg Phe Thr Val Ser Arg Asp Asn Ser Lys Asn Thr Leu Tyr
65                  70                  75                  80

Leu Gln Met Ser Ser Leu Arg Val Glu Asp Thr Ala Ile Tyr Phe Cys
                85                  90                  95

Ala Lys Glu Gly Arg Thr Gly Asn Trp Phe Asp Pro Trp Gly Gln Gly
            100                 105                 110

Thr Leu Val Ala Val Ser Ser
        115
```

<210> SEQ ID NO 372
<211> LENGTH: 24
<212> TYPE: DNA
<213> ORGANISM: Artificial Sequence
<220> FEATURE:
<223> OTHER INFORMATION: Synthetic

<400> SEQUENCE: 372
ggattcacct tcagtagcta tggc         24

<210> SEQ ID NO 373
<211> LENGTH: 8
<212> TYPE: PRT
<213> ORGANISM: Artificial Sequence
<220> FEATURE:
<223> OTHER INFORMATION: Synthetic

<400> SEQUENCE: 373

```
Gly Phe Thr Phe Ser Ser Tyr Gly
1               5
```

<210> SEQ ID NO 374
<211> LENGTH: 24
<212> TYPE: DNA
<213> ORGANISM: Artificial Sequence
<220> FEATURE:
<223> OTHER INFORMATION: Synthetic

<400> SEQUENCE: 374
ttatcatatg atggcagtaa agaa         24

<210> SEQ ID NO 375
<211> LENGTH: 8
<212> TYPE: PRT
<213> ORGANISM: Artificial Sequence
<220> FEATURE:
<223> OTHER INFORMATION: Synthetic

<400> SEQUENCE: 375

```
Leu Ser Tyr Asp Gly Ser Lys Glu
1               5
```

<210> SEQ ID NO 376
<211> LENGTH: 36
<212> TYPE: DNA
<213> ORGANISM: Artificial Sequence
<220> FEATURE:

<223> OTHER INFORMATION: Synthetic

<400> SEQUENCE: 376
gcgaaagaag gaagaactgg gaattggttc gacccc    36

<210> SEQ ID NO 377
<211> LENGTH: 12
<212> TYPE: PRT
<213> ORGANISM: Artificial Sequence
<220> FEATURE:
<223> OTHER INFORMATION: Synthetic

<400> SEQUENCE: 377

Ala Lys Glu Gly Arg Thr Gly Asn Trp Phe Asp Pro
 1               5                  10

<210> SEQ ID NO 378
<211> LENGTH: 321
<212> TYPE: DNA
<213> ORGANISM: Artificial Sequence
<220> FEATURE:
<223> OTHER INFORMATION: Synthetic

<400> SEQUENCE: 378
gacatccaga tgacccagtc tccatcctca ctgtctgcat ctgtaggaga cagagtcacc    60
atcacttgtc gggcgagtca ggccattaac aattttttag cctggtttca gcagaaacca   120
ggtaaaaccc ctaagtccct gatctttgct acatccagtt tacaaagtgg ggtcccatca   180
aggttcagcg gcagtgaatc tgggacagac ttcactctca ccatcagcag cctgcagcct   240
gaagattttg caacttatta ctgccaacag tataatagtc accgtggac gttcggccaa    300 gggaccaagg tggaaatcaa a                                              321

<210> SEQ ID NO 379
<211> LENGTH: 107
<212> TYPE: PRT
<213> ORGANISM: Artificial Sequence
<220> FEATURE:
<223> OTHER INFORMATION: Synthetic

<400> SEQUENCE: 379

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Asn Asn Phe
            20                  25                  30

Leu Ala Trp Phe Gln Gln Lys Pro Gly Lys Thr Pro Lys Ser Leu Ile
        35                  40                  45

Phe Ala Thr Ser Ser Leu Gln Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys
            100                 105

<210> SEQ ID NO 380
<211> LENGTH: 18
<212> TYPE: DNA
<213> ORGANISM: Artificial Sequence
<220> FEATURE:
<223> OTHER INFORMATION: Synthetic

<400> SEQUENCE: 380
caggccatta acaatttt                                                         18

<210> SEQ ID NO 381
<211> LENGTH: 6
<212> TYPE: PRT
<213> ORGANISM: Artificial Sequence
<220> FEATURE:
<223> OTHER INFORMATION: Synthetic

<400> SEQUENCE: 381

Gln Ala Ile Asn Asn Phe
 1               5

<210> SEQ ID NO 382
<211> LENGTH: 9
<212> TYPE: DNA
<213> ORGANISM: Artificial Sequence
<220> FEATURE:
<223> OTHER INFORMATION: Synthetic

<400> SEQUENCE: 382 gctacatcc                                                                    9

<210> SEQ ID NO 383
<211> LENGTH: 3
<212> TYPE: PRT
<213> ORGANISM: Artificial Sequence
<220> FEATURE:
<223> OTHER INFORMATION: Synthetic

<400> SEQUENCE: 383

Ala Thr Ser
 1

<210> SEQ ID NO 384
<211> LENGTH: 27
<212> TYPE: DNA
<213> ORGANISM: Artificial Sequence
<220> FEATURE:
<223> OTHER INFORMATION: Synthetic

<400> SEQUENCE: 384
caacagtata atagtcaccc gtggacg                                               27

<210> SEQ ID NO 385
<211> LENGTH: 9
<212> TYPE: PRT
<213> ORGANISM: Artificial Sequence
<220> FEATURE:
<223> OTHER INFORMATION: Synthetic

<400> SEQUENCE: 385

Gln Gln Tyr Asn Ser His Pro Trp Thr
 1               5

<210> SEQ ID NO 386
<211> LENGTH: 352
<212> TYPE: DNA
<213> ORGANISM: Artificial Sequence
<220> FEATURE:
<223> OTHER INFORMATION: Synthetic

<400> SEQUENCE: 386
caggttcagc tggtgcagtc tggagctgag gtgaagaagc ctggggcctc agtgaaggtc           60

```
tcctgcaagg cttctggtta cacctttacc aactatggta tcagctgggt gcgacaggcc    120
cctggacaag ggcttgagtg gatgggatgg atcagcgttt acaatggtaa acaaactat    180 gcacagaagc tccagggcag agtcaccatg accacagaca catccacgag cacagcctac    240
atggagctga ggagcctgag atctgacgac acggccgtgt attactgtgc gagaggtagt    300
ggctacgatt tggactactg gggccaagga accctggtca ccgtctcctc ag          352
```

<210> SEQ ID NO 387
<211> LENGTH: 117
<212> TYPE: PRT
<213> ORGANISM: Artificial Sequence
<220> FEATURE:
<223> OTHER INFORMATION: Synthetic

<400> SEQUENCE: 387

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Gly Tyr Asp Leu Asp Tyr Trp Gly Gln Gly Thr Leu
            100                 105                 110

Val Thr Val Ser Ser
        115
```

<210> SEQ ID NO 388
<211> LENGTH: 322
<212> TYPE: DNA
<213> ORGANISM: Artificial Sequence
<220> FEATURE:
<223> OTHER INFORMATION: Synthetic

<400> SEQUENCE: 388

```
gccatccaga tgacccagtc tccatcctcc ctgtctgcat ctgtaggaga cagagtcacc     60
atcacttgcc gggcaagtca gggcattaga aatgctttag gctggtatca gcagaaacca    120
gggaaagccc ctaagctcct gatctatgct gcatccagtt tacaaagtgg ggtcccatca    180
aggttcagcg gcagtggatc tggcacagat ttcactctca ccatcagcag cctgcagcct    240
gaagattttg caactattta ctgtctacaa gatttcaatt acccgtacac ttttggccag    300
gggaccaagc tggagatcaa ac                                              322
```

<210> SEQ ID NO 389
<211> LENGTH: 107
<212> TYPE: PRT
<213> ORGANISM: Artificial Sequence
<220> FEATURE:
<223> OTHER INFORMATION: Synthetic

<400> SEQUENCE: 389

```
Ala Ile Gln Met Thr Gln Ser Pro Ser Ser Leu Ser Ala Ser Val Gly
 1               5                  10                  15
```

Asp Arg Val Thr Ile Thr Cys Arg Ala Ser Gln Gly Ile Arg Asn Ala
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Tyr
                85                  90                  95

Thr Phe Gly Gln Gly Thr Lys Leu Glu Ile Lys
            100                 105

<210> SEQ ID NO 390
<211> LENGTH: 352
<212> TYPE: DNA
<213> ORGANISM: Artificial Sequence
<220> FEATURE:
<223> OTHER INFORMATION: Synthetic

<400> SEQUENCE: 390
caggttcagc tggtgcagtc tggagctgag gtgaagaagc ctggggcctc agtgaaggtc      60
tcctgcaagg cttctggtta cacctttacc aactatggta tcagctgggt gcgacaggcc     120
cctggacaag gcttgagtg gatgggatgg atcagcgttt acaatggtaa aacaaactat     180
gcacagaagc tccagggcag agtcaccatg accacagaca catccacgac acagcctac     240 atggaaatga ggagcctgag atctgacgac acggccgttt attactgtgc gagaggtagt     300
ggctacgatt tggactactg gggccaggga accctggtca ccgtctcctc ag             352

<210> SEQ ID NO 391
<211> LENGTH: 117
<212> TYPE: PRT
<213> ORGANISM: Artificial Sequence
<220> FEATURE:
<223> OTHER INFORMATION: Synthetic

<400> SEQUENCE: 391

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Lys Thr Asn Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Met Arg Ser Leu Arg Ser Asp Asp Thr Ala Val Tyr Tyr Cys
                85                  90                  95

Ala Arg Gly Ser Gly Tyr Asp Leu Asp Tyr Trp Gly Gln Gly Thr Leu
            100                 105                 110

Val Thr Val Ser Ser
        115

<210> SEQ ID NO 392
<211> LENGTH: 322
<212> TYPE: DNA

<213> ORGANISM: Artificial Sequence
<220> FEATURE:
<223> OTHER INFORMATION: Synthetic

<400> SEQUENCE: 392

```
gccatccaga tgacccagtc tccatcctcc ctgtctgcat ctgtaggaga cagagtcacc      60
atcacttgcc gggcaagtca gggcattaga aatgctttag ctggtatca gcagaaacca     120
gggaaagccc ctaagctcct gatctatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gatttcaatt acccgtacac ttttggccag    300
gggaccaagc tggagatcaa ac                                             322
```

<210> SEQ ID NO 393
<211> LENGTH: 107
<212> TYPE: PRT
<213> ORGANISM: Artificial Sequence
<220> FEATURE:
<223> OTHER INFORMATION: Synthetic

<400> SEQUENCE: 393

```
Ala Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Ala
            20                  25                  30
Leu Gly Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Phe Asn Tyr Pro Tyr
                85                  90                  95
Thr Phe Gly Gln Gly Thr Lys Leu Glu Ile Lys
            100                 105
```

<210> SEQ ID NO 394
<211> LENGTH: 385
<212> TYPE: DNA
<213> ORGANISM: Artificial Sequence
<220> FEATURE:
<223> OTHER INFORMATION: Synthetic

<400> SEQUENCE: 394

```
gaggtgcagc tggtggagtc tgggggaggc ttggtccagc ctggggggtc cctgagactc      60
tcctgtgcag cctctggatt cacctttagt tccttctgga tgagctgggt ccgccaggct    120
ccagggaagg ggctggagtg ggtggccaac ataaagcaag atggaagtga aaatactat    180
gtggactctg tgaagggccg attcaccatc tccagagaca acgccaagaa ctcactgtat    240
ctgcaaatga acagcctgag agccgaggac acggctgtgt attactgtgc gagagatccc    300
gggcgaacta tggttcgggg aggtataaga tattactatg gtatggacgt ctggggggcaa    360
gggaccacgg tcaccgtctc ctcag                                          385
```

<210> SEQ ID NO 395
<211> LENGTH: 128
<212> TYPE: PRT
<213> ORGANISM: Artificial Sequence
<220> FEATURE:

<223> OTHER INFORMATION: Synthetic

<400> SEQUENCE: 395

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Phe
            20                  25                  30
Trp Met Ser Trp Val Arg Gln Ala Pro Gly Lys Gly Leu Glu Trp Val
        35                  40                  45
Ala Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Pro Gly Arg Thr Met Val Arg Gly Gly Ile Arg Tyr Tyr
            100                 105                 110
Tyr Gly Met Asp Val Trp Gly Gln Gly Thr Thr Val Thr Val Ser Ser
        115                 120                 125
```

<210> SEQ ID NO 396
<211> LENGTH: 322
<212> TYPE: DNA
<213> ORGANISM: Artificial Sequence
<220> FEATURE:
<223> OTHER INFORMATION: Synthetic

<400> SEQUENCE: 396

```
gacatccaga tgacccagtc tccatcttcc gtgtctgcat ctgtaggaga cagagtcacc    60
atcacttgtc gggcgagtca gggtgttagt agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tccctctcac tttcggcgga   300
gggaccaagg tggagatcaa ac                                            322
```

<210> SEQ ID NO 397
<211> LENGTH: 107
<212> TYPE: PRT
<213> ORGANISM: Artificial Sequence
<220> FEATURE:
<223> OTHER INFORMATION: Synthetic

<400> SEQUENCE: 397

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Val Ser Ser Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Leu
                85                  90                  95
Thr Phe Gly Gly Gly Thr Lys Val Glu Ile Lys
            100                 105
```

<210> SEQ ID NO 398
<211> LENGTH: 385
<212> TYPE: DNA
<213> ORGANISM: Artificial Sequence
<220> FEATURE:
<223> OTHER INFORMATION: Synthetic

<400> SEQUENCE: 398

```
gaggtgcagc tggtggagtc tgggggaggc ttggtccagc ctgggggqtc cctgagactc      60
tcctgtgcag cctctggatt cacctttagt tccttctgga tgagctgggt ccgccaggct     120
ccagggaagg ggctggagtg ggtggccaac ataaagcaag atggaagtga aaatactat      180
gtggactctg tgaagggccg attcaccatc tccagagaca acgccaagaa ctcactgtat     240
ctgcaaatga acagcctgag agccgaggac acggctgtgt attactgtgc gagagatccc     300
gggcgaacta tggttcgggg aggtataaga tattactatg gtatggacgt ctgggggcaa     360
gggaccacgg tcaccgtctc ctcag                                           385
```

<210> SEQ ID NO 399
<211> LENGTH: 128
<212> TYPE: PRT
<213> ORGANISM: Artificial Sequence
<220> FEATURE:
<223> OTHER INFORMATION: Synthetic

<400> SEQUENCE: 399

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Arg Thr Met Val Arg Gly Gly Ile Arg Tyr Tyr
            100                 105                 110

Tyr Gly Met Asp Val Trp Gly Gln Gly Thr Thr Val Thr Val Ser Ser
        115                 120                 125
```

<210> SEQ ID NO 400
<211> LENGTH: 322
<212> TYPE: DNA
<213> ORGANISM: Artificial Sequence
<220> FEATURE:
<223> OTHER INFORMATION: Synthetic

<400> SEQUENCE: 400

```
gacatccaga tgacccagtc tccatcttcc gtgtctgcat ctgtaggaga cagagtcacc      60
atcacttgtc gggcgagtca gggtgttagt agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt tccctctcac tttcggcgga     300
```

-continued

```
gggaccaagg tggagatcaa ac                                          322
```

<210> SEQ ID NO 401
<211> LENGTH: 107
<212> TYPE: PRT
<213> ORGANISM: Artificial Sequence
<220> FEATURE:
<223> OTHER INFORMATION: Synthetic

<400> SEQUENCE: 401

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 402
<211> LENGTH: 367
<212> TYPE: DNA
<213> ORGANISM: Artificial Sequence
<220> FEATURE:
<223> OTHER INFORMATION: Synthetic

<400> SEQUENCE: 402

```
gaggtgcagc tggtggagtc tgggggaggc ttggtccagc ctggggggtc cctgagactc      60
tcctgtgcag cctctggatt cacctttagt agccattgga tgagctgggt ccgccaggct     120
ccagggaagg ggctggagtg ggtggccaac ataaagcaag atggaagtga taaatactat     180
gtggactctg tgaagggccg attcaccatc tccagagaca acgccaagaa ctcactgtat     240
ctgcaaatga acagcctgag agccgaggac acggctgtgt attactgtgc gagagatcgg     300
ggggttagac cacctcgtgg ggcttttgat atctggggcc aagggacaat ggtcaccgtc     360
tcttcag                                                              367
```

<210> SEQ ID NO 403
<211> LENGTH: 122
<212> TYPE: PRT
<213> ORGANISM: Artificial Sequence
<220> FEATURE:
<223> OTHER INFORMATION: Synthetic

<400> SEQUENCE: 403

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Asp Lys Tyr Tyr Val Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Val Arg Pro Arg Gly Ala Phe Asp Ile Trp
            100                 105                 110

Gly Gln Gly Thr Met Val Thr Val Ser Ser
            115                 120

<210> SEQ ID NO 404
<211> LENGTH: 322
<212> TYPE: DNA
<213> ORGANISM: Artificial Sequence
<220> FEATURE:
<223> OTHER INFORMATION: Synthetic

<400> SEQUENCE: 404
gacatccaga tgacccagtc tccatcttcc gtgtctgcat ctgtaggaga cagagtcacc      60
atcacttgtc gggcgagtca gggtatcagc agctggttag cctggtatca gcagaaacca     120
gggaaagccc ctaagctcct gatctatgct gcatccagtt tgcaaagtgg ggtcccatca     180
aggttcagcg gcagtggatc tgggacagat tcactctcac catcagcag cctgcagcct     240 gaagattttg caacttacta ttgtcaacag gctaacagtt ccctctcac tttcggcgga     300 gggaccaagg tggagatcaa ac                                              322

<210> SEQ ID NO 405
<211> LENGTH: 107
<212> TYPE: PRT
<213> ORGANISM: Artificial Sequence
<220> FEATURE:
<223> OTHER INFORMATION: Synthetic

<400> SEQUENCE: 405

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105

<210> SEQ ID NO 406
<211> LENGTH: 367
<212> TYPE: DNA
<213> ORGANISM: Artificial Sequence
<220> FEATURE:
<223> OTHER INFORMATION: Synthetic

<400> SEQUENCE: 406
gaggtgcagc tggtggagtc tgggggaggc ttggtccagc cggggggtc cctgagactc       60 tcctgtgcag cctctggatt cacctttagt agccattgga tgaactgggt ccgccaggct     120
```

```
ccagggaagg ggctggagtg ggtggccaac ataaagcaag atggaagtga taaatactat    180
gtggactctg tgaagggccg attcaccatc tccagagaca acgccaagaa ctcactctat    240
ctgcaattga acagcctgat agccgaggac acggctgtgt attactgtgc gagagatcgg    300
ggggttagac cacctcgtgg ggcttttgat atctggggcc aagggacaat ggtcaccgtc    360
tcttcag                                                              367
```

```
<210> SEQ ID NO 407
<211> LENGTH: 122
<212> TYPE: PRT
<213> ORGANISM: Artificial Sequence
<220> FEATURE:
<223> OTHER INFORMATION: Synthetic

<400> SEQUENCE: 407
```

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser His
         20                  25                  30

Trp Met Asn Trp Val Arg Gln Ala Pro Gly Lys Gly Leu Glu Trp Val
     35                  40                  45

Ala Asn Ile Lys Gln Asp Gly Ser Asp Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Leu Asn Ser Leu Ile Ala Glu Asp Thr Ala Val Tyr Tyr Cys
                 85                  90                  95

Ala Arg Asp Arg Gly Val Arg Pro Pro Arg Gly Ala Phe Asp Ile Trp
             100                 105                 110

Gly Gln Gly Thr Met Val Thr Val Ser Ser
         115                 120

```
<210> SEQ ID NO 408
<211> LENGTH: 322
<212> TYPE: DNA
<213> ORGANISM: Artificial Sequence
<220> FEATURE:
<223> OTHER INFORMATION: Synthetic

<400> SEQUENCE: 408
```

```
gacatccaga tgacccagtc tccatcttcc gtgtctgcat ctgtaggaga cagagtcacc     60
atcacttgtc gggcgagtca gggtatcagc agctggttag cctggtatca gcagaaacca    120
gggaaagccc ctaagctcct gatctatgct gcatccagtt ttcaaagtgg ggtcccatca    180
aggttcagcg gcagtggatc tgggacagat ttcactctca ccatcagcag cctgcagcct    240
gaagattttg caacttactt ttgtcaacag gctaacagtt ccctctcac tttcggcgga    300 gggaccaagg tggagatcaa ac                                             322
```

```
<210> SEQ ID NO 409
<211> LENGTH: 107
<212> TYPE: PRT
<213> ORGANISM: Artificial Sequence
<220> FEATURE:
<223> OTHER INFORMATION: Synthetic

<400> SEQUENCE: 409
```

Asp Ile Gln Met Thr Gln Ser Pro Ser Ser Val Ser Ala Ser Val Gly
 1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Phe Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Leu
                85                  90                  95

Thr Phe Gly Gly Gly Thr Lys Val Glu Ile Lys
            100                 105

<210> SEQ ID NO 410
<211> LENGTH: 355
<212> TYPE: DNA
<213> ORGANISM: Artificial Sequence
<220> FEATURE:
<223> OTHER INFORMATION: Synthetic

<400> SEQUENCE: 410
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt cttagtcgga caagtgtcag tataggctat     180
gcggactctg tgaagggccg attcaccatc tccagagaca cgccaagaa ctccctgtat      240 ctgcaaatga acagtctgag agctgaggac acggccttgt attactgtgc aaaatggggg     300
acccgggggt attttgacta ctggggccaa ggaaccctgg tcaccgtctc ctcag          355

<210> SEQ ID NO 411
<211> LENGTH: 118
<212> TYPE: PRT
<213> ORGANISM: Artificial Sequence
<220> FEATURE:
<223> OTHER INFORMATION: Synthetic

<400> SEQUENCE: 411

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Leu Ser Arg Thr Ser Val Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Trp Gly Thr Arg Gly Tyr Phe Asp Tyr Trp Gly Gln Gly Thr
            100                 105                 110

Leu Val Thr Val Ser Ser
        115

<210> SEQ ID NO 412
<211> LENGTH: 322
<212> TYPE: DNA

<213> ORGANISM: Artificial Sequence
<220> FEATURE:
<223> OTHER INFORMATION: Synthetic

<400> SEQUENCE: 412

```
gacatccaga tgacccagtc tccatcttcc gtgtctgcat ctgtaggaga cagagtcacc    60
atcacttgtc gggcgagtca ggatattagt atttggttag cctggtatca gcagaaacca   120
gggaaagccc ctaagctcct gatctatgtt gcatccagtt tgcaaagtgg ggtcccatca   180
aggttcagcg gcagtggatc tgggacagat tcactctcac catcagcag cctgcagcct    240
gaagattttg caacttacta ttgtcaacag gctaacagtt cccgatcac cttcggccaa    300
gggacacgac tggagattaa ac                                            322
```

<210> SEQ ID NO 413
<211> LENGTH: 107
<212> TYPE: PRT
<213> ORGANISM: Artificial Sequence
<220> FEATURE:
<223> OTHER INFORMATION: Synthetic

<400> SEQUENCE: 413

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Ser Ile Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105
```

<210> SEQ ID NO 414
<211> LENGTH: 355
<212> TYPE: DNA
<213> ORGANISM: Artificial Sequence
<220> FEATURE:
<223> OTHER INFORMATION: Synthetic

<400> SEQUENCE: 414

```
gaagtgcagc tggtggagtc tgggggaggc ttggtacagc ctggcaggtc cctgagactc    60
tcctgtgagg cctctggatt cacctttgat gattatgcca tgcactgggt ccggcaagct   120
ccggggaagg gcctggaatg ggtctcaggt cttagtcgga caagtgtcag tataggctat   180
gcggactctg tgaagggccg attcaccatc tccagagaca acgccaagaa ctccctttat   240
ttggaaatga acagtctgag acctgaggac acggccttat attactgtgc aaaatggggg   300
acccggggggt attttgacta ccggggccag ggaaccctgg tcaccgtctc ctcag       355
```

<210> SEQ ID NO 415
<211> LENGTH: 118
<212> TYPE: PRT
<213> ORGANISM: Artificial Sequence
<220> FEATURE:
<223> OTHER INFORMATION: Synthetic

<400> SEQUENCE: 415

Glu Val Gln Leu Val Glu Ser Gly Gly Gly Leu Val Gln Pro Gly Arg
1               5                   10                  15

Ser Leu Arg Leu Ser Cys Glu Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Leu Ser Arg Thr Ser Val Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Pro Glu Asp Thr Ala Leu Tyr Tyr Cys
                85                  90                  95

Ala Lys Trp Gly Thr Arg Gly Tyr Phe Asp Tyr Arg Gly Gln Gly Thr
            100                 105                 110

Leu Val Thr Val Ser Ser
        115

<210> SEQ ID NO 416
<211> LENGTH: 322
<212> TYPE: DNA
<213> ORGANISM: Artificial Sequence
<220> FEATURE:
<223> OTHER INFORMATION: Synthetic

<400> SEQUENCE: 416
gacatccaga tgacccagtc tccatcttcc gtgtctgcat ctgtgggaga cagagtcacc      60
atcacttgtc gggcgagtca ggatattagt atttggttag cctggtatca gcagagtcca     120
gggaaagccc ctaaactcct gatcaatgtt gcatcccgtt tgcaaagtgg ggtcccatca     180
aggttcagcg gcagtggatc tgggacagat ttcactctca ccatcaacag tctgcagcct     240
gaagattttg taacttacta ttgtcaacag gctaacagtt tcccgatcac cttcggccaa     300
gggacacgac tggagattaa ac                                              322

<210> SEQ ID NO 417
<211> LENGTH: 107
<212> TYPE: PRT
<213> ORGANISM: Artificial Sequence
<220> FEATURE:
<223> OTHER INFORMATION: Synthetic

<400> SEQUENCE: 417

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ile Trp
            20                  25                  30

Leu Ala Trp Tyr Gln Gln Ser Pro Gly Lys Ala Pro Lys Leu Leu Ile
        35                  40                  45

Asn Val Ala Ser Arg Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Val Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 418
<211> LENGTH: 352
<212> TYPE: DNA
<213> ORGANISM: Artificial Sequence
<220> FEATURE:
<223> OTHER INFORMATION: Synthetic

<400> SEQUENCE: 418

```
caggtgcagc tggtggagtc tgggggaggc ttggtcaagc ctggagggtc cctgagactc      60
tcctgtgcag cctctggatt cacaatcagt gaccactaca tgagctggat ccgccaggct     120
ccagggaagg gctggagtg gtttcatac attagtagta gtggtagtaa aatatactac       180
gcagactctg tgaagggccg attcaccatc tccagggaca acgccaagaa ctcactgtat     240
ctgcaaatga acagcctgag agccgaggac acggccgtgt attactgtgc gagaacacga    300
cagctcgtgg gggactactg gggccaagga accctggtca ccgtctcctc ag             352
```

<210> SEQ ID NO 419
<211> LENGTH: 117
<212> TYPE: PRT
<213> ORGANISM: Artificial Sequence
<220> FEATURE:
<223> OTHER INFORMATION: Synthetic

<400> SEQUENCE: 419

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Ile Ser Asp His
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Lys Ile Tyr Tyr Ala Asp Ser Val
    50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Tyr Cys
                85                  90                  95

Ala Arg Thr Arg Gln Leu Val Gly Asp Tyr Trp Gly Gln Gly Thr Leu
            100                 105                 110

Val Thr Val Ser Ser
        115
```

<210> SEQ ID NO 420
<211> LENGTH: 322
<212> TYPE: DNA
<213> ORGANISM: Artificial Sequence
<220> FEATURE:
<223> OTHER INFORMATION: Synthetic

<400> SEQUENCE: 420

```
gacatccagt tgacccagtc tccatccttc ctgtctgcat ctgtaggaga cagagtcacc      60
atcacttgcc gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt acccgctcac tttcggcgga    300
gggaccaagg tggagatcaa ac                                              322
```

<210> SEQ ID NO 421
<211> LENGTH: 107
<212> TYPE: PRT
<213> ORGANISM: Artificial Sequence
<220> FEATURE:
<223> OTHER INFORMATION: Synthetic

<400> SEQUENCE: 421

```
Asp Ile Gln Leu Thr Gln Ser Pro Ser Phe Leu Ser Ala Ser Val Gly
  1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys
            100                 105
```

<210> SEQ ID NO 422
<211> LENGTH: 352
<212> TYPE: DNA
<213> ORGANISM: Artificial Sequence
<220> FEATURE:
<223> OTHER INFORMATION: Synthetic

<400> SEQUENCE: 422

```
caggtgcagc tggtggagtc tgggggaggc ttggtcaagc ctggagggtc cctgagactc     60
tcctgtgcag cctctggatt cacaatcagt gaccactaca tgagctggat ccgccaggct    120
ccagggaagg ggctggagtg ggtttcatac attagtagta gtggtagtaa atatactac    180
gcagactctg tgaagggccg attcaccatc tccagggaca cgccaagaa ctcactgtat    240
ctgcaaatga acagcctgag agccgaggac acggccgtgt attactgtgc gagaacacga    300
cagctcgtgg gggactactg gggccaagga accctggtca ccgtctcctc ag           352
```

<210> SEQ ID NO 423
<211> LENGTH: 117
<212> TYPE: PRT
<213> ORGANISM: Artificial Sequence
<220> FEATURE:
<223> OTHER INFORMATION: Synthetic

<400> SEQUENCE: 423

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Ile Ser Asp His
                 20                  25                  30

Tyr Met Ser Trp Ile Arg Gln Ala Pro Gly Lys Gly Leu Glu Trp Val
             35                  40                  45

Ser Tyr Ile Ser Ser Ser Gly Ser Lys Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ala Arg Thr Arg Gln Leu Val Gly Asp Tyr Trp Gly Gln Gly Thr Leu
                100                 105                 110
Val Thr Val Ser Ser
        115

<210> SEQ ID NO 424
<211> LENGTH: 322
<212> TYPE: DNA
<213> ORGANISM: Artificial Sequence
<220> FEATURE:
<223> OTHER INFORMATION: Synthetic

<400> SEQUENCE: 424
gacatccagt tgacccagtc tccatccttc ctgtctgcat ctgtaggaga cagagtcacc    60
atcacttgct gggccagtca gggcattagc agttatttag cctggtatca gcaaaaacca   120
gggaaagccc ctaagctcct gatctttgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatagtt acccgctcac tttcggcgga   300
gggaccaagg tggagatcaa ac                                            322

<210> SEQ ID NO 425
<211> LENGTH: 107
<212> TYPE: PRT
<213> ORGANISM: Artificial Sequence
<220> FEATURE:
<223> OTHER INFORMATION: Synthetic

<400> SEQUENCE: 425

Asp Ile Gln Leu Thr Gln Ser Pro Ser Phe Leu Ser Ala Ser Val Gly
  1               5                  10                  15

Asp Arg Val Thr Ile Thr Cys Trp Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Phe Ala Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys
                100                 105

<210> SEQ ID NO 426
<211> LENGTH: 373
<212> TYPE: DNA
<213> ORGANISM: Artificial Sequence
<220> FEATURE:
<223> OTHER INFORMATION: Synthetic

<400> SEQUENCE: 426
gaagtgcagc tggtggagtc tgggggaggc ttggtacagc ctggcaggtc cctgagactc    60
tcctgtgcag cctctggatt cacctttgat aattatgcca tgcactgggt ccggcaagct   120
ccagggaagg gcctggagtg ggtctcaggt attaggtgga atagtggtag catagqctat   180 gcggactctg tgaagggccg attcaccatc tccagagaca cgccaagaa ctccctgtat    240 ctgcaaatga acagtctgag agctgaggac acggccttgt attactgtgc aaaagaaggt   300
```

-continued

```
ggatatagtg ctaccgccc cggacccttc tttgactact ggggccaagg aaccctggtc    360
accgtctcct cag                                                       373
```

```
<210> SEQ ID NO 427
<211> LENGTH: 124
<212> TYPE: PRT
<213> ORGANISM: Artificial Sequence
<220> FEATURE:
<223> OTHER INFORMATION: Synthetic

<400> SEQUENCE: 427
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
        35                  40                  45

Ser Gly Ile Arg Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Gly Tyr Ser Gly Tyr Arg Pro Gly Pro Phe Phe Asp
            100                 105                 110

Tyr Trp Gly Gln Gly Thr Leu Val Thr Val Ser Ser
        115                 120

```
<210> SEQ ID NO 428
<211> LENGTH: 322
<212> TYPE: DNA
<213> ORGANISM: Artificial Sequence
<220> FEATURE:
<223> OTHER INFORMATION: Synthetic

<400> SEQUENCE: 428
```

```
gaaatagtga tgacgcagtc tccagccacc ctgtctgtgt ctccagggga agagccacc    60 ctctcctgca gggccagtca gagtgttaac tacaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggccgctcac tttcggcgga   300
gggaccaagg tggagatcaa ac                                            322
```

```
<210> SEQ ID NO 429
<211> LENGTH: 107
<212> TYPE: PRT
<213> ORGANISM: Artificial Sequence
<220> FEATURE:
<223> OTHER INFORMATION: Synthetic

<400> SEQUENCE: 429
```

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Tyr Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 430
<211> LENGTH: 373
<212> TYPE: DNA
<213> ORGANISM: Artificial Sequence
<220> FEATURE:
<223> OTHER INFORMATION: Synthetic

<400> SEQUENCE: 430
gaagtgcagc tggtggagtc tgggggaggc ttggtacagc ctggcaggtc cctgagactc      60
tcctgtgcag cctctggatt cacctttgat aattatgcca tgcactgggt ccggcaagct     120
ccagggaagg gcctggagtg gtctcaggt attaggtgga atagtggtag cataggctat      180
gcggactctg tgaagggccg attcaccatc tccagagaca acgccaagaa ctccctgtat     240
ctgcaaatga atagtctgag agctgaggac acggccttgt attactgtgc aaaagaaggt    300
ggatatagtg gctaccgccc cggacccttc tttgactact ggggccaggg aaccctggtc     360
accgtctcct cag                                                        373

<210> SEQ ID NO 431
<211> LENGTH: 124
<212> TYPE: PRT
<213> ORGANISM: Artificial Sequence
<220> FEATURE:
<223> OTHER INFORMATION: Synthetic

<400> SEQUENCE: 431

Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
        35                  40                  45

Ser Gly Ile Arg Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Gly Tyr Ser Gly Tyr Arg Pro Gly Pro Phe Phe Asp
            100                 105                 110

Tyr Trp Gly Gln Gly Thr Leu Val Thr Val Ser Ser
        115                 120

<210> SEQ ID NO 432
<211> LENGTH: 322
<212> TYPE: DNA
<213> ORGANISM: Artificial Sequence
<220> FEATURE:
<223> OTHER INFORMATION: Synthetic -continued

<400> SEQUENCE: 432

```
gaaatagtga tgacgcagtc tccagccacc ctgtctgtgt ctccagggga aagagccacc      60
ctctcctgca gggccagtca gagtgttaac tacaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggccgctcac tttcggcgga     300
gggaccaagg tggagatcaa ac                                              322
```

<210> SEQ ID NO 433
<211> LENGTH: 107
<212> TYPE: PRT
<213> ORGANISM: Artificial Sequence
<220> FEATURE:
<223> OTHER INFORMATION: Synthetic

<400> SEQUENCE: 433

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Asn Tyr Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
            100                 105
```

<210> SEQ ID NO 434
<211> LENGTH: 352
<212> TYPE: DNA
<213> ORGANISM: Artificial Sequence
<220> FEATURE:
<223> OTHER INFORMATION: Synthetic

<400> SEQUENCE: 434

```
caggttcagc tggtgcagtc tggagctgag gtgaagaagc ctggggcctc agtgaaggtc      60
tcctgcaagg cttctggtta cacctttacc aactatggta tcagctgggt gcgacaggcc     120
cctggacaag gcttgagtg gatgggatgg atcagcgttt acaatggtca cacaaactat     180
gcacagaagc tccagggcag agtcaccatg accacagaca catccacgag cacagcctac     240
atggagctga ggagcctgag atctgacgac acggccgtgt attactgtgc gagagggagt     300
ggctacgatt ttgactcctg ggccaagga accctggtca ccgtctcctc ag              352
```

<210> SEQ ID NO 435
<211> LENGTH: 117
<212> TYPE: PRT
<213> ORGANISM: Artificial Sequence
<220> FEATURE:
<223> OTHER INFORMATION: Synthetic

<400> SEQUENCE: 435

```
Gln Val Gln Leu Val Gln Ser Gly Ala Glu Val Lys Lys Pro Gly Ala
  1               5                  10                  15
```

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Gly Tyr Asp Phe Asp Ser Trp Gly Gln Gly Thr Leu
            100                 105                 110

Val Thr Val Ser Ser
        115

<210> SEQ ID NO 436
<211> LENGTH: 322
<212> TYPE: DNA
<213> ORGANISM: Artificial Sequence
<220> FEATURE:
<223> OTHER INFORMATION: Synthetic

<400> SEQUENCE: 436
gccatccaga tgacccagtc tccatcctcc ctgtctgcat ctgtaggaga cagagtcacc      60
atcacttgcc gggcaagtca ggccattaga aatgctttag ctggtatca gcagaaacca     120 gggaaagccc ctaagctcct gatctatgct gcatccagtt tacaaagtgg ggtcccatca     180
aggttcagcg gcagtggatc tggcacagat ttcactctca ccatcagcag cctgcagcct     240
gaagattttg caacttatta ctgtctacaa gattacgatt acccgtacac ttttggccag     300
gggaccaagc tggagatcaa ac                                              322

<210> SEQ ID NO 437
<211> LENGTH: 107
<212> TYPE: PRT
<213> ORGANISM: Artificial Sequence
<220> FEATURE:
<223> OTHER INFORMATION: Synthetic

<400> SEQUENCE: 437

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Ala
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asp Tyr Pro Tyr
                85                  90                  95

Thr Phe Gly Gln Gly Thr Lys Leu Glu Ile Lys
            100                 105

<210> SEQ ID NO 438
<211> LENGTH: 352
<212> TYPE: DNA

<213> ORGANISM: Artificial Sequence
<220> FEATURE:
<223> OTHER INFORMATION: Synthetic

<400> SEQUENCE: 438

```
caggttcagc tggtgcagtc tggagctgag gtgaagaagc ctggggcctc agtgaaggtc      60
tcctgcaagg cttctggtta ccctttacc aactatggta tcagctgggt gcgacaggcc     120
cctggacaag ggcttgagtg gatgggatgg atcagcgttt acaatggtca cacaaactat     180
gcacagaagc tccagggcag agtcaccatg accacagaca catccacgag cacagcctac     240
atggagctga ggagcctgag atctgacgac acggccgtgt attactgtgc gagagggagt     300
ggctacgatt ttgactcctg gggccaagga accctggtca ccgtctcctc ag             352
```

<210> SEQ ID NO 439
<211> LENGTH: 117
<212> TYPE: PRT
<213> ORGANISM: Artificial Sequence
<220> FEATURE:
<223> OTHER INFORMATION: Synthetic

<400> SEQUENCE: 439

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asn Tyr
            20                  25                  30
Gly Ile Ser Trp Val Arg Gln Ala Pro Gly Gln Gly Leu Glu Trp Met
        35                  40                  45
Gly Trp Ile Ser Val Tyr Asn Gly His Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Gly Ser Gly Tyr Asp Phe Asp Ser Trp Gly Gln Gly Thr Leu
            100                 105                 110
Val Thr Val Ser Ser
        115
```

<210> SEQ ID NO 440
<211> LENGTH: 322
<212> TYPE: DNA
<213> ORGANISM: Artificial Sequence
<220> FEATURE:
<223> OTHER INFORMATION: Synthetic

<400> SEQUENCE: 440

```
gccatccaga tgacccagtc tccatcctcc ctgtctgcat ctgtaggaga cagagtcacc      60
atcacttgcc gggcaagtca ggccattaga aatgctttag ctggtatca gcagaaacca     120
gggaaagccc ctaagctcct gatctatgct gcatccagtt tacaaagtgg ggtcccatca     180
aggttcagcg gcagtggatc tggcacagat ttcactctca ccatcagcag cctgcagcct     240
gaagattttg caacttatta ctgtctacaa gattacgatt acccgtacac ttttggccag     300
gggaccaagc tggagatcaa ac                                              322
```

<210> SEQ ID NO 441
<211> LENGTH: 107
<212> TYPE: PRT
<213> ORGANISM: Artificial Sequence
<220> FEATURE:
<223> OTHER INFORMATION: Synthetic

<400> SEQUENCE: 441

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Ala
            20                  25                  30

Leu Gly Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asp Tyr Pro Tyr
                85                  90                  95

Thr Phe Gly Gln Gly Thr Lys Leu Glu Ile Lys
            100                 105

<210> SEQ ID NO 442
<211> LENGTH: 349
<212> TYPE: DNA
<213> ORGANISM: Artificial Sequence
<220> FEATURE:
<223> OTHER INFORMATION: Synthetic

<400> SEQUENCE: 442
caggtgcagc tggtgcagtc tggggctgag gtgaagaagc ctggggcctc agtgaaggtc      60
tcctgcaagg cttctagata caccttcacc agttatgata tcaactgggt gcgacaggcc     120
actggacaag ggcttgagtg gatgggatgg atgaacccaa acagtggtaa cacaggctat     180
gcacagaagt tccagggcag agtcaccatg accaggaaca cctccataag cacagcctac     240
atggagctga gcagcctgag atctgaggac acggccgtgt attactgtgc gagagtacga     300 cgctttttg actactgggg ccaaggaacc ctggtcaccg tctcctcag                  349

<210> SEQ ID NO 443
<211> LENGTH: 116
<212> TYPE: PRT
<213> ORGANISM: Artificial Sequence
<220> FEATURE:
<223> OTHER INFORMATION: Synthetic

<400> SEQUENCE: 443

Gln Val Gln Leu Val Gln Ser Gly Ala Glu Val Lys Lys Pro Gly Ala
1               5                   10                  15

Ser Val Lys Val Ser Cys Lys Ala Ser Arg Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Arg Phe Phe Asp Tyr Trp Gly Gln Gly Thr Leu Val
            100                 105                 110

```
<210> SEQ ID NO 444
<211> LENGTH: 322
<212> TYPE: DNA
<213> ORGANISM: Artificial Sequence
<220> FEATURE:
<223> OTHER INFORMATION: Synthetic

<400> SEQUENCE: 444
gacatccagt tgacccagtc tccatccttc ctgtctgcat ctgtaggaga cagagtcacc      60
atcacttgcc gggccagtca gggcattatc agttatttag cctggtatca gcaaaaacca     120
gggaaagccc ctaagctcct gatctatgct gcatccactt tgcaaagtgg ggtcccatca     180
aggttcagcg gcagtggatc tgggacagaa ttcactctca caatcagcag cctgcagcct     240
gaagattttg caacttatta ctgtcaccag cttaaaagtt acccgatcac cttcggccaa     300
gggacacgac tggagattaa ac                                              322

<210> SEQ ID NO 445
<211> LENGTH: 107
<212> TYPE: PRT
<213> ORGANISM: Artificial Sequence
<220> FEATURE:
<223> OTHER INFORMATION: Synthetic

<400> SEQUENCE: 445

Asp Ile Gln Leu Thr Gln Ser Pro Ser Phe Leu Ser Ala Ser Val Gly
  1               5                  10                  15

Asp Arg Val Thr Ile Thr Cys Arg Ala Ser Gln Gly Ile Ile Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys His Gln Leu Lys Ser Tyr Pro Ile
                 85                  90                  95

Thr Phe Gly Gln Gly Thr Arg Leu Glu Ile Lys
            100                 105

<210> SEQ ID NO 446
<211> LENGTH: 349
<212> TYPE: DNA
<213> ORGANISM: Artificial Sequence
<220> FEATURE:
<223> OTHER INFORMATION: Synthetic

<400> SEQUENCE: 446
caggtgcagc tggtgcagtc tggggctgag gtgaagaagc ctggggcctc agtgaaggtc      60
tcctgcaagg cttctagata caccttcacc agttatgata tcaactgggt gcgacaggcc     120
actggacaag gcttgagtg gatgggatgg atgaacccaa acagtggtaa cacaggctat      180
gcacagaagt tccagggcag agtcaccatg accaggaaca cctccacaag cacagcctac     240
atggagctga gcagcctgag atctgaggac acggccgtgt attactgtgc gagagtacga     300 cgctttttg actactgggg ccagggaacc ctggtcaccg tctcctcag                  349
```

<210> SEQ ID NO 447
<211> LENGTH: 116
<212> TYPE: PRT
<213> ORGANISM: Artificial Sequence
<220> FEATURE:
<223> OTHER INFORMATION: Synthetic

<400> SEQUENCE: 447

```
Gln Val Gln Leu Val Gln Ser Gly Ala Glu Val Lys Lys Pro Gly Ala
 1               5                  10                  15

Ser Val Lys Val Ser Cys Lys Ala Ser Arg Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Arg Phe Phe Asp Tyr Trp Gly Gln Gly Thr Leu Val
            100                 105                 110

Thr Val Ser Ser
        115
```

<210> SEQ ID NO 448
<211> LENGTH: 322
<212> TYPE: DNA
<213> ORGANISM: Artificial Sequence
<220> FEATURE:
<223> OTHER INFORMATION: Synthetic

<400> SEQUENCE: 448

```
gacatccagt tgacccagtc tccatccttc ctgtctgcat ctgtaggaga cagagtcacc      60
atcacttgcc gggccagtca gggcattatc agttatttag cctggtatca gcaaaaacca     120
gggaaagccc ctaagctcct gatctatgct gcatccactt tgcaaagtgg ggtcccatca     180
aggttcagcg gcagtggatc tgggacagaa ttcactctca caatcagcag cctgcagcct     240
gaagattttg caacttatta ctgtcaccag cttaaaagtt acccgatcac cttcggccaa     300
gggacacgac tggagattaa ac                                              322
```

<210> SEQ ID NO 449
<211> LENGTH: 107
<212> TYPE: PRT
<213> ORGANISM: Artificial Sequence
<220> FEATURE:
<223> OTHER INFORMATION: Synthetic

<400> SEQUENCE: 449

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Tyr Cys His Gln Leu Lys Ser Tyr Pro Ile
                85                  90                  95

Thr Phe Gly Gln Gly Thr Arg Leu Glu Ile Lys
            100                 105

<210> SEQ ID NO 450
<211> LENGTH: 349
<212> TYPE: DNA
<213> ORGANISM: Artificial Sequence
<220> FEATURE:
<223> OTHER INFORMATION: Synthetic

<400> SEQUENCE: 450
caggtgcagc tggtggagtc tgggggaggc ttggtcaagc ctggagggtc cctgagactc      60
tcctgtgcag cctctggatt caccctcagt gactactaca tgagctggat ccgccaggct     120
ccagggaagg gctggagtg gtttcatac attaggagaa gtggtaatac catatactac       180
gcagactctg tgaagggccg attcaccatc tccagggaca acgccaagaa ctcactgtat     240
ctgcaaatga acagcctgag agccgaggac acggccgtgt attactgtgc gagagggggg     300
gactgggcgg acgtctgggg gcaagggacc acggtcaccg tctcctcag                 349

<210> SEQ ID NO 451
<211> LENGTH: 116
<212> TYPE: PRT
<213> ORGANISM: Artificial Sequence
<220> FEATURE:
<223> OTHER INFORMATION: Synthetic

<400> SEQUENCE: 451

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Leu Ser Asp Tyr
            20                  25                  30

Tyr Met Ser Trp Ile Arg Gln Ala Pro Gly Lys Gly Leu Glu Trp Val
        35                  40                  45

Ser Tyr Ile Arg Arg Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Trp Ala Asp Val Trp Gly Gln Gly Thr Thr Val
            100                 105                 110

Thr Val Ser Ser
        115

<210> SEQ ID NO 452
<211> LENGTH: 322
<212> TYPE: DNA
<213> ORGANISM: Artificial Sequence
<220> FEATURE:
<223> OTHER INFORMATION: Synthetic

<400> SEQUENCE: 452
gacatccaga tgacccagtc tccatcctca ctgtctgcat ctgtaggaga cagagtcacc      60
atcacttgtc gggcgagtca gggcattagc atttatttag cctggtttca gcagaaacca    120
gggaaagccc ctaagtccct gatctatgct gcatccagtt tgcaaagtgg ggtcccatca    180
```

```
aggttcagcg gcagtggatc tgggacagat ttcactctca ccatcagcag cctgcagcct      240
gaagattttg caacttatta ctgccaacag tataatagtt acccgtacac ttttggccag      300
gggaccaagc tggagatcaa ac                                               322
```

<210> SEQ ID NO 453
<211> LENGTH: 107
<212> TYPE: PRT
<213> ORGANISM: Artificial Sequence
<220> FEATURE:
<223> OTHER INFORMATION: Synthetic

<400> SEQUENCE: 453

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ile Tyr
             20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105
```

<210> SEQ ID NO 454
<211> LENGTH: 349
<212> TYPE: DNA
<213> ORGANISM: Artificial Sequence
<220> FEATURE:
<223> OTHER INFORMATION: Synthetic

<400> SEQUENCE: 454

```
caggtgcagc tggtggagtc tgggggagac ttggtcaggc ctggagggtc cctgagactc      60
tcctgtacag cctctggatt caccctcagt gactactaca tgagctggat ccgtcaggct      120
ccagggaagg ggctggagtg ggtttcatac attaggagaa gtggtaatac catatactac      180
gcagactctg tgaagggccg attcaccatc tccagggaca acgccaagaa ctcactgtat      240
ctgcaaatga acagcctgag agccgaggac acggccgtat attactgtgc gagggggggg      300
gactgggcgg acgtctgggg ccaagggacc acggtcaccg tctcctcag                  349
```

<210> SEQ ID NO 455
<211> LENGTH: 116
<212> TYPE: PRT
<213> ORGANISM: Artificial Sequence
<220> FEATURE:
<223> OTHER INFORMATION: Synthetic

<400> SEQUENCE: 455

```
Gln Val Gln Leu Val Glu Ser Gly Gly Asp Leu Val Arg Pro Gly Gly
  1               5                  10                  15

Ser Leu Arg Leu Ser Cys Thr Ala Ser Gly Phe Thr Leu Ser Asp Tyr
             20                  25                  30

Tyr Met Ser Trp Ile Arg Gln Ala Pro Gly Lys Gly Leu Glu Trp Val
         35                  40                  45

Ser Tyr Ile Arg Arg Ser Gly Asn Thr Ile Tyr Tyr Ala Asp Ser Val
```

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Trp Ala Asp Val Trp Gly Gln Gly Thr Thr Val
                100                 105                 110

Thr Val Ser Ser
        115

<210> SEQ ID NO 456
<211> LENGTH: 322
<212> TYPE: DNA
<213> ORGANISM: Artificial Sequence
<220> FEATURE:
<223> OTHER INFORMATION: Synthetic

<400> SEQUENCE: 456
gacatccaga tgacccagtc tccatcctca ctgtctgcct ctgtgggaga cagagtcacc      60
atcacttgtc gggcgagtca gggcattagc atttatttag cctggtttca gcagaaacca     120
gggaaagccc ctaagtccct gatctatgct gcatccagtt tgcaacgtgg ggtcccatca     180
aagttcagcg gcagtggatc tgggacagat ttcactctca ccatcagtag cctgcagcct     240
gaagattttg caacttatta ctgccaacag tataatagtt acccgtacac ttttggccag     300
gggaccaagc tggagatcaa ac                                              322

<210> SEQ ID NO 457
<211> LENGTH: 107
<212> TYPE: PRT
<213> ORGANISM: Artificial Sequence
<220> FEATURE:
<223> OTHER INFORMATION: Synthetic

<400> SEQUENCE: 457

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ile Tyr
                 20                  25                  30

Leu Ala Trp Phe Gln Gln Lys Pro Gly Lys Ala Pro Lys Ser Leu Ile
             35                  40                  45

Tyr Ala Ala Ser Ser Leu Gln Arg Gly Val Pro Ser Lys Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105

<210> SEQ ID NO 458
<211> LENGTH: 352
<212> TYPE: DNA
<213> ORGANISM: Artificial Sequence
<220> FEATURE:
<223> OTHER INFORMATION: Synthetic

<400> SEQUENCE: 458
caggttcagc tggtgcagtc tggagctgag gtgaagaagc ctggggcctc agtgaaggtc      60
```

```
tcctgcaagg cttctggtta cacctttacc aactatggta tcagctgggt gcgacaggcc    120
cctggacaag ggcttgagtg gatgggatgg atcagcgttt acaatggtaa cataaactat    180
gcacagaagc tccagggcag agtcaccatg accacagaca catccacgag cacagcctac    240
atggagctga ggagcctgag atctgacgac acggccgtgt attactgtgc gagagggagt    300
ggctacgatt ttgactactg gggccaagga accctggtca ccgtctcctc ag            352
```

<210> SEQ ID NO 459
<211> LENGTH: 117
<212> TYPE: PRT
<213> ORGANISM: Artificial Sequence
<220> FEATURE:
<223> OTHER INFORMATION: Synthetic

<400> SEQUENCE: 459

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Ile Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Gly Tyr Asp Phe Asp Tyr Trp Gly Gln Gly Thr Leu
            100                 105                 110

Val Thr Val Ser Ser
        115
```

<210> SEQ ID NO 460
<211> LENGTH: 322
<212> TYPE: DNA
<213> ORGANISM: Artificial Sequence
<220> FEATURE:
<223> OTHER INFORMATION: Synthetic

<400> SEQUENCE: 460

```
gccatccaga tgacccagtc tccatcctcc ctgtctgcat ctgtaggaga cagagtcacc    60
atcacttgcc gggcaagtca ggacattaga aatgctttag ctggtatca gcagaaacca    120 gggaaagccc ctaagctcct gatctatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gattacaatt acccgtacac ttttggccag    300
gggaccaagc tggagatcaa ac                                             322
```

<210> SEQ ID NO 461
<211> LENGTH: 107
<212> TYPE: PRT
<213> ORGANISM: Artificial Sequence
<220> FEATURE:
<223> OTHER INFORMATION: Synthetic

<400> SEQUENCE: 461

```
Ala Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Arg Asn Ala
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Tyr
                85                  90                  95

Thr Phe Gly Gln Gly Thr Lys Leu Glu Ile Lys
            100                 105
```

<210> SEQ ID NO 462
<211> LENGTH: 352
<212> TYPE: DNA
<213> ORGANISM: Artificial Sequence
<220> FEATURE:
<223> OTHER INFORMATION: Synthetic

<400> SEQUENCE: 462

```
caggttcagc tggtgcagtc tggagctgag gtgaagaagc ctggggcctc agtgaaggtc     60
tcctgcaagg cttctggtta cacctttacc aactatggta tcagctgggt gcgacaggcc    120
cctggacaag ggcttgagtg gatgggatgg atcagcgttt acaatggtaa cataaactat    180
gcacagaagc tccagggcag agtcaccatg accacagaca catccacgag cacagcctac    240
atggagctga ggagcctgag atctgacgac acggccgtgt attactgtgc gagagggagt    300
ggctacgatt ttgactactg gggccaagga accctggtca ccgtctcctc ag            352
```

<210> SEQ ID NO 463
<211> LENGTH: 117
<212> TYPE: PRT
<213> ORGANISM: Artificial Sequence
<220> FEATURE:
<223> OTHER INFORMATION: Synthetic

<400> SEQUENCE: 463

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Ile Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Gly Tyr Asp Phe Asp Tyr Trp Gly Gln Gly Thr Leu
            100                 105                 110

Val Thr Val Ser Ser
        115
```

<210> SEQ ID NO 464
<211> LENGTH: 322
<212> TYPE: DNA
<213> ORGANISM: Artificial Sequence
<220> FEATURE:
<223> OTHER INFORMATION: Synthetic

<400> SEQUENCE: 464

```
gccatccaga tgacccagtc tccatcctcc ctgtctgcat ctgtaggaga cagagtcacc      60
atcacttgcc gggcaagtca ggacattaga aatgctttag ctggtatca gcagaaacca     120
gggaaagccc ctaagctcct gatctatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gattacaatt acccgtacac ttttggccag    300
gggaccaagc tggagatcaa ac                                             322
```

<210> SEQ ID NO 465
<211> LENGTH: 107
<212> TYPE: PRT
<213> ORGANISM: Artificial Sequence
<220> FEATURE:
<223> OTHER INFORMATION: Synthetic

<400> SEQUENCE: 465

```
Ala Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Ile Arg Asn Ala
            20                  25                  30
Leu Gly Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Tyr Asn Tyr Pro Tyr
                85                  90                  95
Thr Phe Gly Gln Gly Thr Lys Leu Glu Ile Lys
            100                 105
```

<210> SEQ ID NO 466
<211> LENGTH: 367
<212> TYPE: DNA
<213> ORGANISM: Artificial Sequence
<220> FEATURE:
<223> OTHER INFORMATION: Synthetic

<400> SEQUENCE: 466

```
caggttcagc tggtgcagtc tggagctgag gtgaagaagc ctggggcctc agtgaaggtc      60
tcctgcaagg cttctgctta cacctttaat agatatggta tcagctgggt gcgacaggcc    120
cctggacaag gcttgagtg gatgggatgg atcagcgctt acactggtaa cacaaactat     180
gcacagaagc tccagggcag agtcaccatg accacagaca tccacgag cacagcctac      240
atggagctga ggagcctgag atctgacgac acggccgtgt attactgtgc gagagataag    300
tcgattttttg gagtggttag agggtttgac tactggggcc aaggaaccct ggtcaccgtc   360
tcctcag                                                              367
```

<210> SEQ ID NO 467
<211> LENGTH: 122
<212> TYPE: PRT
<213> ORGANISM: Artificial Sequence
<220> FEATURE:
<223> OTHER INFORMATION: Synthetic

<400> SEQUENCE: 467

Gln Val Gln Leu Val Gln Ser Gly Ala Glu Val Lys Lys Pro Gly Ala
1               5                   10                  15

Ser Val Lys Val Ser Cys Lys Ala Ser Ala Tyr Thr Phe Asn Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Lys Ser Ile Phe Gly Val Val Arg Gly Phe Asp Tyr Trp
            100                 105                 110

Gly Gln Gly Thr Leu Val Thr Val Ser Ser
        115                 120

<210> SEQ ID NO 468
<211> LENGTH: 322
<212> TYPE: DNA
<213> ORGANISM: Artificial Sequence
<220> FEATURE:
<223> OTHER INFORMATION: Synthetic

<400> SEQUENCE: 468
gaaatagtga tgacgcagtc tccagccacc ctgtctgtgt ctccagggga aagagccacc      60
ctctcctgca gggccagtca gagtgttagc agcagcttag cctggtacca gcagaaacct    120
ggccaggctc ccaggctcct catctatggt gcatctacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctctcac tttcggcgga    300
gggaccaagg tggagatcaa ac                                              322

<210> SEQ ID NO 469
<211> LENGTH: 107
<212> TYPE: PRT
<213> ORGANISM: Artificial Sequence
<220> FEATURE:
<223> OTHER INFORMATION: Synthetic

<400> SEQUENCE: 469

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 470
<211> LENGTH: 367
<212> TYPE: DNA
<213> ORGANISM: Artificial Sequence
<220> FEATURE:
<223> OTHER INFORMATION: Synthetic

<400> SEQUENCE: 470

```
caggttcagc tggtgcagtc tggagctgag gtgaagaagc ctggggcctc agtgaaggtc      60
tcctgcaagg cttctgctta caccttaat agatatggta tcagctgggt gcgacaggcc     120
cctggacaag ggcttgagtg gatgggatgg atcagcgctt acactggtaa cacaaactat    180
gcacagaagc tccagggcag agtcaccatg accacagaca catccacgag cacagcctac    240
atggagctga ggagcctgag atctgacgac acggccgtgt attactgtgc gagagataag    300
tcgattttg gagtggttag agggtttgac tactggggcc aaggaaccct ggtcaccgtc     360
tcctcag                                                              367
```

<210> SEQ ID NO 471
<211> LENGTH: 122
<212> TYPE: PRT
<213> ORGANISM: Artificial Sequence
<220> FEATURE:
<223> OTHER INFORMATION: Synthetic

<400> SEQUENCE: 471

Gln Val Gln Leu Val Gln Ser Gly Ala Glu Val Lys Lys Pro Gly Ala
1               5                   10                  15
Ser Val Lys Val Ser Cys Lys Ala Ser Ala Tyr Thr Phe Asn Arg Tyr
                20                  25                  30
Gly Ile Ser Trp Val Arg Gln Ala Pro Gly Gln Gly Leu Glu Trp Met
            35                  40                  45
Gly Trp Ile Ser Ala Tyr Thr Gly Asn Thr Asn Tyr Ala Gln Lys Leu
        50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Lys Ser Ile Phe Gly Val Val Arg Gly Phe Asp Tyr Trp
                100                 105                 110
Gly Gln Gly Thr Leu Val Thr Val Ser Ser
        115                 120

<210> SEQ ID NO 472
<211> LENGTH: 322
<212> TYPE: DNA
<213> ORGANISM: Artificial Sequence
<220> FEATURE:
<223> OTHER INFORMATION: Synthetic

<400> SEQUENCE: 472

```
gaaatagtga tgacgcagtc tccagccacc ctgtctgtgt ctccagggga aagagccacc      60
ctctcctgca gggccagtca gagtgttagc agcagcttag cctggtacca gcagaaacct    120
ggccaggctc ccaggctcct catctatggt gcatctacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctctcac tttcggcgga    300
```
gggaccaagg tggagatcaa ac         322

<210> SEQ ID NO 473
<211> LENGTH: 107
<212> TYPE: PRT
<213> ORGANISM: Artificial Sequence
<220> FEATURE:
<223> OTHER INFORMATION: Synthetic

<400> SEQUENCE: 473

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 474
<211> LENGTH: 352
<212> TYPE: DNA
<213> ORGANISM: Artificial Sequence
<220> FEATURE:
<223> OTHER INFORMATION: Synthetic

<400> SEQUENCE: 474
caggttcagc tggtgcagtc tggagctgag gtgaagaagc ctggggcctc agtgaaggtc      60
tcctgcaagg cttctggtta cacctttacc aactatggca tcagctgggt gcgacaggcc     120
cctggacaag gcttgagtg gatgggatgg atcagtgttt acaatggcaa cacaaactat     180
gcacagaagc tccagggcag agtcaccatg accacagaca tccacgag cacagcctac       240 atggagctga ggagcctgag atctgacgac acggccgtgt attactgtgc gagagggagt    300
ggctacgatt tgactactg gggccaagga accctggtca ccgtctcctc ag             352

<210> SEQ ID NO 475
<211> LENGTH: 117
<212> TYPE: PRT
<213> ORGANISM: Artificial Sequence
<220> FEATURE:
<223> OTHER INFORMATION: Synthetic

<400> SEQUENCE: 475

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95
Ala Arg Gly Ser Gly Tyr Asp Phe Asp Tyr Trp Gly Gln Gly Thr Leu
            100                 105                 110
Val Thr Val Ser Ser
        115

<210> SEQ ID NO 476
<211> LENGTH: 322
<212> TYPE: DNA
<213> ORGANISM: Artificial Sequence
<220> FEATURE:
<223> OTHER INFORMATION: Synthetic

<400> SEQUENCE: 476
gccatccaga tgacccagtc tccatcctcc ctgtctgcat ctgtaggaga cagagtcacc    60
atcacttgcc gggcaagtca ggacattaga aatgatttag ctggtatca gcagaaacca   120 gggaaagccc ctaagctcct gatctatact gcttccagtt tacaaagtgg ggtcccatca   180
aggttcagcg gcagtggatc tggcacagat ttcactctca ccatcagcag cctgcagcct   240
gaagattttg caacttatta ctgtctccaa gataatagtt acccgtacac ttttggccag   300
gggaccaagc tggagatcaa ac                                             322

<210> SEQ ID NO 477
<211> LENGTH: 107
<212> TYPE: PRT
<213> ORGANISM: Artificial Sequence
<220> FEATURE:
<223> OTHER INFORMATION: Synthetic

<400> SEQUENCE: 477

Ala Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Ile Arg Asn Asp
            20                  25                  30
Leu Gly Trp Tyr Gln Gln Lys Pro Gly Lys Ala Pro Lys Leu Leu Ile
        35                  40                  45
Tyr Thr Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Asn Ser Tyr Pro Tyr
            85                  90                  95
Thr Phe Gly Gln Gly Thr Lys Leu Glu Ile Lys
            100                 105

<210> SEQ ID NO 478
<211> LENGTH: 352
<212> TYPE: DNA
<213> ORGANISM: Artificial Sequence
<220> FEATURE:
<223> OTHER INFORMATION: Synthetic

<400> SEQUENCE: 478
caggttcagc tggtgcagtc tggagctgag gtgaagaagc ctggggcctc agtgaaggtc    60
tcctgcaagg cttctggtta cacctttacc aactatggca tcagctgggt gcgacaggcc   120
cctggacaag gccttgagtg gatgggatgg atcagtgttt acaatggcaa cacaaactat   180

```
gcacagaagc tccagggcag agtcaccatg accacagaca catccacgag cacagcctac    240
atggagctga ggagcctgag atctgacgac acggccgtgt attactgtgc gagagggagt    300
ggctacgatt ttgactactg gggccaagga accctggtca ccgtctcctc ag            352
```

<210> SEQ ID NO 479
<211> LENGTH: 117
<212> TYPE: PRT
<213> ORGANISM: Artificial Sequence
<220> FEATURE:
<223> OTHER INFORMATION: Synthetic

<400> SEQUENCE: 479

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Gly Tyr Asp Phe Asp Tyr Trp Gly Gln Gly Thr Leu
            100                 105                 110

Val Thr Val Ser Ser
        115
```

<210> SEQ ID NO 480
<211> LENGTH: 322
<212> TYPE: DNA
<213> ORGANISM: Artificial Sequence
<220> FEATURE:
<223> OTHER INFORMATION: Synthetic

<400> SEQUENCE: 480

```
gccatccaga tgacccagtc tccttcctcc ctgtctgcat ctgttggaga cagagtcgcc     60
atcacttgcc gggcaagtca ggacattaga aatgatttag gctggtatca gcagaaacca    120
gggaaagccc ctaagcttct gatccatact gcttccagtt tacaaagtgg ggtcccatca    180
aggttcagcg gcagtggatc tgggacagat ttcactctca ccatcagcaa cctgcagcct    240
gaagattttg ccacttatta ctgtctccaa gataatagtt acccgtacac ttttggccag    300
gggaccaagc tggagatcaa ac                                             322
```

<210> SEQ ID NO 481
<211> LENGTH: 107
<212> TYPE: PRT
<213> ORGANISM: Artificial Sequence
<220> FEATURE:
<223> OTHER INFORMATION: Synthetic

<400> SEQUENCE: 481

```
Ala Ile Gln Met Thr Gln Ser Pro Ser Ser Leu Ser Ala Ser Val Gly
 1               5                  10                  15

Asp Arg Val Ala Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
```

His Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Leu Gln Asp Asn Ser Tyr Pro Tyr
                85                  90                  95

Thr Phe Gly Gln Gly Thr Lys Leu Glu Ile Lys
            100                 105

<210> SEQ ID NO 482
<211> LENGTH: 349
<212> TYPE: DNA
<213> ORGANISM: Artificial Sequence
<220> FEATURE:
<223> OTHER INFORMATION: Synthetic

<400> SEQUENCE: 482
caggtgcagc tggtgcagtc tggggctgag gtgaagaagc ctggggcctc agtgaaggtc      60
tcctgcaagg cttctggata caccttcacc ggccagtata tgcactgggt gcgacaggcc     120
cctggacaag gcttgagtg gatgggatgg atcaaccta acagtggtgg cacaaactat       180
gcacagaagt tcagggcag gtcaccatg accaggaca cgtccatcag cacagcctac        240
atggagctga gcaggctgag atctgacgac acggccgtgt attactgtgt gagagaaaag     300
agaggttttg atatctgggg ccaagggaca atggtcaccg tctcttcag                 349

<210> SEQ ID NO 483
<211> LENGTH: 116
<212> TYPE: PRT
<213> ORGANISM: Artificial Sequence
<220> FEATURE:
<223> OTHER INFORMATION: Synthetic

<400> SEQUENCE: 483

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Gln
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Glu Lys Arg Gly Phe Asp Ile Trp Gly Gln Gly Thr Met Val
            100                 105                 110

Thr Val Ser Ser
        115

<210> SEQ ID NO 484
<211> LENGTH: 319
<212> TYPE: DNA
<213> ORGANISM: Artificial Sequence
<220> FEATURE:
<223> OTHER INFORMATION: Synthetic

<400> SEQUENCE: 484

-continued

```
gaaattgtgt tgacacagtc tccagccacc ctgtctttgt ctccagggga aagagccacc      60
ctctcctgca gggccagtca gagtgttagg agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcgact ggcctacttt cggccctggg     300
accaaagtgg atatcaaac                                                  319
```

<210> SEQ ID NO 485
<211> LENGTH: 106
<212> TYPE: PRT
<213> ORGANISM: Artificial Sequence
<220> FEATURE:
<223> OTHER INFORMATION: Synthetic

<400> SEQUENCE: 485

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Arg Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asp Trp Pro Thr
                 85                  90                  95

Phe Gly Pro Gly Thr Lys Val Asp Ile Lys
            100                 105
```

<210> SEQ ID NO 486
<211> LENGTH: 349
<212> TYPE: DNA
<213> ORGANISM: Artificial Sequence
<220> FEATURE:
<223> OTHER INFORMATION: Synthetic

<400> SEQUENCE: 486

```
caggtgcagc tggtgcagtc tggggctgag gtgaagaagc ctggggcctc agtgaaggtc      60
tcctgcaagg cttctggata caccttcacc ggccagtata ttcactgggt tcgacaggcc     120
cctggacaag gacttgagtg gatgggatgg atcaaccctaa acagtggtgg cacaaacttt    180
gcacagaagt ttcaggacag ggtcaccatg accagggaca cgtccatcgg cacagtatac     240
atggaactga ggaggctgac atctgacgac acggccgtat tttattgtgt gagagaaaag     300
agaggttttg atatctgggg ccaagggaca atggtcaccg tttcttcag                 349
```

<210> SEQ ID NO 487
<211> LENGTH: 116
<212> TYPE: PRT
<213> ORGANISM: Artificial Sequence
<220> FEATURE:
<223> OTHER INFORMATION: Synthetic

<400> SEQUENCE: 487

```
Gln Val Gln Leu Val Gln Ser Gly Ala Glu Val Lys Lys Pro Gly Ala
  1               5                  10                  15
```

```
Ser Val Lys Val Ser Cys Lys Ala Ser Gly Tyr Thr Phe Thr Gly Gln
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Phe Ala Gln Lys Phe
    50                  55                  60

Gln Asp Arg Val Thr Met Thr Arg Asp Thr Ser Ile Gly Thr Val Tyr
65                  70                  75                  80

Met Glu Leu Arg Arg Leu Thr Ser Asp Asp Thr Ala Val Phe Tyr Cys
                85                  90                  95

Val Arg Glu Lys Arg Gly Phe Asp Ile Trp Gly Gln Gly Thr Met Val
            100                 105                 110

Thr Val Ser Ser
        115

<210> SEQ ID NO 488
<211> LENGTH: 319
<212> TYPE: DNA
<213> ORGANISM: Artificial Sequence
<220> FEATURE:
<223> OTHER INFORMATION: Synthetic

<400> SEQUENCE: 488
gaaattgtgt tgacacagtc tccagccacc ctgtctttgt ctccagggga aagagccacc     60
ctctcctgca gggccagtca gagtgttagg agctactttg cctggtacca acagaaacct    120
ggccaggctc ccaggtcct catctatgat gcatccatca gggccaccgg catcccagcc    180
aggttcagtg gcagtgggtc tgggacagac ttcagtctca ccattgacag cctagagcct    240
gaagattttg cagtttatta ctgtcagcag cgtagcgact ggcctacttt cggccctggg    300
accaaagtgg atatcaaac                                                 319

<210> SEQ ID NO 489
<211> LENGTH: 106
<212> TYPE: PRT
<213> ORGANISM: Artificial Sequence
<220> FEATURE:
<223> OTHER INFORMATION: Synthetic

<400> SEQUENCE: 489

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Phe Ala Trp Tyr Gln Gln Lys Pro Gly Gln Ala Pro Arg Val Leu Ile
        35                  40                  45

Tyr Asp Ala Ser Ile Arg Ala Thr Gly Ile Pro Ala Arg Phe Ser Gly
    50                  55                  60

Ser Gly Ser Gly Thr Asp Phe Ser Leu Thr Ile Asp Ser Leu Glu Pro
65                  70                  75                  80

Glu Asp Phe Ala Val Tyr Tyr Cys Gln Gln Arg Ser Asp Trp Pro Thr
                85                  90                  95

Phe Gly Pro Gly Thr Lys Val Asp Ile Lys
            100                 105

<210> SEQ ID NO 490
<211> LENGTH: 352
<212> TYPE: DNA
<213> ORGANISM: Artificial Sequence
```

```
<220> FEATURE:
<223> OTHER INFORMATION: Synthetic

<400> SEQUENCE: 490
caggttcagc tggtgcagtc tggagctgag gtgaagaagc ctggggcctc agtgaaggtc      60
tcctgcaagg cttctggtta cacctttacc aactatggta tcagctgggt gcgacaggcc     120
cctggacaag gcttgagtg gatgggatgg atcagtattt acaatggtaa cacaaactat      180
gcacagaagc tccagggcag agtcaccatg accacagaca catccacgag cacagcctac     240
atggagctga ggagcctgag atctgacgac acggccgtgt attactgtgc gagaggtagt     300
ggctacaatt tcgaccactg gggccaagga accctggtca ccgtctcctc ag             352

<210> SEQ ID NO 491
<211> LENGTH: 117
<212> TYPE: PRT
<213> ORGANISM: Artificial Sequence
<220> FEATURE:
<223> OTHER INFORMATION: Synthetic

<400> SEQUENCE: 491

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ile Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Gly Tyr Asn Phe Asp His Trp Gly Gln Gly Thr Leu
            100                 105                 110

Val Thr Val Ser Ser
        115

<210> SEQ ID NO 492
<211> LENGTH: 322
<212> TYPE: DNA
<213> ORGANISM: Artificial Sequence
<220> FEATURE:
<223> OTHER INFORMATION: Synthetic

<400> SEQUENCE: 492
gccatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagctcct gatctatgct gcatccagtt tacaaagtgg ggtcccatca     180
aggttcagcg gcagtggatc tggcacagat tcactctca ccatcagcag cctgcagcct     240
gaagattttg caacttatta ctgtctacaa gataacactt atccgtacac ttttggccag     300
gggaccaagc tggagatcaa ac                                              322

<210> SEQ ID NO 493
<211> LENGTH: 107
<212> TYPE: PRT
<213> ORGANISM: Artificial Sequence
<220> FEATURE:
```

-continued

<223> OTHER INFORMATION: Synthetic

<400> SEQUENCE: 493

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Asn Thr Tyr Pro Tyr
                85                  90                  95

Thr Phe Gly Gln Gly Thr Lys Leu Glu Ile Lys
            100                 105

<210> SEQ ID NO 494
<211> LENGTH: 352
<212> TYPE: DNA
<213> ORGANISM: Artificial Sequence
<220> FEATURE:
<223> OTHER INFORMATION: Synthetic

<400> SEQUENCE: 494
caggttcagc tggtgcagtc tggagctgag gtgaagaagc ctggggcctc agtgaaggtc      60
tcctgcaagg cttctggtta cacctttacc aactatggta tcggctgggt gcgacaggcc     120
cctggacaag gcttgagtg gatgggatgg atcagtattt acaatggtaa cacaaattat      180
gcacagaggc tccagggcag agtcaccatg accacagaca catccacgag cacagccttc     240
atggacctga ggagcctgaa atctgacgac acggccgttt attactgtgc gagaggtagt     300
ggctacaatt tcgaccactg gggccaggga accctggtca ccgtctcctc ag             352

<210> SEQ ID NO 495
<211> LENGTH: 117
<212> TYPE: PRT
<213> ORGANISM: Artificial Sequence
<220> FEATURE:
<223> OTHER INFORMATION: Synthetic

<400> SEQUENCE: 495

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Gly Trp Val Arg Gln Ala Pro Gly Gln Gly Leu Glu Trp Met
        35                  40                  45

Gly Trp Ile Ser Ile Tyr Asn Gly Asn Thr Asn Tyr Ala Gln Arg Leu
50                  55                  60

Gln Gly Arg Val Thr Met Thr Thr Asp Thr Ser Thr Ser Thr Ala Phe
65                  70                  75                  80

Met Asp Leu Arg Ser Leu Lys Ser Asp Asp Thr Ala Val Tyr Tyr Cys
                85                  90                  95

Ala Arg Gly Ser Gly Tyr Asn Phe Asp His Trp Gly Gln Gly Thr Leu
            100                 105                 110

Val Thr Val Ser Ser

<210> SEQ ID NO 496
<211> LENGTH: 322
<212> TYPE: DNA
<213> ORGANISM: Artificial Sequence
<220> FEATURE:
<223> OTHER INFORMATION: Synthetic

<400> SEQUENCE: 496

```
gccatccaga tgacccagtc tccatcctcc ctgtctgcat ctgtaggaga cagagtcacc    60
atcacttgcc gggcaagtca gggcattaga aatgatttag gctggtatca gcagataccg   120
gggaaagccc ctaaactcct gatctatgct gcatccagtt tacaaagtgg ggtcccgtca   180
aggttcagcg gcagtggatc tggcacagat ttcactctca ccatcagcaa cctgcagcct   240
gaagattttg cagtttattt ctgtctacaa gataacactt atccgtacac ttttggccag   300
gggaccaagc tggagatcaa ac                                            322
```

<210> SEQ ID NO 497
<211> LENGTH: 107
<212> TYPE: PRT
<213> ORGANISM: Artificial Sequence
<220> FEATURE:
<223> OTHER INFORMATION: Synthetic

<400> SEQUENCE: 497

```
Ala Ile Gln Met Thr Gln Ser Pro Ser Ser Leu Ser Ala Ser Val Gly
  1               5                  10                  15
Asp Arg Val Thr Ile Thr Cys Arg Ala Ser Gln Gly Ile Arg Asn Asp
             20                  25                  30
Leu Gly Trp Tyr Gln Gln Ile Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Asn Leu Gln Pro
 65                  70                  75                  80
Glu Asp Phe Ala Val Tyr Phe Cys Leu Gln Asp Asn Thr Tyr Pro Tyr
                 85                  90                  95
Thr Phe Gly Gln Gly Thr Lys Leu Glu Ile Lys
            100                 105
```

<210> SEQ ID NO 498
<211> LENGTH: 352
<212> TYPE: DNA
<213> ORGANISM: Artificial Sequence
<220> FEATURE:
<223> OTHER INFORMATION: Synthetic

<400> SEQUENCE: 498

```
caggttcagc tggtgcagtc tggagctgag gtgaagaagc ctggggcctc agtgaaggtc    60
tcctgcaagg cttctggtta cacctttacc aactatggta tcagctgggt gcgacaggcc   120
cctggacaag gcttgagtg gatgggatgg atcagcgttt acaatggtaa aacaaactat   180
gcacagaagc tccagggcag agtcaccatg accacagaca catccacgag cacagcctac   240
atggagctga ggagcctgag atctgacgac acggccgtgt attactgtgc gagagggagt   300
ggctacgatt ttgactactg gggccaagga accctggtca ccgtctcctc ag           352
```

<210> SEQ ID NO 499

```
<211> LENGTH: 117
<212> TYPE: PRT
<213> ORGANISM: Artificial Sequence
<220> FEATURE:
<223> OTHER INFORMATION: Synthetic

<400> SEQUENCE: 499
```

| Gln | Val | Gln | Leu | Val | Gln | Ser | Gly | Ala | Glu | Val | Lys | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Lys | Val | Ser | Cys | Lys | Ala | Ser | Gly | Tyr | Thr | Phe | Thr | Asn | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Ile | Ser | Trp | Val | Arg | Gln | Ala | Pro | Gly | Gln | Gly | Leu | Glu | Trp | Met |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Trp | Ile | Ser | Val | Tyr | Asn | Gly | Lys | Thr | Asn | Tyr | Ala | Gln | Lys | Leu |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Gln | Gly | Arg | Val | Thr | Met | Thr | Thr | Asp | Thr | Ser | Thr | Ser | Thr | Ala | Tyr |
|-----|-----|-----|-----|-----|-----|-----|-----|-----|-----|-----|-----|-----|-----|-----|-----|
| 65  |     |     |     | 70  |     |     |     |     | 75  |     |     |     |     | 80  |     |

| Met | Glu | Leu | Arg | Ser | Leu | Arg | Ser | Asp | Asp | Thr | Ala | Val | Tyr | Tyr | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Gly | Ser | Gly | Tyr | Asp | Phe | Asp | Tyr | Trp | Gly | Gln | Gly | Thr | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Val | Thr | Val | Ser | Ser |
|-----|-----|-----|-----|-----|
|     |     |     | 115 |     |

```
<210> SEQ ID NO 500
<211> LENGTH: 322
<212> TYPE: DNA
<213> ORGANISM: Artificial Sequence
<220> FEATURE:
<223> OTHER INFORMATION: Synthetic

<400> SEQUENCE: 500
gccatccaga tgacccagtc tccatcctcc ctgtctgcat ctgtaggaga cagagtcacc      60
atcacttgcc gggcaagtca gggcattaga aatgctttag gctggtatca gcagaaacca     120
gggaaagccc ctaagctcct gatctatgct tcatccagtt tacaaagtgg ggtcccatca     180
aggttcagcg gcagtggatc tggcacagat ttcactctca ccatcagcag cctgcagcct     240
gaagattttg caacttatta ctgtctacaa gattataatt acccgtacac ttttggccag     300
gggaccaagc tggagatcaa ac                                              322

<210> SEQ ID NO 501
<211> LENGTH: 107
<212> TYPE: PRT
<213> ORGANISM: Artificial Sequence
<220> FEATURE:
<223> OTHER INFORMATION: Synthetic

<400> SEQUENCE: 501
```

| Ala | Ile | Gln | Met | Thr | Gln | Ser | Pro | Ser | Ser | Leu | Ser | Ala | Ser | Val | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Arg | Val | Thr | Ile | Thr | Cys | Arg | Ala | Ser | Gln | Gly | Ile | Arg | Asn | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Gly | Trp | Tyr | Gln | Gln | Lys | Pro | Gly | Lys | Ala | Pro | Lys | Leu | Leu | Ile |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Tyr | Ala | Ser | Ser | Ser | Leu | Gln | Ser | Gly | Val | Pro | Ser | Arg | Phe | Ser | Gly |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Ser | Gly | Ser | Gly | Thr | Asp | Phe | Thr | Leu | Thr | Ile | Ser | Ser | Leu | Gln | Pro |
|-----|-----|-----|-----|-----|-----|-----|-----|-----|-----|-----|-----|-----|-----|-----|-----|
| 65  |     |     |     | 70  |     |     |     |     | 75  |     |     |     |     | 80  |     |

```
Glu Asp Phe Ala Thr Tyr Tyr Cys Leu Gln Asp Tyr Asn Tyr Pro Tyr
                85                  90                  95

Thr Phe Gly Gln Gly Thr Lys Leu Glu Ile Lys
            100                 105

<210> SEQ ID NO 502
<211> LENGTH: 352
<212> TYPE: DNA
<213> ORGANISM: Artificial Sequence
<220> FEATURE:
<223> OTHER INFORMATION: Synthetic

<400> SEQUENCE: 502
caggttcagc tggtgcagtc tggacctgag gtgaagaagc ctggggcctc agtgaaggtc     60
tcctgcaagg cttctggtta ccctttacc aactatggta tcagttgggt gcgacaggcc    120
cctggacaag gcttgagtg gatgggatgg atcagcgttt acaatggtaa acaaactat     180 gcacagaagt tccagggcag agtcaccatg accacagaca catccacgag cacagcctac    240
atggacctga ggagcctgag atctgacgac acggccgtat attactgtgc gagagggagt    300
ggctacgatt ttgactactg gggccaggga accctggtca ccgtctcctc ag           352

<210> SEQ ID NO 503
<211> LENGTH: 117
<212> TYPE: PRT
<213> ORGANISM: Artificial Sequence
<220> FEATURE:
<223> OTHER INFORMATION: Synthetic

<400> SEQUENCE: 503

Gln Val Gln Leu Val Gln Ser Gly Pro Glu Val Lys Lys Pro Gly Ala
  1               5                  10                  15

Ser Val Lys Val Ser Cys Lys Ala Ser Gly Tyr Thr Phe Thr Asn Tyr
                20                  25                  30

Gly Ile Ser Trp Val Arg Gln Ala Pro Gly Gln Gly Leu Glu Trp Met
            35                  40                  45

Gly Trp Ile Ser Val Tyr Asn Gly Lys Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Gly Ser Gly Tyr Asp Phe Asp Tyr Trp Gly Gln Gly Thr Leu
            100                 105                 110

Val Thr Val Ser Ser
        115

<210> SEQ ID NO 504
<211> LENGTH: 322
<212> TYPE: DNA
<213> ORGANISM: Artificial Sequence
<220> FEATURE:
<223> OTHER INFORMATION: Synthetic

<400> SEQUENCE: 504
gccatccaga tgacccagtc tccatcctcc ctgtctgcat ctgtaggaga cagagtcacc     60
atcacttgcc gggcaagtca gggcattaga aatgctttag ctggtatca gcagaaacca    120 gggaaagccc ctaagctcct gatctatgct tcatccagtt tacaaagtgg ggtcccatca    180
aggttcagcg gcagtggatc tggcacagat ttcactctca ccatcagcag cctgcagcct    240
```

```
gaagatttg caacttatta ctgtctacaa gattataatt acccgtacac ttttggccag    300
gggaccaagc tggagatcaa ac                                            322
```

<210> SEQ ID NO 505
<211> LENGTH: 107
<212> TYPE: PRT
<213> ORGANISM: Artificial Sequence
<220> FEATURE:
<223> OTHER INFORMATION: Synthetic

<400> SEQUENCE: 505

```
Ala Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Ala
             20                  25                  30

Leu Gly Trp Tyr Gln Gln Lys Pro Gly Lys Ala Pro Lys Leu Leu Ile
         35                  40                  45

Tyr Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Tyr
                 85                  90                  95

Thr Phe Gly Gln Gly Thr Lys Leu Glu Ile Lys
            100                 105
```

<210> SEQ ID NO 506
<211> LENGTH: 352
<212> TYPE: DNA
<213> ORGANISM: Artificial Sequence
<220> FEATURE:
<223> OTHER INFORMATION: Synthetic

<400> SEQUENCE: 506

```
caggttcagc tggtgcagtc tggagctgag gtgaagaagc ctggggcctc agtgaaggtc    60
tcctgcaagg cttctggtta caccttttacc agctatggta tcagctgggt gcgacaggcc   120
cctggacaag gcttgagtg gatgggatgg atcagtgttt acaatggtaa cacaaactat    180
gcacagaagc tccagggcag agtcaccatg accacagaca catccacgag cacagcctac   240
atggagctga ggagcctgag atctgacgac acggccgtgt attactgtgc gagagggagt   300
ggctacgatt ttgactactg ggccaagga accctggtca ccgtctcctc ag           352
```

<210> SEQ ID NO 507
<211> LENGTH: 117
<212> TYPE: PRT
<213> ORGANISM: Artificial Sequence
<220> FEATURE:
<223> OTHER INFORMATION: Synthetic

<400> SEQUENCE: 507

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Val Tyr Asn Gly Asn Thr Asn Tyr Ala Gln Lys Leu
     50                  55                  60
```

```
Gln Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Gly Ser Gly Tyr Asp Phe Asp Tyr Trp Gly Gln Gly Thr Leu
            100                 105                 110

Val Thr Val Ser Ser
            115

<210> SEQ ID NO 508
<211> LENGTH: 322
<212> TYPE: DNA
<213> ORGANISM: Artificial Sequence
<220> FEATURE:
<223> OTHER INFORMATION: Synthetic

<400> SEQUENCE: 508
gccatccaga tgacccagtc tccatcctcc ctgtctgcat ctgtaggaga cagagtcacc        60
atcacttgcc gggcaagtca gggcattaga aatgctttag ctggtatca gcagaaacca       120 gggaaagccc ctaagctcct gatctatgct gcatccagtt tacaaagtgg ggtcccatca      180
aggttcagcg gcagtggatc tggcacagat ttcactctca ccatcagcag cctgcagcct      240
gaagattttg caacttatta ctgtctacaa gattacaatt acccgtacac ttttggccag      300
gggaccaagc tggagatcaa ac                                               322

<210> SEQ ID NO 509
<211> LENGTH: 107
<212> TYPE: PRT
<213> ORGANISM: Artificial Sequence
<220> FEATURE:
<223> OTHER INFORMATION: Synthetic

<400> SEQUENCE: 509

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Ala
             20                  25                  30

Leu Gly Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Tyr
                 85                  90                  95

Thr Phe Gly Gln Gly Thr Lys Leu Glu Ile Lys
            100                 105

<210> SEQ ID NO 510
<211> LENGTH: 352
<212> TYPE: DNA
<213> ORGANISM: Artificial Sequence
<220> FEATURE:
<223> OTHER INFORMATION: Synthetic

<400> SEQUENCE: 510
caggttcagc tggtgcagtc tggagctgag gtgaagaagc ctggggcctc agtgaaggtc        60
tcctgcaagg cttctggtta cacctttacc agctatggta tcagctgggt gcgacaggcc      120
```

```
cctggacaag ggcttgagtg gatgggatgg atcagtgttt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagggagt    300
ggctacgatt ttgactactg gggccaagga accctggtca ccgtctcctc ag            352
```

<210> SEQ ID NO 511
<211> LENGTH: 117
<212> TYPE: PRT
<213> ORGANISM: Artificial Sequence
<220> FEATURE:
<223> OTHER INFORMATION: Synthetic

<400> SEQUENCE: 511

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Gly Tyr Asp Phe Asp Tyr Trp Gly Gln Gly Thr Leu
            100                 105                 110

Val Thr Val Ser Ser
        115
```

<210> SEQ ID NO 512
<211> LENGTH: 322
<212> TYPE: DNA
<213> ORGANISM: Artificial Sequence
<220> FEATURE:
<223> OTHER INFORMATION: Synthetic

<400> SEQUENCE: 512

```
gccatccaga tgacccagtc tccatcctcc ctgtctgcat ctgtaggaga cagagtcacc     60
atcacttgcc gggcaagtca gggcattaga aatgctttag ctggtatca gcagaaacca    120 gggaaagccc ctaagctcct gatctatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gattacaatt acccgtacac ttttggccag    300
gggaccaagc tggagatcaa ac                                             322
```

<210> SEQ ID NO 513
<211> LENGTH: 107
<212> TYPE: PRT
<213> ORGANISM: Artificial Sequence
<220> FEATURE:
<223> OTHER INFORMATION: Synthetic

<400> SEQUENCE: 513

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Ala
```

```
                20                  25                  30
Leu Gly Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Tyr
                 85                  90                  95

Thr Phe Gly Gln Gly Thr Lys Leu Glu Ile Lys
            100                 105
```

<210> SEQ ID NO 514
<211> LENGTH: 358
<212> TYPE: DNA
<213> ORGANISM: Artificial Sequence
<220> FEATURE:
<223> OTHER INFORMATION: Synthetic

<400> SEQUENCE: 514

```
caggtgcagc tggtggagtc tgggggaggc gtggtccagc ctggagggtc cctgagactc      60
tcctgtgcag cctctggatt caccttcaga agctatggca tgcactgggt ccgccaggct     120
ccaggcaagg ggctggagtg ggtggcagtt atatcatatg atggcagtaa aacatactat     180
gcagactccg tgaagggccg attcaccatc tccagagaca attccaagaa cacgctgtat     240
ctgcaaatga acagcctgag agctgaggac acggctgtgt attactgtgt gaaagaagga     300
agaagtggga gttggttcga ccccctgggc caaggaaccc tggtcaccgt ctcctcag      358
```

<210> SEQ ID NO 515
<211> LENGTH: 119
<212> TYPE: PRT
<213> ORGANISM: Artificial Sequence
<220> FEATURE:
<223> OTHER INFORMATION: Synthetic

<400> SEQUENCE: 515

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Lys Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Val Lys Glu Gly Arg Ser Gly Ser Trp Phe Asp Pro Trp Gly Gln Gly
            100                 105                 110

Thr Leu Val Thr Val Ser Ser
        115
```

<210> SEQ ID NO 516
<211> LENGTH: 322
<212> TYPE: DNA
<213> ORGANISM: Artificial Sequence
<220> FEATURE:

-continued

<223> OTHER INFORMATION: Synthetic

<400> SEQUENCE: 516

```
gacatccaga tgacccagtc tccatcctca ctgtctgcat ctgtaggaga cagagtcacc    60
atcacttgtc gggcgagtca ggccattaac aattttttag cctggtttca gcagaaacca   120
gggaaagccc ctaagtccct gatctatgct acatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtc acccgtggac gttcggccaa   300
gggaccaagg tggaaatcaa ac                                             322
```

<210> SEQ ID NO 517
<211> LENGTH: 107
<212> TYPE: PRT
<213> ORGANISM: Artificial Sequence
<220> FEATURE:
<223> OTHER INFORMATION: Synthetic

<400> SEQUENCE: 517

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn Phe
            20                  25                  30

Leu Ala Trp Phe Gln Gln Lys Pro Gly Lys Ala Pro Lys Ser Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys
            100                 105

<210> SEQ ID NO 518
<211> LENGTH: 358
<212> TYPE: DNA
<213> ORGANISM: Artificial Sequence
<220> FEATURE:
<223> OTHER INFORMATION: Synthetic

<400> SEQUENCE: 518

```
caggtgcagc tggtggagtc tgggggaggc gtggtccagc ctggagggtc cctgagactc    60
tcctgtgtag cctctggatt caccttcaga agctatggca tgcactgggt ccgccaggct   120
ccaggcaggg gactggagtg ggtggcagtt atatcatatg atggcagtaa acattctac    180
gtagattccg tgaaggtccg attcaccatc tccagagaca attccaagaa cacgctttat   240
ttggaaatga acagcctgag agttgacgac acggctgtgt atttctgtgt gaaagaagga   300
agaagtggga gttggttcga cccctggggc cagggaaccc tggtcgccgt ctcctcag    358
```

<210> SEQ ID NO 519
<211> LENGTH: 119
<212> TYPE: PRT
<213> ORGANISM: Artificial Sequence
<220> FEATURE:
<223> OTHER INFORMATION: Synthetic

<400> SEQUENCE: 519

```
Gln Val Gln Leu Val Glu Ser Gly Gly Gly Val Val Gln Pro Gly Gly
 1               5                  10                  15

Ser Leu Arg Leu Ser Cys Val Ala Ser Gly Phe Thr Phe Arg Ser Tyr
            20                  25                  30

Gly Met His Trp Val Arg Gln Ala Pro Gly Arg Gly Leu Glu Trp Val
         35                  40                  45

Ala Val Ile Ser Tyr Asp Gly Ser Lys Thr Phe Tyr Val Asp Ser Val
     50                  55                  60

Lys Val Arg Phe Thr Ile Ser Arg Asp Asn Ser Lys Asn Thr Leu Tyr
 65                  70                  75                  80

Leu Glu Met Asn Ser Leu Arg Val Asp Asp Thr Ala Val Tyr Phe Cys
                 85                  90                  95

Val Lys Glu Gly Arg Ser Gly Ser Trp Phe Asp Pro Trp Gly Gln Gly
            100                 105                 110

Thr Leu Val Ala Val Ser Ser
        115

<210> SEQ ID NO 520
<211> LENGTH: 322
<212> TYPE: DNA
<213> ORGANISM: Artificial Sequence
<220> FEATURE:
<223> OTHER INFORMATION: Synthetic

<400> SEQUENCE: 520
gacatccaga tgacccagtc tccatcctca ctgtctgcgt ctgtaggaga cagagtcacc      60
atcacttgtc gggcgagtca ggccattaac aattttttag cctggtttca gcagaaacca    120
gggaaaaccc ctaactccct gatctttgct acatccagtt acaaagtggg gtcccatca     180 aggttcagcg ccgtggatc  tgggacagac ttcactctca ccatcagcag cctgcagcct    240
gaagattttg caacttatta ctgccaacag tataatagtc accgtggac  gttcggccaa    300 gggaccaagg tggaaatcaa ac                                             322

<210> SEQ ID NO 521
<211> LENGTH: 107
<212> TYPE: PRT
<213> ORGANISM: Artificial Sequence
<220> FEATURE:
<223> OTHER INFORMATION: Synthetic

<400> SEQUENCE: 521

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Asn Asn Phe
            20                  25                  30

Leu Ala Trp Phe Gln Gln Lys Pro Gly Lys Thr Pro Asn Ser Leu Ile
         35                  40                  45

Phe Ala Thr Ser Ser Leu Gln Ser Gly Val Pro Ser Arg Phe Ser Ala
     50                  55                  60

Gly Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                 85                  90                  95

Thr Phe Gly Gln Gly Thr Lys Val Glu Ile Lys
            100                 105

<210> SEQ ID NO 522
```

<211> LENGTH: 358
<212> TYPE: DNA
<213> ORGANISM: Artificial Sequence
<220> FEATURE:
<223> OTHER INFORMATION: Synthetic

<400> SEQUENCE: 522

```
caggtgcagc tggtggagtc tgggggaggc gtggtccagc ctgggaggtc cctgagactc      60
tcctgtgcag cctctggatt catcttcaga agttatggca tgcactgggt ccgccaggct     120
ccaggcaagg ggctggagtg gtggcagtt atatcatatg atggcagtaa acatactat       180
gcagactccg tgaagggccg attcaccatc tccagagaca attccaagaa cacgctgtat    240
ctgcaaatga acagcctgag agctgaggac acggctgtgt attactgtgt gaaagaagga    300
agaagtggga gttggttcga ccctgggggc caaggaaccc tggtcaccgt ctcctcag      358
```

<210> SEQ ID NO 523
<211> LENGTH: 119
<212> TYPE: PRT
<213> ORGANISM: Artificial Sequence
<220> FEATURE:
<223> OTHER INFORMATION: Synthetic

<400> SEQUENCE: 523

```
Gln Val Gln Leu Val Glu Ser Gly Gly Gly Val Val Gln Pro Gly Arg
  1               5                  10                  15
Ser Leu Arg Leu Ser Cys Ala Ala Ser Gly Phe Ile Phe Arg Ser Tyr
             20                  25                  30
Gly Met His Trp Val Arg Gln Ala Pro Gly Lys Gly Leu Glu Trp Val
         35                  40                  45
Ala Val Ile Ser Tyr Asp Gly Ser Lys Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Val Lys Glu Gly Arg Ser Gly Ser Trp Phe Asp Pro Trp Gly Gln Gly
            100                 105                 110
Thr Leu Val Thr Val Ser Ser
        115
```

<210> SEQ ID NO 524
<211> LENGTH: 322
<212> TYPE: DNA
<213> ORGANISM: Artificial Sequence
<220> FEATURE:
<223> OTHER INFORMATION: Synthetic

<400> SEQUENCE: 524

```
gacatccaga tgacccagtc tccatcctca ctgtctgcat ctgtaggaga cagagtcacc     60
atcacttgtc gggcgagtca ggccattaac aatttttag cctggtttca gcagaaacca    120
gggaaagccc ctaagtccct gatctatgct acatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtc acccgtggac gttcggccaa    300
gggaccaagg tggaaatcaa ac                                            322
```

<210> SEQ ID NO 525
<211> LENGTH: 107

<212> TYPE: PRT
<213> ORGANISM: Artificial Sequence
<220> FEATURE:
<223> OTHER INFORMATION: Synthetic

<400> SEQUENCE: 525

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn Phe
            20                  25                  30

Leu Ala Trp Phe Gln Gln Lys Pro Gly Lys Ala Pro Lys Ser Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys
            100                 105

<210> SEQ ID NO 526
<211> LENGTH: 358
<212> TYPE: DNA
<213> ORGANISM: Artificial Sequence
<220> FEATURE:
<223> OTHER INFORMATION: Synthetic

<400> SEQUENCE: 526
caggtgcagc tggtggagtc tgggggaggc gtggtccagc ctggagggtc cctgagactc      60
tcctgtactg cctctggatt catcttcaga agttatggca tgcactgggt ccgccaggct     120
ccaggcaggg gactggagtg ggtggcagtc atatcatatg atggcagtaa aacattctac     180
gtagattccg tgaaggtccg attcaccatc tccagagaca actccaagaa cacgctttat     240
ttggagatga acagcctgag agttgacgac acggctgtat atttctgtgt gaaagaagga     300
agaagtggga gttggttcga ccctgggggc cagggaaccc tggtcaccgt ctcctcag      358

<210> SEQ ID NO 527
<211> LENGTH: 119
<212> TYPE: PRT
<213> ORGANISM: Artificial Sequence
<220> FEATURE:
<223> OTHER INFORMATION: Synthetic

<400> SEQUENCE: 527

Gln Val Gln Leu Val Glu Ser Gly Gly Gly Val Val Gln Pro Gly Gly
1               5                   10                  15

Ser Leu Arg Leu Ser Cys Thr Ala Ser Gly Phe Ile Phe Arg Ser Tyr
            20                  25                  30

Gly Met His Trp Val Arg Gln Ala Pro Gly Arg Gly Leu Glu Trp Val
        35                  40                  45

Ala Val Ile Ser Tyr Asp Gly Ser Lys Thr Phe Tyr Val Asp Ser Val
    50                  55                  60

Lys Val Arg Phe Thr Ile Ser Arg Asp Asn Ser Lys Asn Thr Leu Tyr
65                  70                  75                  80

Leu Glu Met Asn Ser Leu Arg Val Asp Asp Thr Ala Val Tyr Phe Cys
                85                  90                  95

Val Lys Glu Gly Arg Ser Gly Ser Trp Phe Asp Pro Trp Gly Gln Gly

<210> SEQ ID NO 528
<211> LENGTH: 322
<212> TYPE: DNA
<213> ORGANISM: Artificial Sequence
<220> FEATURE:
<223> OTHER INFORMATION: Synthetic

<400> SEQUENCE: 528

```
gacatccaga tgacccagtc tccatcctca ctgtctgcgt ctgtaggaga cagagtcacc      60
atcacttgtc gggcgagtca ggccattaac aatttttttag cctggtttca gcagaaacca     120
gggaaaaccc ctaagtccct gatctttgct acatccagtt tacaaagtgg ggtcccatca     180
aggttcagcg gcagtggatc tgggacagac ttcactctca ccatcagcag cctgcagcct     240
gaagattttg caacttatta ctgccaacag tataatagtc acccgtggac gttcggccaa     300
gggaccaagg tggaaatcaa ac                                              322
```

<210> SEQ ID NO 529
<211> LENGTH: 107
<212> TYPE: PRT
<213> ORGANISM: Artificial Sequence
<220> FEATURE:
<223> OTHER INFORMATION: Synthetic

<400> SEQUENCE: 529

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ala Ile Asn Asn Phe
            20                  25                  30
Leu Ala Trp Phe Gln Gln Lys Pro Gly Lys Thr Pro Lys Ser Leu Ile
        35                  40                  45
Phe Ala Thr Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser His Pro Trp
                85                  90                  95
Thr Phe Gly Gln Gly Thr Lys Val Glu Ile Lys
            100                 105

<210> SEQ ID NO 530
<211> LENGTH: 358
<212> TYPE: DNA
<213> ORGANISM: Artificial Sequence
<220> FEATURE:
<223> OTHER INFORMATION: Synthetic

<400> SEQUENCE: 530

```
caggtgcagc tggtggagtc tgggggaggc gtggtccagc ctgggaggtc cctgagactc      60
tcctgtgcag cctctggatt catcttcaga agctatggca tgcactgggt ccgccaggct     120
ccaggcaagg ggctggagtg ggtggcagtt atatcatatg atggcagtaa acatactat     180
gcagactccg tgaagggccg attcaccatc tccagagaca attccaagaa cacgctgtat     240
ctgcaaatga acagcctgag agctgaggac acggctgtgt attactgtgt gaaagaagga     300
agaagtggga gttggttcga cccctgggc caaggaaccc tggtcaccgt ctcctcag       358
```

<210> SEQ ID NO 531
<211> LENGTH: 119
<212> TYPE: PRT
<213> ORGANISM: Artificial Sequence
<220> FEATURE:
<223> OTHER INFORMATION: Synthetic

<400> SEQUENCE: 531

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Glu Gly Arg Ser Gly Ser Trp Phe Asp Pro Trp Gly Gln Gly
            100                 105                 110

Thr Leu Val Thr Val Ser Ser
        115

<210> SEQ ID NO 532
<211> LENGTH: 322
<212> TYPE: DNA
<213> ORGANISM: Artificial Sequence
<220> FEATURE:
<223> OTHER INFORMATION: Synthetic

<400> SEQUENCE: 532
gacatccaga tgacccagtc tccatcctca ctgtctgcat ctgtaggaga cagagtcacc      60
atcacttgtc gggcgagtca ggccattaac aattttttag cctggtttca gcagaaacca    120
gggaaagccc ctaagtccct gatctatgct acatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtc acccgtggac gttcggccaa    300
gggaccaagg tggaaatcaa ac                                             322

<210> SEQ ID NO 533
<211> LENGTH: 107
<212> TYPE: PRT
<213> ORGANISM: Artificial Sequence
<220> FEATURE:
<223> OTHER INFORMATION: Synthetic

<400> SEQUENCE: 533

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn Phe
            20                  25                  30

Leu Ala Trp Phe Gln Gln Lys Pro Gly Lys Ala Pro Lys Ser Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys
            100                 105

<210> SEQ ID NO 534
<211> LENGTH: 358
<212> TYPE: DNA
<213> ORGANISM: Artificial Sequence
<220> FEATURE:
<223> OTHER INFORMATION: Synthetic

<400> SEQUENCE: 534
caggtgcagc tggtggagtc tgggggaggc gtggtccagc ctggagggtc cctgagactc    60
tcctgtgctg cctctggatt catcttcaga agctatggca tgcactgggt ccgccaggct   120
ccaggcaggg gactggagtg ggtggcagtc atatcatatg atggcagtaa aacattctac   180
gtagattccg tgaaggtccg attcaccata tccagagaca actccaagaa cacgctttat   240
ttggaaatga acagcctgag agttgacgac acggctgtat atttctgtgt gaaagaagga   300
agaagtggga gttggttcga ccccgggggc cagggaaccc tggtcaccgt ctcctcag    358

<210> SEQ ID NO 535
<211> LENGTH: 119
<212> TYPE: PRT
<213> ORGANISM: Artificial Sequence
<220> FEATURE:
<223> OTHER INFORMATION: Synthetic

<400> SEQUENCE: 535

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Phe Arg Ser Tyr
            20                  25                  30

Gly Met His Trp Val Arg Gln Ala Pro Gly Arg Gly Leu Glu Trp Val
        35                  40                  45

Ala Val Ile Ser Tyr Asp Gly Ser Lys Thr Phe Tyr Val Asp Ser Val
    50                  55                  60

Lys Val Arg Phe Thr Ile Ser Arg Asp Asn Ser Lys Asn Thr Leu Tyr
65                  70                  75                  80

Leu Glu Met Asn Ser Leu Arg Val Asp Asp Thr Ala Val Tyr Phe Cys
                85                  90                  95

Val Lys Glu Gly Arg Ser Gly Ser Trp Phe Asp Pro Trp Gly Gln Gly
            100                 105                 110

Thr Leu Val Thr Val Ser Ser
        115

<210> SEQ ID NO 536
<211> LENGTH: 322
<212> TYPE: DNA
<213> ORGANISM: Artificial Sequence
<220> FEATURE:
<223> OTHER INFORMATION: Synthetic

<400> SEQUENCE: 536
gacatccaga tgacccagtc tccatcctca ctgtctgcgt ctgtaggaga cagagtcacc    60
atcacttgtc gggcgagtca ggccattaac aattttttag cctggtttca gcagaaacca   120

```
gggaaaaccc ctaagtccct gatctttgct acatccagtt tacaaagtgg ggtcccatca      180
aggttcagcg gcagtggatc tgggacagac ttcactctca ccatcagcag cctgcagcct      240
gaagattttg caacttatta ctgccaacag tataatagtc acccgtggac gttcggccaa      300
gggaccaagg tggaaatcaa ac                                               322
```

<210> SEQ ID NO 537
<211> LENGTH: 107
<212> TYPE: PRT
<213> ORGANISM: Artificial Sequence
<220> FEATURE:
<223> OTHER INFORMATION: Synthetic

<400> SEQUENCE: 537

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ala Ile Asn Asn Phe
             20                  25                  30

Leu Ala Trp Phe Gln Gln Lys Pro Gly Lys Thr Pro Lys Ser Leu Ile
         35                  40                  45

Phe Ala Thr Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                 85                  90                  95

Thr Phe Gly Gln Gly Thr Lys Val Glu Ile Lys
            100                 105
```

<210> SEQ ID NO 538
<211> LENGTH: 355
<212> TYPE: DNA
<213> ORGANISM: Artificial Sequence
<220> FEATURE:
<223> OTHER INFORMATION: Synthetic

<400> SEQUENCE: 538

```
caggtgcagc tggtggagtc tgggggaggc gtggtccagc ctggggaggtc cctgagactc      60 tcctgtgcag cctctggatt caccttcagt agctatggca tgcactgggt ccgccaggct     120
ccaggcaagg ggctggagtg ggtggcagtt atatcatatg atggaagtat taaatactat     180
gcagactccg tgaagggccg attcaccatc tccagagaca attccaagaa cacgctgtat     240
ctgcaaatga acagcctgag agctgaggac acggctgtgt attactgtgc gaaggaaggt     300
aggaagtacg gtatggacgt ctggggggcaa gggaccacgg tcaccgtctc ctcag         355
```

<210> SEQ ID NO 539
<211> LENGTH: 118
<212> TYPE: PRT
<213> ORGANISM: Artificial Sequence
<220> FEATURE:
<223> OTHER INFORMATION: Synthetic

<400> SEQUENCE: 539

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45
```

```
Ala Val Ile Ser Tyr Asp Gly Ser Ile Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Arg Lys Tyr Gly Met Asp Val Trp Gly Gln Gly Thr
            100                 105                 110

Thr Val Thr Val Ser Ser
        115

<210> SEQ ID NO 540
<211> LENGTH: 322
<212> TYPE: DNA
<213> ORGANISM: Artificial Sequence
<220> FEATURE:
<223> OTHER INFORMATION: Synthetic

<400> SEQUENCE: 540
gacatccaga tgacccagtc tccttccacc ctgtctgcat ctgtaggaga cagagtcacc      60
atcacttgcc gggccagtca gattattagt agcttattgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tatcatagtt acatgtacac ttttggccag    300
gggaccaagc tggagatcaa ac                                             322

<210> SEQ ID NO 541
<211> LENGTH: 107
<212> TYPE: PRT
<213> ORGANISM: Artificial Sequence
<220> FEATURE:
<223> OTHER INFORMATION: Synthetic

<400> SEQUENCE: 541

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ile Ile Ser Ser Leu
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr His Ser Tyr Met Tyr
                 85                  90                  95

Thr Phe Gly Gln Gly Thr Lys Leu Glu Ile Lys
            100                 105

<210> SEQ ID NO 542
<211> LENGTH: 355
<212> TYPE: DNA
<213> ORGANISM: Artificial Sequence
<220> FEATURE:
<223> OTHER INFORMATION: Synthetic

<400> SEQUENCE: 542
```

```
caggtgcagc tggtggagtc tgggggaggc gtggtccagc ctggagagtc cctgagactc    60
tcctgtgcag cctctggatt caccttcagt agctatggca tgcactgggt ccgccaggct   120
ccaggcaagg ggctggagtg ggtggcagtt atatcatatg atggaagtat taaatactat   180
gcagactccg tgaagggccg attcaccatc tccagagaca attccaagaa cacgctgtat   240
ctgcaaatga acagcctgag agctgaggac acggctgtgt attactgtgc gaaggaaggt   300
aggaagtacg gtatggacgt ctgggggcaa gggaccacgg tcaccgtctc ctcag        355
```

<210> SEQ ID NO 543
<211> LENGTH: 118
<212> TYPE: PRT
<213> ORGANISM: Artificial Sequence
<220> FEATURE:
<223> OTHER INFORMATION: Synthetic

<400> SEQUENCE: 543

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Ile Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Arg Lys Tyr Gly Met Asp Val Trp Gly Gln Gly Thr
            100                 105                 110

Thr Val Thr Val Ser Ser
        115
```

<210> SEQ ID NO 544
<211> LENGTH: 322
<212> TYPE: DNA
<213> ORGANISM: Artificial Sequence
<220> FEATURE:
<223> OTHER INFORMATION: Synthetic

<400> SEQUENCE: 544

```
gacatccaga tgacccagtc tccttccacc ctgtctgcat ctgtaggaga cagagtcacc    60
atcacttgcc gggccagtca gattattagt agcttattgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatcatagtt acatgtacac ttttggccag   300
gggaccaagc tggagatcaa ac                                            322
```

<210> SEQ ID NO 545
<211> LENGTH: 107
<212> TYPE: PRT
<213> ORGANISM: Artificial Sequence
<220> FEATURE:
<223> OTHER INFORMATION: Synthetic

<400> SEQUENCE: 545

```
Asp Ile Gln Met Thr Gln Ser Pro Ser Thr Leu Ser Ala Ser Val Gly
```

```
                1               5              10              15
Asp Arg Val Thr Ile Thr Cys Arg Ala Ser Gln Ile Ile Ser Ser Leu
                               20                  25                  30

Leu Ala Trp Tyr Gln Gln Lys Pro Gly Lys Ala Pro Lys Leu Leu Ile
                35                  40                  45

Tyr Lys Ala Ser Ser Leu Glu Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr His Ser Tyr Met Tyr
                    85                  90                  95

Thr Phe Gly Gln Gly Thr Lys Leu Glu Ile Lys
                100                 105
```

<210> SEQ ID NO 546
<211> LENGTH: 358
<212> TYPE: DNA
<213> ORGANISM: Artificial Sequence
<220> FEATURE:
<223> OTHER INFORMATION: Synthetic

<400> SEQUENCE: 546

```
caggtgcagc tggtggagtc tgggggaggc gtggtccagc ctggggaggtc cctgagactc     60
tcctgtgcag cctctggatt caccttcagt agctttggca tgcactgggt ccgccaggct    120
ccaggcaagg gctggagtg gtggcagtt atatcatatg atggcagtaa aaaatactat    180
gcagactccg tgaagggccg attcaccatc tccagagaca attccaagaa cacgctgtat    240
ctgcaaatga acagcctgag agctgaggac acggctgtgt attactgtgc gaaagaagga    300
agaactggga attggttcga cccctggggc caaggaaccc tggtcaccgt ctcctcag     358
```

<210> SEQ ID NO 547
<211> LENGTH: 119
<212> TYPE: PRT
<213> ORGANISM: Artificial Sequence
<220> FEATURE:
<223> OTHER INFORMATION: Synthetic

<400> SEQUENCE: 547

```
Gln Val Gln Leu Val Glu Ser Gly Gly Gly Val Gln Pro Gly Arg
  1               5                  10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Val Ile Ser Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Glu Gly Arg Thr Gly Asn Trp Phe Asp Pro Trp Gly Gln Gly
                100                 105                 110

Thr Leu Val Thr Val Ser Ser
            115
```

<210> SEQ ID NO 548
<211> LENGTH: 322

<212> TYPE: DNA
<213> ORGANISM: Artificial Sequence
<220> FEATURE:
<223> OTHER INFORMATION: Synthetic

<400> SEQUENCE: 548

```
gacatccaga tgacccagtc tccatcctca ctgtctgcat ctgtaggaga cagagtcacc      60
atcacttgtc gggcgagtca ggccattaac aattatttag cctggtttca gcagaaacca     120
gggaaagccc ctaagtccct gatctatgct acatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtc acccgtggac gttcggccaa     300
gggaccaagg tggaaatcaa ac                                              322
```

<210> SEQ ID NO 549
<211> LENGTH: 107
<212> TYPE: PRT
<213> ORGANISM: Artificial Sequence
<220> FEATURE:
<223> OTHER INFORMATION: Synthetic

<400> SEQUENCE: 549

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ala Ile Asn Asn Tyr
            20                  25                  30
Leu Ala Trp Phe Gln Gln Lys Pro Gly Lys Ala Pro Lys Ser Leu Ile
        35                  40                  45
Tyr Ala Thr Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser His Pro Trp
                85                  90                  95
Thr Phe Gly Gln Gly Thr Lys Val Glu Ile Lys
            100                 105

<210> SEQ ID NO 550
<211> LENGTH: 358
<212> TYPE: DNA
<213> ORGANISM: Artificial Sequence
<220> FEATURE:
<223> OTHER INFORMATION: Synthetic

<400> SEQUENCE: 550

```
caggtgcagc tggtggagtc tgggggaggc gtggtccagc ctggagggtc cctgagactc      60
tcctgtacag cctctggatt caccttcagt agctttggca tgcactgggt ccgccaggct     120
ccaggcaggg gactggagtg ggtggcagtt atatcatatg atggcagtaa aaatactac     180
gcagactccg tgaaggtccg attcaccatc tccagagaca actccaagaa cacgctttat     240
ctgcaaatga acagcctgag agttgacgac acggctgtgt atttctgtgc gaaagaagga     300
agaactggga attggttcga cccctggggc cagggaaccc tggtcaccgt ctcctcag      358
```

<210> SEQ ID NO 551
<211> LENGTH: 119
<212> TYPE: PRT
<213> ORGANISM: Artificial Sequence
<220> FEATURE:
<223> OTHER INFORMATION: Synthetic

<400> SEQUENCE: 551

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Phe
            20                  25                  30

Gly Met His Trp Val Arg Gln Ala Pro Gly Arg Gly Leu Glu Trp Val
        35                  40                  45

Ala Val Ile Ser Tyr Asp Gly Ser Lys Lys Tyr Tyr Ala Asp Ser Val
    50                  55                  60

Lys Val Arg Phe Thr Ile Ser Arg Asp Asn Ser Lys Asn Thr Leu Tyr
65                  70                  75                  80

Leu Gln Met Asn Ser Leu Arg Val Asp Asp Thr Ala Val Tyr Phe Cys
                85                  90                  95

Ala Lys Glu Gly Arg Thr Gly Asn Trp Phe Asp Pro Trp Gly Gln Gly
            100                 105                 110

Thr Leu Val Thr Val Ser Ser
            115

<210> SEQ ID NO 552
<211> LENGTH: 322
<212> TYPE: DNA
<213> ORGANISM: Artificial Sequence
<220> FEATURE:
<223> OTHER INFORMATION: Synthetic

<400> SEQUENCE: 552
gacatccaga tgacccagtc tccatcctca ctgtctgcat ctgtaggaga cagagtcacc    60
atcacttgtc gggcgagtca ggccattaac aattatttag cctggtttca gcagaaacca   120
gggaaaaccc ctaagtccct gatctttgct acatccagtt tacaaagtgg ggtcccatca   180
aggttcagcg gcactggatc tgggacagac ttcactctca ccatcagcag cctgcagcct   240
gaagattttg caacttatta ctgccaacag tataatagtc acccgtggac gttcggccaa   300
gggaccaagg tggaaatcaa ac                                            322

<210> SEQ ID NO 553
<211> LENGTH: 107
<212> TYPE: PRT
<213> ORGANISM: Artificial Sequence
<220> FEATURE:
<223> OTHER INFORMATION: Synthetic

<400> SEQUENCE: 553

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn Tyr
            20                  25                  30

Leu Ala Trp Phe Gln Gln Lys Pro Gly Lys Thr Pro Lys Ser Leu Ile
        35                  40                  45

Phe Ala Thr Ser Ser Leu Gln Ser Gly Val Pro Ser Arg Phe Ser Gly
    50                  55                  60

Thr Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys
            100                 105

<210> SEQ ID NO 554
<211> LENGTH: 358
<212> TYPE: DNA
<213> ORGANISM: Artificial Sequence
<220> FEATURE:
<223> OTHER INFORMATION: Synthetic

<400> SEQUENCE: 554

```
caggtgcagc tggtggagtc tgggggaggc gtggtccagc ctggagggtc cctgagactc      60
tcctgtgcag cctctggatt caccttcaga agttatggca tgcactgggt ccgccaggct     120
ccaggcaagg ggctggagtg ggtggcagtt atatcatatg atggcagtca aacatactat     180
gcagactccg tgaagggccg attcaccatc tccagagaca attccaagaa cacgctgtat     240
ctgcaaatga acagcctgag agctgaggac acggctgtgt attactgtgt gaaagaagga     300
agaagtggga gttggttcga cccctggggc caaggaaccc tggtcaccgt ctcctcag      358
```

<210> SEQ ID NO 555
<211> LENGTH: 119
<212> TYPE: PRT
<213> ORGANISM: Artificial Sequence
<220> FEATURE:
<223> OTHER INFORMATION: Synthetic

<400> SEQUENCE: 555

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Arg Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Gln Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Lys Glu Gly Arg Ser Gly Ser Trp Phe Asp Pro Trp Gly Gln Gly
            100                 105                 110

Thr Leu Val Thr Val Ser Ser
        115
```

<210> SEQ ID NO 556
<211> LENGTH: 322
<212> TYPE: DNA
<213> ORGANISM: Artificial Sequence
<220> FEATURE:
<223> OTHER INFORMATION: Synthetic

<400> SEQUENCE: 556

```
gacatccaga tgacccagtc tccatcctca ctgtctgcat ctgtaggaga cagagtcacc      60
atcacttgtc gggcgagtca ggccattaat aattatttag cctggtttca gcagaaacca     120
gggaaagccc ctaagtccct gatctatgct catccagtt tgcaaagtgg ggtcccatca     180
aggttcagcg gcagtggatc tgggacagat ttcactctca ccatcagcag cctgcagcct     240
gaagattttg caacttatta ctgccaacag tataatagtc cccgtggac gttcggccaa     300 gggaccaagg tggaaatcaa ac                                              322
```

```
<210> SEQ ID NO 557
<211> LENGTH: 107
<212> TYPE: PRT
<213> ORGANISM: Artificial Sequence
<220> FEATURE:
<223> OTHER INFORMATION: Synthetic

<400> SEQUENCE: 557
```

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Asn Asn Tyr
             20                  25                  30

Leu Ala Trp Phe Gln Gln Lys Pro Gly Lys Ala Pro Lys Ser Leu Ile
         35                  40                  45

Tyr Ala Thr Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                 85                  90                  95

Thr Phe Gly Gln Gly Thr Lys Val Glu Ile Lys
            100                 105

```
<210> SEQ ID NO 558
<211> LENGTH: 358
<212> TYPE: DNA
<213> ORGANISM: Artificial Sequence
<220> FEATURE:
<223> OTHER INFORMATION: Synthetic

<400> SEQUENCE: 558
caggtgcagc tggtggagtc tgggggaggc gtggtccagc ctggaaggtc cctgagactc      60
tcctgtgtag cctctggatt caccttcaga agttatggca tgcactgggt ccgccaggct     120
ccaggcaggg gactggagtg ggtggcagtc atatcatatg atggcagtca acattctat      180 gtagattccg tgaaggtccg attcaccatc tccagagaca actccaacaa cacgctttat     240
ttggaaatga acagcctgag agttgacgac acggctgttt atttctgtgt gaaagaagga     300
agaagtggga gttggttcga cccctggggc cagggaaccc tggtcaccgt ctcctcag      358

<210> SEQ ID NO 559
<211> LENGTH: 119
<212> TYPE: PRT
<213> ORGANISM: Artificial Sequence
<220> FEATURE:
<223> OTHER INFORMATION: Synthetic

<400> SEQUENCE: 559
```

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Arg Ser Tyr
             20                  25                  30

Gly Met His Trp Val Arg Gln Ala Pro Gly Arg Gly Leu Glu Trp Val
         35                  40                  45

Ala Val Ile Ser Tyr Asp Gly Ser Gln Thr Phe Tyr Val Asp Ser Val
     50                  55                  60

Lys Val Arg Phe Thr Ile Ser Arg Asp Asn Ser Asn Asn Thr Leu Tyr
 65                  70                  75                  80

Leu Glu Met Asn Ser Leu Arg Val Asp Asp Thr Ala Val Tyr Phe Cys 85                  90                  95
Val Lys Glu Gly Arg Ser Gly Ser Trp Phe Asp Pro Trp Gly Gln Gly
            100                 105                 110

Thr Leu Val Thr Val Ser Ser
        115

<210> SEQ ID NO 560
<211> LENGTH: 322
<212> TYPE: DNA
<213> ORGANISM: Artificial Sequence
<220> FEATURE:
<223> OTHER INFORMATION: Synthetic

<400> SEQUENCE: 560
gacatccaga tgacccagtc tccatcctca ctgtctgcgt ctgttggaga cagagtcacc    60
atcacttgtc gggcgagtca ggccattaat aattatttag cctggtttca gcagaaacca   120
gggagaaccc ctaagtccct gatctttgct acatccagtt tacaaagtgg ggtcccatca   180
aggttcagcg gcagtggatc tgggacagac ttcactctca ccatcagcag cctgcagcct   240
gaagattttg caacttatta ctgccaacag tataatagtc acccgtggac gttcggccaa   300
gggaccaagg tggaaatcaa ac                                            322

<210> SEQ ID NO 561
<211> LENGTH: 107
<212> TYPE: PRT
<213> ORGANISM: Artificial Sequence
<220> FEATURE:
<223> OTHER INFORMATION: Synthetic

<400> SEQUENCE: 561

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ala Ile Asn Asn Tyr
             20                  25                  30

Leu Ala Trp Phe Gln Gln Lys Pro Gly Arg Thr Pro Lys Ser Leu Ile
         35                  40                  45

Phe Ala Thr Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                 85                  90                  95

Thr Phe Gly Gln Gly Thr Lys Val Glu Ile Lys
            100                 105

<210> SEQ ID NO 562
<211> LENGTH: 355
<212> TYPE: DNA
<213> ORGANISM: Artificial Sequence
<220> FEATURE:
<223> OTHER INFORMATION: Synthetic

<400> SEQUENCE: 562
caggtgcagc tggtggagtc tgggggaggc gtggtccagc ctgggaggtc cctgagactc    60
tcctgtgcag cctctggatt caccttcagt agttatgcca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240

```
ctgcaaatga acagcctgag agctgaggac acggctgtgt attactgtgc gaaagaaagt    300
tcttcgtacg gtttggacgt ctgggggcaa gggaccacgg tcaccgtctc ctcag         355
```

<210> SEQ ID NO 563
<211> LENGTH: 118
<212> TYPE: PRT
<213> ORGANISM: Artificial Sequence
<220> FEATURE:
<223> OTHER INFORMATION: Synthetic

<400> SEQUENCE: 563

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Ser Ser Ser Tyr Gly Leu Asp Val Trp Gly Gln Gly Thr
            100                 105                 110

Thr Val Thr Val Ser Ser
        115
```

<210> SEQ ID NO 564
<211> LENGTH: 322
<212> TYPE: DNA
<213> ORGANISM: Artificial Sequence
<220> FEATURE:
<223> OTHER INFORMATION: Synthetic

<400> SEQUENCE: 564

```
gacatccaga tgacccagtc tccttccacc ctgtctgcat ctgtaggaga cagagtcacc    60
atcacttgcc gggccagtca gagtattagt aactggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attcgtacac ttttggccag   300
gggaccaagc tggagatcaa ac                                             322
```

<210> SEQ ID NO 565
<211> LENGTH: 107
<212> TYPE: PRT
<213> ORGANISM: Artificial Sequence
<220> FEATURE:
<223> OTHER INFORMATION: Synthetic

<400> SEQUENCE: 565

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Asn Trp
             20                  25                  30

Leu Ala Trp Tyr Gln Gln Lys Pro Gly Lys Ala Pro Lys Leu Leu Ile
         35                  40                  45
```

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105

<210> SEQ ID NO 566
<211> LENGTH: 355
<212> TYPE: DNA
<213> ORGANISM: Artificial Sequence
<220> FEATURE:
<223> OTHER INFORMATION: Synthetic

<400> SEQUENCE: 566
caggtgcagc tggtggagtc tgggggaggc gtggtccagc ctgggaggtc cctgagactc      60
tcctgtgcag cctctggatt caccttcagt agttatgcca tgtactgggt ccgccaggct     120
ccaggcaagg ggctggagtg ggtggcagtg atatcatatg atggaagtaa taaatactat     180
acagactccg tgaagggccg attcaccgtc tccagagaca attccaaaaa cacgctgttt     240
ctgcaaatga acagcctgag agctgaggac acggctctgt attactgtgc gaaagaaagt     300
tcttcgtacg gtttggacgt ctggggtcaa gggaccacgg tcaccgtctc ctcag          355

<210> SEQ ID NO 567
<211> LENGTH: 118
<212> TYPE: PRT
<213> ORGANISM: Artificial Sequence
<220> FEATURE:
<223> OTHER INFORMATION: Synthetic

<400> SEQUENCE: 567

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ala Val Ile Ser Tyr Asp Gly Ser Asn Lys Tyr Tyr Thr Asp Ser Val
    50                  55                  60

Lys Gly Arg Phe Thr Val Ser Arg Asp Asn Ser Lys Asn Thr Leu Phe
65                  70                  75                  80

Leu Gln Met Asn Ser Leu Arg Ala Glu Asp Thr Ala Leu Tyr Tyr Cys
                85                  90                  95

Ala Lys Glu Ser Ser Ser Tyr Gly Leu Asp Val Trp Gly Gln Gly Thr
            100                 105                 110

Thr Val Thr Val Ser Ser
        115

<210> SEQ ID NO 568
<211> LENGTH: 322
<212> TYPE: DNA
<213> ORGANISM: Artificial Sequence
<220> FEATURE:
<223> OTHER INFORMATION: Synthetic

<400> SEQUENCE: 568
gacatccaga tgacccagtc tccttccacc ctgtctgcat ctgtaggaga cagagtcgcc      60

```
atcacttgcc gggccagtca gagtattagt aactggttgg cctggtatca gcagaaacca      120
gggaaagccc ctaaactcct gatctctaag gcgtctagtt taaaaagtgg ggtcccatca      180
aggttcagcg gcagtggatc tgggacagaa ttcactctca ccatcagcag cctgcagcct      240
gatgattttg cagcttatta ctgccaacag tataatagtt attcgtacac ttttggccag      300
gggaccaagc tggagatcaa ac                                               322
```

<210> SEQ ID NO 569
<211> LENGTH: 107
<212> TYPE: PRT
<213> ORGANISM: Artificial Sequence
<220> FEATURE:
<223> OTHER INFORMATION: Synthetic

<400> SEQUENCE: 569

```
Asp Ile Gln Met Thr Gln Ser Pro Ser Thr Leu Ser Ala Ser Val Gly
1               5                   10                  15

Asp Arg Val Ala Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Ser Lys Ala Ser Ser Leu Lys Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Ala Tyr Tyr Cys Gln Gln Tyr Asn Ser Tyr Ser Tyr
                85                  90                  95

Thr Phe Gly Gln Gly Thr Lys Leu Glu Ile Lys
            100                 105
```

<210> SEQ ID NO 570
<211> LENGTH: 358
<212> TYPE: DNA
<213> ORGANISM: Artificial Sequence
<220> FEATURE:
<223> OTHER INFORMATION: Synthetic

<400> SEQUENCE: 570

```
caggtgcagc tggtggagtc tgggggaggc gtggtccagc ctggggaggtc cctgagactc      60 tcctgtgcag cctctggatt caccttcagt agctatggca tgcactgggt ccgccaggct     120
ccaggcaagg ggctggagtg ggtggcagtt ttatcatatg atggcagtaa agaatactat     180
gcagactccg tgaagggccg attcaccatc tccagagaca attccaagaa cacgctgtat     240
ctgcaaatga acagcctgag agctgaggac acggctgtgt attactgtgc gaaagaagga     300
agaactggga attggttcga cccctggggc caaggaaccc tggtcaccgt ctcctcag      358
```

<210> SEQ ID NO 571
<211> LENGTH: 119
<212> TYPE: PRT
<213> ORGANISM: Artificial Sequence
<220> FEATURE:
<223> OTHER INFORMATION: Synthetic

<400> SEQUENCE: 571

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

Gly Met His Trp Val Arg Gln Ala Pro Gly Lys Gly Leu Glu Trp Val
            35                  40                  45

Ala Val Leu Ser Tyr Asp Gly Ser Lys Glu Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Arg Thr Gly Asn Trp Phe Asp Pro Trp Gly Gln Gly
             100                 105                 110

Thr Leu Val Thr Val Ser Ser
            115

<210> SEQ ID NO 572
<211> LENGTH: 322
<212> TYPE: DNA
<213> ORGANISM: Artificial Sequence
<220> FEATURE:
<223> OTHER INFORMATION: Synthetic

<400> SEQUENCE: 572
gacatccaga tgacccagtc tccatcctca ctgtctgcat ctgtaggaga cagagtcacc      60
atcacttgtc gggcgagtca ggccattaac aattttttag cctggtttca gcagaaacca     120
gggaaagccc ctaagtccct gatctatgct acatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtc acccgtggac gttcggccaa     300
gggaccaagg tggaaatcaa ac                                             322

<210> SEQ ID NO 573
<211> LENGTH: 107
<212> TYPE: PRT
<213> ORGANISM: Artificial Sequence
<220> FEATURE:
<223> OTHER INFORMATION: Synthetic

<400> SEQUENCE: 573

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ala Ile Asn Asn Phe
             20                  25                  30

Leu Ala Trp Phe Gln Gln Lys Pro Gly Lys Ala Pro Lys Ser Leu Ile
         35                  40                  45

Tyr Ala Thr Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                 85                  90                  95

Thr Phe Gly Gln Gly Thr Lys Val Glu Ile Lys
            100                 105

<210> SEQ ID NO 574
<211> LENGTH: 358
<212> TYPE: DNA
<213> ORGANISM: Artificial Sequence
<220> FEATURE:
<223> OTHER INFORMATION: Synthetic

<400> SEQUENCE: 574

```
caggtgcagc tggtggagtc tgggggaggc gtggtccagc ctggggggtc cctgagactc    60
tcctgtgcag cctctggatt caccttcagt agctatggca tgcactgggt ccgccaggct   120
ccaggcaggg gactggagtg gtggcagtt ttatcatatg atggcagtaa agaattctac   180
gcagactccg tgaaggtccg attcaccgtc tccagagaca actccaagaa cacgctttat   240
ctgcaaatga gcagcctgag agttgaggac acggctatat atttctgtgc gaaagaagga   300
agaactggga attggttcga ccctggggc cagggaaccc tggtcaccgt ctcctcag     358
```

<210> SEQ ID NO 575
<211> LENGTH: 119
<212> TYPE: PRT
<213> ORGANISM: Artificial Sequence
<220> FEATURE:
<223> OTHER INFORMATION: Synthetic

<400> SEQUENCE: 575

```
Gln Val Gln Leu Val Glu Ser Gly Gly Gly Val Val Gln Pro Gly Gly
  1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Arg Gly Leu Glu Trp Val
         35                  40                  45
Ala Val Leu Ser Tyr Asp Gly Ser Lys Glu Phe Tyr Ala Asp Ser Val
     50                  55                  60
Lys Val Arg Phe Thr Val Ser Arg Asp Asn Ser Lys Asn Thr Leu Tyr
 65                  70                  75                  80
Leu Gln Met Ser Ser Leu Arg Val Glu Asp Thr Ala Ile Tyr Phe Cys
                 85                  90                  95
Ala Lys Glu Gly Arg Thr Gly Asn Trp Phe Asp Pro Trp Gly Gln Gly
            100                 105                 110
Thr Leu Val Thr Val Ser Ser
        115
```

<210> SEQ ID NO 576
<211> LENGTH: 322
<212> TYPE: DNA
<213> ORGANISM: Artificial Sequence
<220> FEATURE:
<223> OTHER INFORMATION: Synthetic

<400> SEQUENCE: 576

```
gacatccaga tgacccagtc tccatcctca ctgtctgcat ctgtaggaga cagagtcacc    60
atcacttgtc gggcgagtca ggccattaac aattttttag cctggtttca gcagaaacca   120
gggaaagccc ctaagtccct gatctatgct acatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtc cccgtggac gttcggccaa   300
gggaccaagg tggaaatcaa ac                                             322
```

<210> SEQ ID NO 577
<211> LENGTH: 107
<212> TYPE: PRT
<213> ORGANISM: Artificial Sequence
<220> FEATURE:
<223> OTHER INFORMATION: Synthetic

<400> SEQUENCE: 577

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Asn Asn Phe
             20                  25                  30

Leu Ala Trp Phe Gln Gln Lys Pro Gly Lys Ala Pro Lys Ser Leu Ile
         35                  40                  45

Tyr Ala Thr Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
             85                  90                  95

Thr Phe Gly Gln Gly Thr Lys Val Glu Ile Lys
            100                 105

<210> SEQ ID NO 578
<211> LENGTH: 355
<212> TYPE: DNA
<213> ORGANISM: Artificial Sequence
<220> FEATURE:
<223> OTHER INFORMATION: Synthetic

<400> SEQUENCE: 578
gaagtgcacc tggtggaatc tgggggaggc ttggtacagc ctggcaggtc cctgagactc      60
tcctgtgagg cctctggatt cacctttgat gattatgcca tgcactgggt ccggcaagct     120
ccggggaagg gcctggaatg ggtctcaggt cttagtcgga caagtgtcag tataggctat     180
gcggactctg tgaagggccg attcaccatc tccagagaca cgccaagaa ctcccttttat     240 ttggaaatga acagtctgag acctgaggac acggccttat attactgtgc aaaatggggg     300 acccggggt attttgacta ctggggccag ggaaccctgg tcaccgtctc ctcag          355

<210> SEQ ID NO 579
<211> LENGTH: 118
<212> TYPE: PRT
<213> ORGANISM: Artificial Sequence
<220> FEATURE:
<223> OTHER INFORMATION: Synthetic

<400> SEQUENCE: 579

Glu Val His Leu Val Glu Ser Gly Gly Gly Leu Val Gln Pro Gly Arg
 1               5                  10                  15

Ser Leu Arg Leu Ser Cys Glu Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Leu Ser Arg Thr Ser Val Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Glu Met Asn Ser Leu Arg Pro Glu Asp Thr Ala Leu Tyr Tyr Cys
             85                  90                  95

Ala Lys Trp Gly Thr Arg Gly Tyr Phe Asp Tyr Trp Gly Gln Gly Thr
            100                 105                 110

Leu Val Thr Val Ser Ser
            115

<210> SEQ ID NO 580
<211> LENGTH: 355
<212> TYPE: DNA
<213> ORGANISM: Artificial Sequence
<220> FEATURE:
<223> OTHER INFORMATION: Synthetic

<400> SEQUENCE: 580

```
gaagtgcagc tggtggagtc tgggggaggc ttggtacagc ctggcaggtc cctgagactc      60
tcctgtgagg cctctggatt cacctttgat gattatgcca tgcactgggt ccggcaagct     120
ccggggaagg gcctggaatg ggtctcaggt cttagtcgaa caagtgtcag tataggctat     180
gcggactctg tgaagggccg attcaccatc tccagagaca acgccaagaa ctcccttat     240 ttggaaatga acagtctgag acctgaggac acggccttat attactgtgc aaaatggggg     300 acccggggt attttgacta ctggggccag ggaaccctgg tcaccgtctc ctcag           355
```

<210> SEQ ID NO 581
<211> LENGTH: 118
<212> TYPE: PRT
<213> ORGANISM: Artificial Sequence
<220> FEATURE:
<223> OTHER INFORMATION: Synthetic

<400> SEQUENCE: 581

```
Glu Val Gln Leu Val Glu Ser Gly Gly Gly Leu Val Gln Pro Gly Arg
 1               5                  10                  15

Ser Leu Arg Leu Ser Cys Glu Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Leu Ser Arg Thr Ser Val Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Pro Glu Asp Thr Ala Leu Tyr Tyr Cys
                85                  90                  95

Ala Lys Trp Gly Thr Arg Gly Tyr Phe Asp Tyr Trp Gly Gln Gly Thr
            100                 105                 110

Leu Val Thr Val Ser Ser
        115
```

<210> SEQ ID NO 582
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid

<400> SEQUENCE: 582

```
Xaa Xaa Xaa Xaa Xaa Xaa Xaa Xaa
 1               5
```

<210> SEQ ID NO 583
<211> LENGTH: 8
<212> TYPE: PRT
<213> ORGANISM: Artificial Sequence
<220> FEATURE:

```
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid

<400> SEQUENCE: 583

Xaa Xaa Xaa Xaa Xaa Xaa Xaa Xaa
 1               5

<210> SEQ ID NO 584
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(21)
<223> OTHER INFORMATION: Xaa = ANy amino acid

<400> SEQUENCE: 584

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa
            20

<210> SEQ ID NO 585
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(6)
<223> OTHER INFORMATION: Xaa = Any amino acid

<400> SEQUENCE: 585

Xaa Xaa Xaa Xaa Xaa Xaa
 1               5

<210> SEQ ID NO 586
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(3)
<223> OTHER INFORMATION: Xaa = Any amino acid

<400> SEQUENCE: 586

Xaa Xaa Xaa
 1

<210> SEQ ID NO 587
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(9)
<223> OTHER INFORMATION: Xaa = Any amino acid

<400> SEQUENCE: 587
```

-continued

Xaa Xaa Xaa Xaa Xaa Xaa Xaa Xaa
1               5

<210> SEQ ID NO 588
<211> LENGTH: 330
<212> TYPE: PRT
<213> ORGANISM: Artificial Sequence
<220> FEATURE:
<223> OTHER INFORMATION: Synthetic

<400> SEQUENCE: 588

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 589
<211> LENGTH: 327

<212> TYPE: PRT
<213> ORGANISM: Artificial Sequence
<220> FEATURE:
<223> OTHER INFORMATION: Synthetic

<400> SEQUENCE: 589

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 590
<211> LENGTH: 327
<212> TYPE: PRT
<213> ORGANISM: Artificial Sequence
<220> FEATURE:
<223> OTHER INFORMATION: Synthetic

<400> SEQUENCE: 590

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
             50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325
```